US012138142B2

(12) United States Patent
Heil et al.

(10) Patent No.: US 12,138,142 B2
(45) Date of Patent: Nov. 12, 2024

(54) APPARATUS FOR THE DETECTION OF MOISTURE

(71) Applicant: Hill-Rom Services, Inc., Batesville, IN (US)

(72) Inventors: Thomas F. Heil, Batesville, IN (US); Steven Alan Dixon, Riverview, FL (US); Laetitia Gazagnes, Montpellier (FR); Timothy A. Lane, II, Shrewsbury, MA (US); David Lance Ribble, Indianapolis, IN (US); Varad Narayan Srivastava, Batesville, IN (US); Charles A. Lachenbruch, Batesville, IN (US); Michael Scott Hood, Batesville, IN (US); Charles A. Howell, Knoxville, TN (US); Kirsten M. Emmons, Batesville, IN (US)

(73) Assignee: HILL-ROM SERVICES, INC., Batesville, IN (US)

( * ) Notice: Subject to any disclaimer, the term of this patent is extended or adjusted under 35 U.S.C. 154(b) by 171 days.

(21) Appl. No.: 17/723,574

(22) Filed: Apr. 19, 2022

(65) Prior Publication Data

US 2022/0249297 A1  Aug. 11, 2022

Related U.S. Application Data

(63) Continuation of application No. 17/197,391, filed on Mar. 10, 2021, now Pat. No. 11,331,227, which is a
(Continued)

(51) Int. Cl.
*A61F 13/42* (2006.01)
*A61B 5/00* (2006.01)
(Continued)

(52) U.S. Cl.
CPC .............. *A61F 13/42* (2013.01); *A61B 5/202* (2013.01); *A61B 5/6892* (2013.01); *A61B 5/74* (2013.01);
(Continued)

(58) Field of Classification Search
CPC .. A61F 13/42; A61F 2013/424; A61F 13/505; A61F 2013/15056; A61B 5/202;
(Continued)

(56) References Cited

U.S. PATENT DOCUMENTS 1,772,232 A   8/1930   Guilder
2,127,538 A   8/1938   Seiger
(Continued)

FOREIGN PATENT DOCUMENTS

CA    2361145 A1    12/1999
CA    2494896 A1    12/1999
(Continued)

OTHER PUBLICATIONS

International Search Report, dated Sep. 12, 2014, on PCT/US2014/024214 filed on Mar. 12, 2014, 19 pages.
(Continued)

*Primary Examiner* — Eric Blount
(74) *Attorney, Agent, or Firm* — Barnes & Thornburg LLP

(57) ABSTRACT

A moisture management apparatus monitors an area for moisture events and wirelessly transmits moisture-related information to one or more notification devices. An embodiment of the moisture management apparatus includes a substrate and one or more sensors supported by the substrate. The sensor(s) emit wireless signals indicative of the moisture-related information. A sensor event communication system forwards the sensor signals to another device, such as a notification device. The sensor event communica-
(Continued)

tion system may monitor other types of patient events. Portions of the moisture management apparatus and/or the moisture event communication system may be embodied in a patient support apparatus, such as a bed.

20 Claims, 42 Drawing Sheets

Related U.S. Application Data continuation of application No. 16/837,442, filed on Apr. 1, 2020, now Pat. No. 10,973,701, which is a continuation of application No. 16/357,694, filed on Mar. 19, 2019, now Pat. No. 10,682,263, which is a continuation of application No. 16/011,912, filed on Jun. 19, 2018, now Pat. No. 10,299,968, which is a continuation of application No. 15/123,109, filed as application No. PCT/US2014/055066 on Sep. 11, 2014, now Pat. No. 10,022,277, which is a continuation-in-part of application No. PCT/US2014/024214, filed on Mar. 12, 2014.

(60) Provisional application No. 61/899,655, filed on Nov. 4, 2013, provisional application No. 61/820,768, filed on May 8, 2013, provisional application No. 61/778,830, filed on Mar. 13, 2013.

(51) Int. Cl.
*A61B 5/20* (2006.01)
*A61G 7/05* (2006.01)
*G06K 7/10* (2006.01)
*A61G 7/02* (2006.01)

(52) U.S. Cl.
CPC ............ *A61G 7/05* (2013.01); *G06K 7/10366* (2013.01); *A61F 2013/424* (2013.01); *A61G 7/02* (2013.01)

(58) Field of Classification Search
CPC ....... A61B 5/6892; A61B 5/74; A61B 5/6808; A61B 5/0002; A61B 5/1113; A61G 7/05; A61G 7/02; G06K 7/10366; G08B 21/20; G08B 25/10
USPC ......................................................... 340/604
See application file for complete search history.

(56) References Cited

U.S. PATENT DOCUMENTS

| | | | |
|---|---|---|---|
| 2,644,050 A | 6/1953 | Seiger | |
| 2,668,202 A | 2/1954 | Kaplan | |
| 2,726,294 A | 12/1955 | Kroening et al. | |
| 2,907,841 A | 10/1959 | Campbell | |
| 3,199,095 A | 8/1965 | Ashida | |
| 3,971,371 A | 7/1976 | Bloom | |
| 4,001,531 A | 1/1977 | Crockett, Sr. | |
| 4,069,817 A | 1/1978 | Fenote et al. | |
| 4,106,001 A | 8/1978 | Mahoney | |
| 4,163,449 A | 8/1979 | Regal | |
| 4,191,950 A | 3/1980 | Levin et al. | |
| 4,212,295 A | 7/1980 | Snyder | |
| 4,228,426 A | 10/1980 | Roberts | |
| 4,347,503 A | 8/1982 | Uyehara | |
| 4,539,559 A | 9/1985 | Kelley et al. | |
| 4,747,166 A | 5/1988 | Kuntz | |
| 4,965,554 A | 10/1990 | Darling | |
| 5,081,422 A | 1/1992 | Shih | |
| 5,086,294 A | 2/1992 | Schwab, Jr. | |
| 5,137,033 A | 8/1992 | Norton | |
| 5,144,284 A | 9/1992 | Hammett | |
| 5,291,181 A | 3/1994 | De Ponte | |
| 5,438,721 A | 8/1995 | Pahno et al. | |
| 5,459,452 A | 10/1995 | DePonte | |
| 5,491,609 A | 2/1996 | Dankman et al. | |
| 5,537,095 A | 7/1996 | Dick et al. | |
| 5,570,082 A | 10/1996 | Mahgerefteh et al. | |
| 5,675,854 A | 10/1997 | Zibelin | |
| 5,760,694 A | 6/1998 | Nissim | |
| 5,790,035 A | 8/1998 | Ho | |
| 5,824,883 A | 10/1998 | Park et al. | |
| 5,910,080 A | 6/1999 | Selton | |
| 5,947,943 A | 9/1999 | Lee | |
| 6,028,241 A | 2/2000 | Armstead | |
| 6,047,419 A | 4/2000 | Fergusaon | |
| 6,097,297 A * | 8/2000 | Fard ........................ | A61F 13/42 340/573.5 |
| 6,104,311 A | 8/2000 | Lastinger | |
| 6,292,102 B1 | 9/2001 | Smith | |
| 6,340,932 B1 | 1/2002 | Rodgers et al. | |
| 6,341,393 B1 | 1/2002 | Votel | |
| 6,351,215 B2 | 2/2002 | Rodgers et al. | |
| 6,362,737 B1 | 3/2002 | Rodgers et al. | |
| 6,384,728 B1 | 5/2002 | Kanor et al. | |
| 6,544,200 B1 | 4/2003 | Smith et al. | |
| 6,552,661 B1 | 4/2003 | Lastinger et al. | |
| 6,559,772 B2 | 5/2003 | Zand et al. | |
| 6,583,722 B2 | 6/2003 | Jeutter et al. | |
| 6,603,403 B2 | 8/2003 | Jeutter et al. | |
| 6,621,410 B1 | 9/2003 | Lastinger et al. | |
| 6,639,517 B1 | 10/2003 | Chapman et al. | |
| 6,774,800 B2 * | 8/2004 | Friedman ................ | A61F 13/42 340/573.5 |
| 6,831,562 B2 | 12/2004 | Rodgers et al. | |
| 6,832,507 B1 | 12/2004 | van de Berg et al. | |
| 6,933,849 B2 | 8/2005 | Sawyer | |
| 6,948,205 B2 | 9/2005 | Van Der Wurf et al. | |
| 6,982,646 B2 | 1/2006 | Rodgers et al. | |
| 7,017,213 B2 | 3/2006 | Chisari | |
| 7,030,731 B2 | 4/2006 | Lastinger et al. | |
| 7,071,830 B2 | 7/2006 | Sahlberg et al. | |
| 7,120,952 B1 | 10/2006 | Bass et al. | |
| 7,141,715 B2 | 11/2006 | Shapira | |
| 7,181,206 B2 | 2/2007 | Pedersen | |
| 7,250,547 B1 | 7/2007 | Hofmeister et al. | |
| 7,253,729 B2 | 8/2007 | Lastinger et al. | |
| 7,274,944 B2 | 9/2007 | Lastinger et al. | |
| 7,302,278 B2 | 11/2007 | Lastinger et al. | |
| 7,305,246 B2 | 12/2007 | Lastinger et al. | |
| 7,308,270 B2 | 12/2007 | Lastinger et al. | |
| 7,348,930 B2 | 3/2008 | Lastinger et al. | |
| 7,349,701 B2 | 3/2008 | Lastinger et al. | |
| 7,355,090 B2 | 4/2008 | Ales, III et al. | |
| 7,359,675 B2 | 4/2008 | Lastinger et al. | |
| 7,400,860 B2 | 7/2008 | Lastinger et al. | |
| 7,424,298 B2 | 9/2008 | Lastinger et al. | |
| 7,489,252 B2 | 2/2009 | Long et al. | |
| 7,489,282 B2 | 2/2009 | Lastinger et al. | |
| 7,498,478 B2 | 3/2009 | Long et al. | |
| 7,551,089 B2 | 6/2009 | Sawyer | |
| 7,586,385 B2 | 9/2009 | Rokhsaz | |
| 7,595,734 B2 | 9/2009 | Long et al. | |
| 7,595,756 B2 | 9/2009 | Lastinger et al. | |
| 7,598,853 B2 | 10/2009 | Becker et al. | |
| 7,598,862 B2 | 10/2009 | Lastinger et al. | |
| 7,599,699 B2 | 10/2009 | Lastinger et al. | |
| 7,616,959 B2 | 11/2009 | Spenik et al. | |
| 7,633,378 B2 | 12/2009 | Rodgers et al. | |
| 7,649,125 B2 | 1/2010 | Ales, III et al. | |
| 7,663,483 B2 | 2/2010 | Spenik et al. | |
| 7,667,600 B2 | 2/2010 | Woodbury et al. | |
| 7,812,731 B2 | 10/2010 | Bunza et al. | |
| 7,822,386 B2 | 10/2010 | Lastinger et al. | |
| 7,834,234 B2 | 11/2010 | Roe et al. | |
| 7,834,235 B2 | 11/2010 | Long et al. | |
| 7,834,765 B2 | 11/2010 | Sawyer | |
| 7,834,766 B2 | 11/2010 | Sawyer | |
| 7,838,720 B2 | 11/2010 | Roe et al. | |
| 7,849,544 B2 | 12/2010 | Flocard et al. | |
| 7,873,319 B2 | 1/2011 | Lastinger et al. | |
| 7,977,529 B2 | 7/2011 | Bergman et al. | |

(56) References Cited

U.S. PATENT DOCUMENTS

| | | |
|---|---|---|
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,471,715 B2 * | 6/2013 | Solazzo .................. A61F 13/42 340/573.5 |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 9,048,819 B2 | 6/2015 | Rokhsaz et al. |
| 9,107,776 B2 | 8/2015 | Bergman et al. |
| 9,119,748 B2 * | 9/2015 | Abraham .................. A61F 13/42 |
| 9,366,644 B1 | 6/2016 | Lastinger et al. |
| 9,649,230 B1 | 5/2017 | Li |
| 9,681,996 B2 | 6/2017 | Prioleau et al. |
| 9,806,886 B2 | 10/2017 | Rajsic |
| 10,022,277 B2 | 7/2018 | Heil et al. |
| 10,121,353 B1 | 11/2018 | Billman et al. |
| 10,163,326 B1 | 12/2018 | Billman et al. |
| 10,299,968 B2 | 5/2019 | Heil et al. |
| 10,682,263 B2 | 6/2020 | Heil et al. |
| 10,973,701 B2 | 4/2021 | Heil et al. |
| 11,331,227 B2 | 5/2022 | Heil et al. |
| 2002/0011932 A1 | 1/2002 | Rodgers et al. |
| 2002/0033757 A1 | 3/2002 | Rodgers et al. |
| 2002/0145525 A1 | 10/2002 | Friedman et al. |
| 2002/0145526 A1 * | 10/2002 | Friedman .............. A61B 5/0002 340/573.5 |
| 2003/0030568 A1 | 2/2003 | Lastinger et al. |
| 2004/0220538 A1 * | 11/2004 | Panopoulos ............ A61F 13/42 604/361 |
| 2005/0003763 A1 | 1/2005 | Lastinger et al. |
| 2005/0003865 A1 | 1/2005 | Lastinger et al. |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2010/0271187 A1 * | 10/2010 | Uysal .................. G06K 7/10079 340/10.4 |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0095884 A1 | 4/2011 | Xu et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 * | 12/2011 | Bunza .................... A61B 5/202 340/573.5 |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0130330 A1 | 5/2012 | Wilson et al. |
| 2012/0157947 A1 | 6/2012 | Nhan et al. |
| 2012/0165772 A1 | 6/2012 | Groosman et al. |
| 2012/0206265 A1 * | 8/2012 | Solazzo .................. A61F 13/42 340/573.5 |
| 2012/0216607 A1 | 8/2012 | Sjöholm et al. |
| 2012/0217311 A1 | 8/2012 | Rokhsaz et al. |
| 2012/0268278 A1 | 10/2012 | Lewis et al. |
| 2013/0019405 A1 | 1/2013 | Flanagan |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0296808 A1 | 10/2014 | Curran et al. |
| 2014/0358099 A1 | 12/2014 | Durgin et al. |
| 2014/0375297 A1 * | 12/2014 | Geiger .................... A61F 13/42 604/361 |
| 2015/0080819 A1 | 3/2015 | Charna et al. |
| 2015/0080834 A1 | 3/2015 | Mills |
| 2015/0087935 A1 | 3/2015 | Davis et al. |
| 2017/0065464 A1 | 3/2017 | Heil et al. |
| 2018/0296401 A1 | 10/2018 | Heil et al. |
| 2019/0209391 A1 | 7/2019 | Heil et al. |
| 2020/0306101 A1 | 10/2020 | Heil et al. |
| 2021/0186773 A1 | 6/2021 | Heil et al. |

FOREIGN PATENT DOCUMENTS

| | | |
|---|---|---|
| CN | 101304715 A | 11/2008 |
| CN | 102568259 A | 7/2012 |
| CN | 202711437 U | 1/2013 |
| CN | 102985853 A | 3/2013 |
| DE | 4137631 A | 5/1992 |
| DE | 69906388 T2 | 2/2004 |
| DE | 69915370 T2 | 3/2005 |
| DE | 69917491 T2 | 5/2005 |

(56) References Cited

FOREIGN PATENT DOCUMENTS

| | | |
|---|---|---|
| DE | 60016946 T2 | 6/2006 |
| DE | 102007050074 A1 | 4/2009 |
| EP | 0335279 A1 | 10/1989 |
| EP | 1286179 A2 | 12/1999 |
| EP | 1147603 A2 | 10/2001 |
| EP | 1149305 A2 | 10/2001 |
| EP | 1153317 A2 | 11/2001 |
| EP | 1218771 A2 | 7/2002 |
| EP | 1153317 B1 | 3/2003 |
| EP | 1147603 B1 | 3/2004 |
| EP | 1410353 A2 | 4/2004 |
| EP | 1149305 B1 | 5/2004 |
| EP | 1218771 B1 | 12/2004 |
| EP | 1684615 A1 | 8/2006 |
| EP | 2014267 A1 | 6/2007 |
| EP | 1868553 A1 | 12/2007 |
| EP | 1897278 A1 | 3/2008 |
| EP | 1959900 A1 | 8/2008 |
| EP | 1994650 A2 | 11/2008 |
| EP | 2019659 A1 | 2/2009 |
| EP | 1410353 B1 | 12/2009 |
| EP | 1897278 B1 | 1/2010 |
| EP | 1684615 B1 | 2/2010 |
| EP | 2156222 A1 | 2/2010 |
| EP | 2313044 A2 | 4/2011 |
| EP | 2579069 A2 | 6/2011 |
| EP | 2444039 A1 | 8/2011 |
| EP | 1959900 B1 | 2/2012 |
| EP | 2738748 A1 | 4/2012 |
| EP | 2452183 A1 | 5/2012 |
| EP | 2496197 A1 | 9/2012 |
| EP | 1994650 B1 | 12/2012 |
| EP | 2542200 A1 | 1/2013 |
| EP | 2548473 A2 | 1/2013 |
| EP | 2582341 A1 | 4/2013 |
| EP | 2729107 A1 | 5/2014 |
| EP | 2739254 A1 | 6/2014 |
| EP | 2156222 B1 | 8/2015 |
| EP | 2496197 B1 | 8/2015 |
| EP | 2019659 B1 | 4/2016 |
| EP | 2582341 B1 | 4/2016 |
| EP | 2739254 B1 | 11/2016 |
| GB | 145859 | 3/1919 |
| GB | 2145859 | 4/1985 |
| GB | 2408204 A | 11/2003 |
| WO | WO 89/10110 A1 | 4/1989 |
| WO | WO 94/20002 A1 | 3/1994 |
| WO | WO 00/44091 A2 | 7/2000 |
| WO | WO 01/25817 A2 | 4/2001 |
| WO | WO 02/103645 A2 | 12/2002 |
| WO | WO 2006/108540 A1 | 10/2006 |
| WO | WO 2007/069968 A1 | 6/2007 |
| WO | WO 2008/130298 A1 | 10/2008 |
| WO | WO 2010/001271 A2 | 1/2010 |
| WO | WO 2010/001271 A3 | 1/2010 |
| WO | WO 2010/043368 A1 | 4/2010 |
| WO | WO 2011/043724 A1 | 4/2011 |
| WO | WO 2011/107580 A1 | 9/2011 |
| WO | WO 2012/136157 A1 | 10/2012 |
| WO | WO 2014/165041 A2 | 10/2014 |
| WO | WO 2015/137999 | 9/2015 |

OTHER PUBLICATIONS

PCT Search Report and Written Opinion for PCT/US20140055066.
First Office Action and its English translation for Chinese Patent Application No. 201480078481.6 dated May 22, 2008; 26 pages.
Extended EP Search Report for European Patent Application No. 14885467.2 dated Feb. 28, 2017; 10 pages.
Communication Pursuant to Article 94(3) EPC for European Patent Application No. 14885467.2 dated Apr. 4, 2018; 6 pages.
Extended EP Search Report for European Patent Application No. 14778216.3 dated Apr. 29, 2016; 6 pages.
Communication pursuant to Article 94(3) EPC from the European Patent Office for European Patent Application No. 14885467.2 dated Jun. 25, 2019; 6 pages.
First Office Action of Chinese Patent Application No. 201910224351.3 dated Dec. 2, 2021 and its English translation (12 pages).
Communication pursuant to Article 94(3) EPC issued in European Patent Application No. 14885467.2; dated Jan. 2, 2024 (4 pages).

* cited by examiner

| EXCITATION FREQUENCY YIELDING STRONG RSSI | FLUID IDENTITY AND/OR PROPERTIES |
|---|---|
| $f_{T+n}$ | |
| ⋮ | |
| $f_{T+2}$ | VOMIT |
| $f_{T+1}$ | BLOOD |
| $f_C$ | NO FLUID |
| $f_{T-1}$ | URINE – ACIDIC |
| $f_{T-2}$ | URINE – ALKALINE |
| ⋮ | |
| $f_{T-n}$ | |

*FIG. 11*

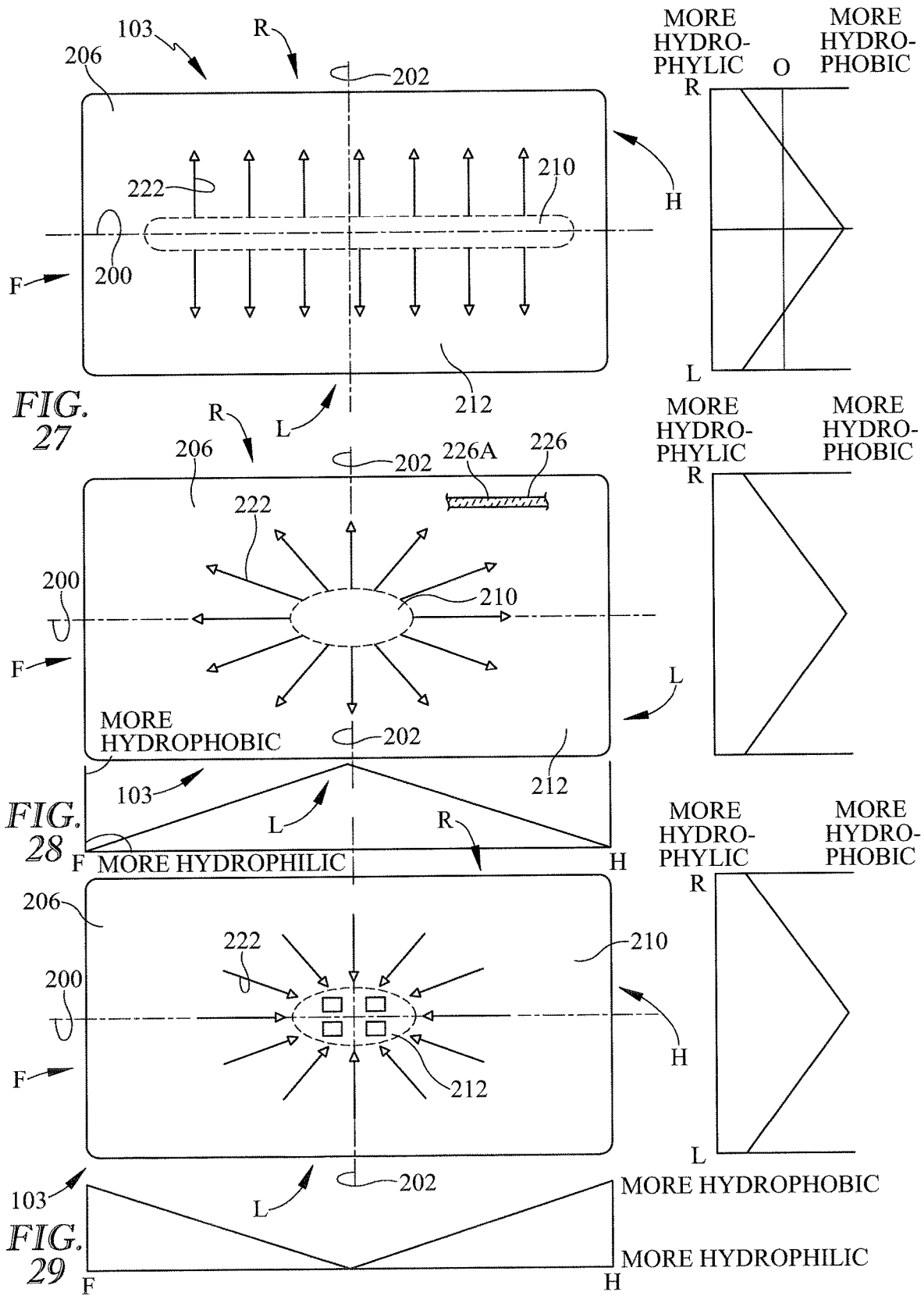

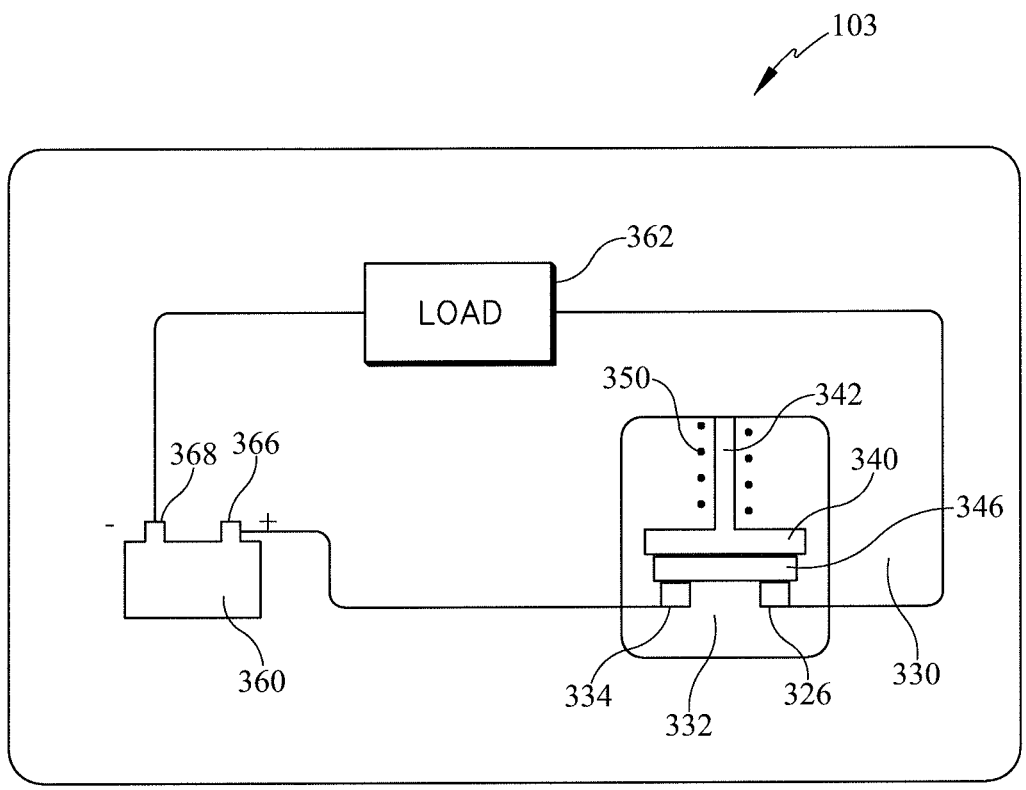
FIG. 35
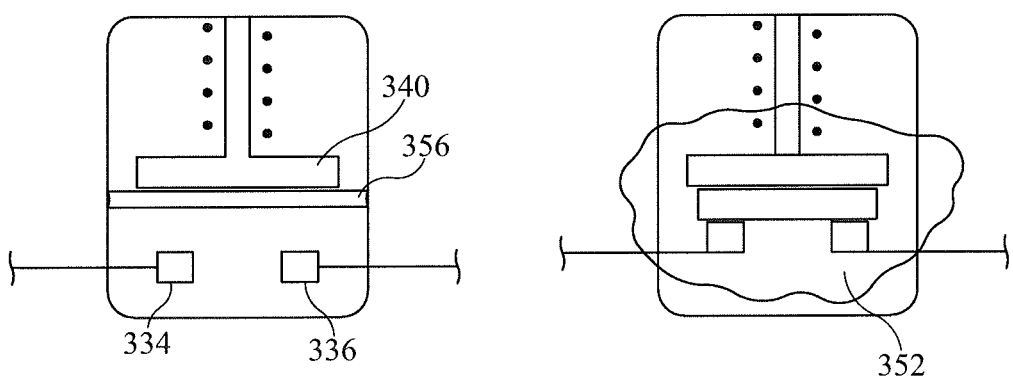
FIG. 37
FIG. 36

APPARATUS FOR THE DETECTION OF MOISTURE

This application is a continuation of U.S. application Ser. No. 17/197,391, filed Mar. 10, 2021, now U.S. Pat. No. 11,331,227, which is a continuation of U.S. application Ser. No. 16/837,442, filed Apr. 1, 2020, now U.S. Pat. No. 10,973,701, which is a continuation of U.S. application Ser. No. 16/357,694, filed Mar. 19, 2019, now U.S. Pat. No. 10,682,263, which is a continuation of U.S. application Ser. No. 16/011,912, filed Jun. 19, 2018, now U.S. Pat. No. 10,299,968, which is a continuation of U.S. application Ser. No. 15/123,109, filed Sep. 1, 2016, now U.S. Pat. No. 10,022,277, which is a U.S. national phase of International Application No. PCT/US2014/055066, filed Sep. 11, 2014, which claims the benefit of and priority to, and is a continuation-in-part of International Application No. PCT/US2014/024214, filed Mar. 12, 2014, which claims the benefit of and priority to U.S. Provisional Application No. 61/899,655, filed Nov. 4, 2013, and U.S. Provisional Application No. 61/820,768, filed May 8, 2013, and U.S. Provisional Application No. 61/778,830, filed Mar. 13, 2013, all of which are incorporated herein by this reference in their entirety.

SUMMARY

The subject matter described herein relates to bed systems, patient support apparatuses, healthcare communication systems, methods and apparatuses for the detection of incontinence or other moisture, methods of analysis of detected fluids, and multifunctional sensor systems. The present invention may comprise one or more of the features recited in the appended claims and/or one or more of the following features or combinations thereof.

At least one embodiment of a method of detecting the presence of moisture on an occupant support includes the steps of providing one or more moisture responsive sensors in an occupant support, exciting the sensors with an electromagnetic signal; monitoring for a response from the sensors; comparing the response to an expected response; and based on the comparison, issuing an output.

BRIEF DESCRIPTION OF THE DRAWINGS

The foregoing and other features of the various embodiments of the methods and apparatuses described herein will become more apparent from the following detailed description and the accompanying drawings in which:

FIG. 11 shows a simplified sample correlation for use in the method of FIG. 10.

FIGS. 27-29 are simplified depictions of variants of an embodiment of an architecture for a moisture handling apparatus, which may be an incontinence pad in which the pad has a hydroaffinity property for directing moisture from a source to a destination.

FIGS. 35-36 is a simplified depiction of an embodiment of a system including a sensor pad which may be an incontinence pad, and which includes a switch and a fuse in the form of a patch of material and in which the switch has an open state in which the fuse impedes the establishment of an electrical connection between switch terminals and a closed state in which the fuse enables the establishment of the electrical connection in response to a stimulus having acted on the fuse.

FIG. 37 is a simplified depiction of an alternative embodiment of FIGS. 35-36 in which the fuse is a membrane.

DETAILED DESCRIPTION

System for Detecting Incontinence or Other Moisture Caused Abnormality.

Figure 1A:
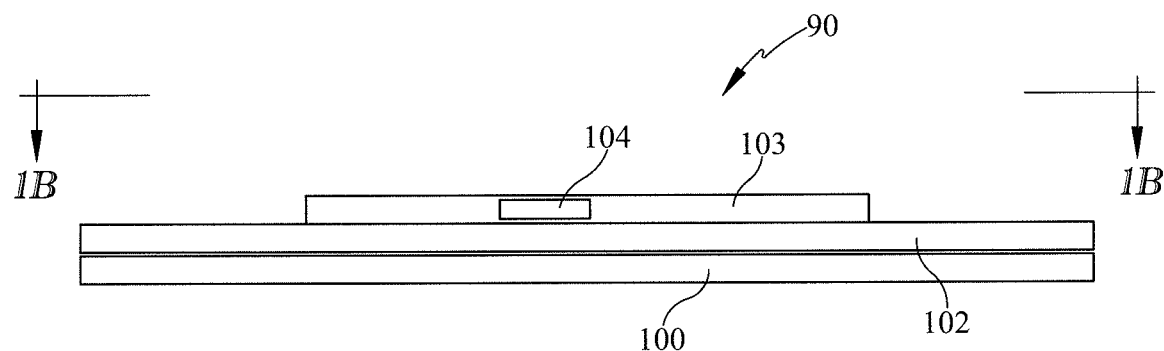
FIGS. 1A and 1B are simplified schematic side elevation and plan views of an embodiment of an occupant support exemplified as a bed such as a hospital bed and showing a sensor mat resting on a mattress of the bed and also showing associated components of a system for detecting moisture on the occupant support.
Figure 1B:
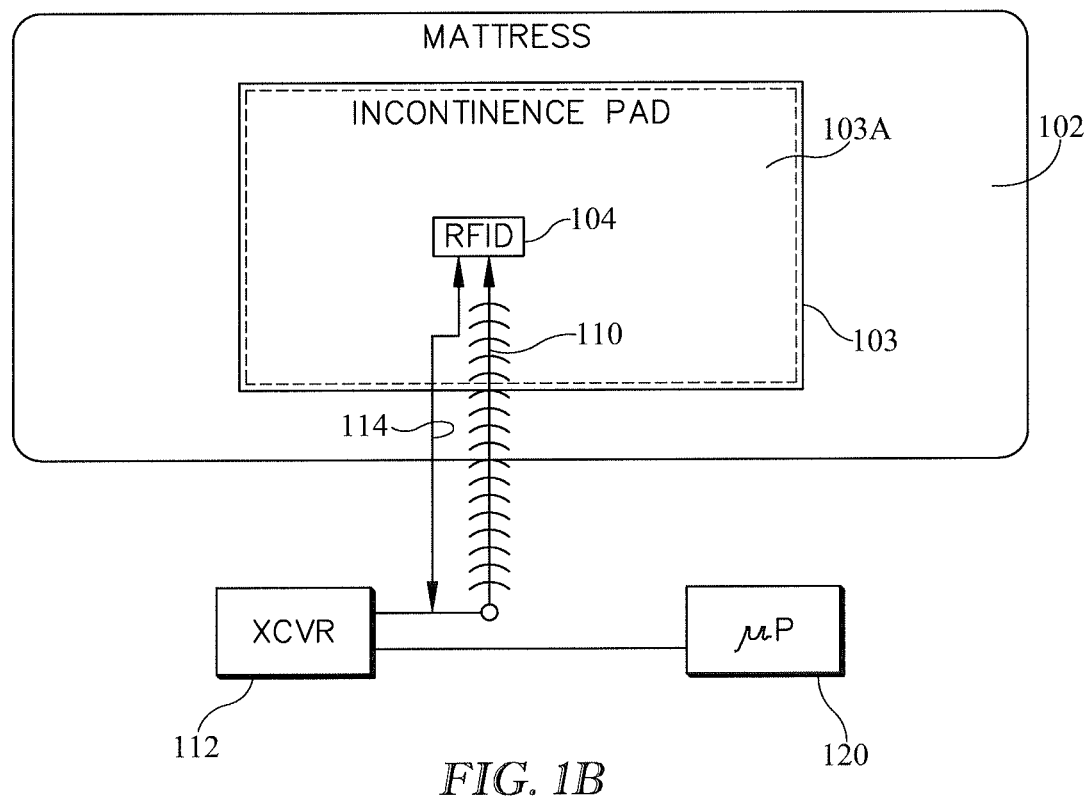

FIGS. 1A-1B schematically show an occupant support 90 such as a hospital bed 90. The occupant support 90 may be embodied as, for example, a hospital bed, a residential bed, a chair, a wheelchair, a mattress, a stretcher, a patient transport device, or other type of person support apparatus. The illustrative occupant support includes a frame 100, and a mattress 102 supported on the frame. An incontinence pad 103 rests on the mattress in an area or zone 103A (dashed lines) thereof in which it is desired to conduct surveillance for unwanted moisture or other moisture related abnormality. In other embodiments, the pad 103 may be disposed within or integrated with the mattress 102. In still other embodiments, the pad 103 may be embodied as a wearable device; for example, the pad 103 may be affixed to or integrated with an undergarment or other article of clothing (e.g., by an adhesive, clip, or other fastener), or the pad 103 may be embodied as a diaper or a disposable undergarment. In the illustrated occupant support the surveillance zone is substantially congruent with the pad 103. Although the pad is referred to as an incontinence pad and this application uses incontinence accidents (urine) as an example, the moisture of concern may be other forms of moisture such as perspiration, blood, water, perspiration, moisture present in material such as fecal matter which has moisture content, or any other type of human-generated moisture. In addition, although this application will use the pad 103 as an example, other types of articles may be used to conduct moisture surveillance in the surveillance zone. These include a bed sheet or a portion thereof, a mattress ticking or a portion thereof and a garment worn by the occupant of the occupant support.

Figure 3:
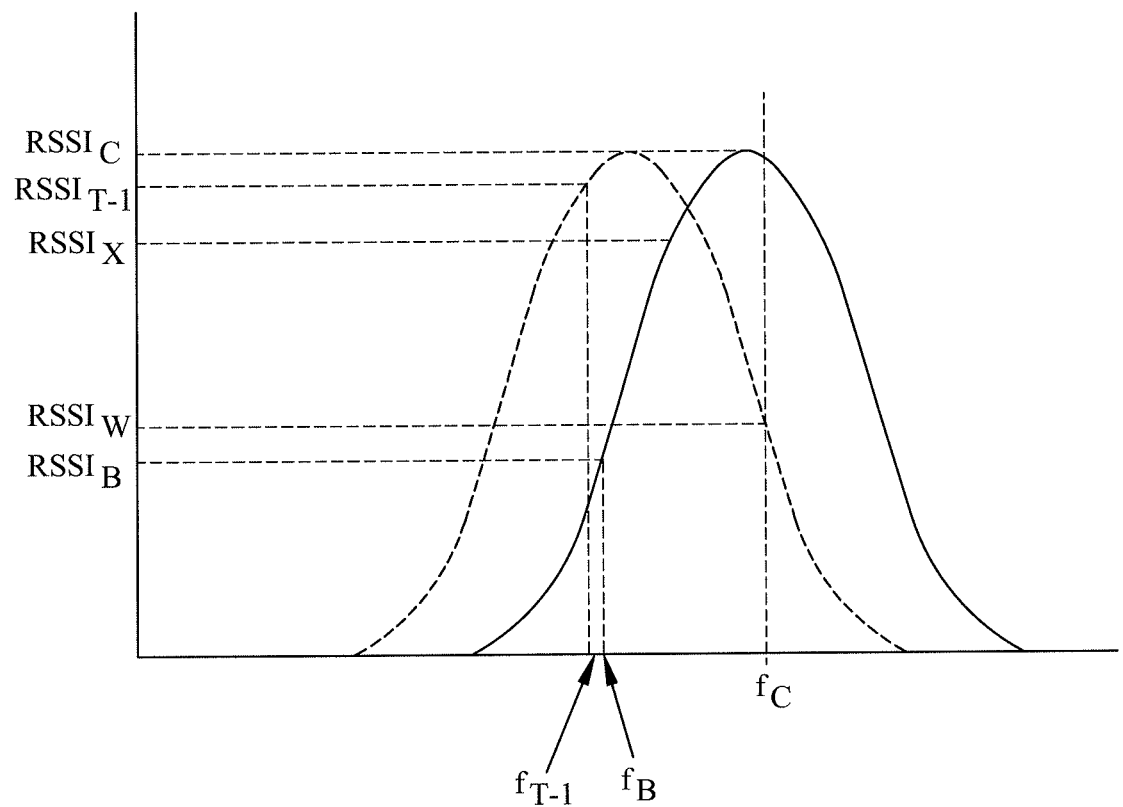
FIG. 3 is a simplified graph showing the Return Signal Strength Indicator (RSSI) of an RFID sensor in a baseline state (solid line) and in a mistuned state (dashed line), which mistuned state may be attributable to the presence of moisture on the RFID.

The illustrative system for detecting the presence of moisture on the occupant support includes one or more moisture responsive sensors 104, which are part of the pad 103. The example sensor(s) described in the examples of this application are RFID (Radio Frequency Identification) tags or sensors. In some embodiments, the sensor(s) 104 are tuned to a center frequency. This is seen in the example of FIG. 3, where the solid line bell shaped curve represents the tuning of the RFID sensor and the center frequency is labeled fC. When the RFID is excited by an electromagnetic signal 110 having a frequency at or near fC, for example a signal generated by a transceiver 112 such as Texas Instruments model TRF7960 transceiver, the RFID returns a return or response signal 114 whose Return Signal Strength Indicator (RSSI) in the transceiver is strong. For example, considering the solid line bell shaped curve of FIG. 3, if the transceiver excites the RFID at fC it receives a response whose RSSI is RSSIC. If the transceiver excites the RFID at fB (which is not near the tuned frequency), the transceiver receives a response whose RSSI is RSSIB. Whether the RSSI of the return signal is considered to be "strong" or "weak" for a given application of the RFID is determined by a designer of the given application.

The transceiver 112 is adapted to excite the sensor 104 with an electromagnetic signal 110 having a frequency approximately equal to the center frequency of the sensor and to monitor for a center frequency response from the sensor. "Center frequency response" means the RSSI of the return signal returned as a result of the sensor having been excited at its center frequency. In these embodiments, the transceiver 112 may have a fixed center frequency. However, in other embodiments, the transceiver 112 may be able to adjust the center frequency. Further, the sensor 104 may come in contact with moisture, and the moisture on the sensor 104 may change the conductance or capacitance of the sensor 104, with the result being that the sensor 104 is no longer tuned for the center frequency. Thus, as an alternative to comparing the sensor's response to an expected response to the center frequency, the system can monitor the differences in the RSSI over time in response to a number of different test frequencies, in order to determine whether a moisture event has occurred. For example, instead of comparing the sensor's response to an expected response, the system can compare the sensor's response to responses previously received from the sensor (e.g., the sensor's response to different test frequencies). Any of the sensor systems or methods of sensor interrogation disclosed herein may be modified as described above in accordance with the requirements of a particular design or implementation of the system.

The illustrated system for detecting the presence of moisture on the occupant support also includes electrical circuitry, such as a processor 120, which is adapted to compare the center frequency response to an expected center frequency response. For example the expected center frequency response for the center frequency fC of FIG. 3 (continuing to refer to the solid line bell shaped curve) is RSSIC plus or minus some tolerance, e.g. between RSSIC and RSSIX. The processor also issues an output, referred to as a first output, if the center frequency response compares favorably to an expected center frequency response, e.g. if the RSSI is between RSSIC and RSSIX. The comparison is considered to be a favorable one (and the RSSI is considered to be strong) if the RSSI is within the expected range or tolerance, for example between RSSIC and RSSIX.

If the center frequency response does not compare favorably with the expected center frequency response (e.g. if the return signal RSSI is a weak response such as RSSIW) this may be the result of the tuning of the RFID sensor having changed, for example due to contamination of the RFID antenna by moisture. This is indicated by the dashed line bell shaped curve. Therefore, the processor commands the transceiver to excite the sensor with one or more electromagnetic test signals having test frequencies different than the center frequency for example fT1, which exceeds fC by a specified delta frequency, fT2 which exceeds fT1 by a delta frequency, fT−1 which is smaller than fC by a delta frequency, fT−2 which is lower than fT−1 by a delta frequency, and so forth. The above mentioned delta frequencies may be equal or unequal. The processor compares the test frequency response (the response the transceiver receives as a result of having excited the RFID at the test frequency) to an expected or desired test frequency response corresponding to the test frequency. If the test frequency response from the sensor compares favorably to an expected or desired test frequency response which corresponds to the test frequency, the processor issues a second output consistent with the favorable comparison between the test frequency response and the expected test frequency response corresponding to the test frequency. In the example of FIG. 3 the excitation at frequency fT−1 yields a return or response signal whose RSSI at the transceiver is a strong signal whose RSSI is $RSSI_{T-1}$ which is approximately equal to the return expected in response to excitation at center frequency fC. The fact that the response to fC is a weak response (RSSIB) and that the response at fT−1 is strong, reveals that the tuning of the sensor has changed, for example because of the RFID antenna having been contaminated with moisture. This is indicated by the position of the dashed line bell shaped curve relative to that of the solid line bell shaped curve.

The expected or desired test frequency response may be the RSSI associated with an "in-tune" RFID (plus or minus a tolerance) or may be an RSSI expected of an RFID tuned to the test frequency and which is not necessarily the same as the RSSI of the in-tune RFID. If the test frequency response from the sensor does not compare favorably to an expected test frequency response corresponding to the test frequency at any of the test frequencies, the processor issues a third output consistent with the unfavorable comparisons between the test frequency responses and the expected test frequency response corresponding to each of the test frequencies. In the foregoing example and many others in this application the sensor is an RFID sensor and therefore the electromagnetic excitation signals are radio frequency signals.

RSSI Based Method of Sensor Interrogation for Detecting Incontinence or Other Moisture Caused Abnormality.

Figure 2:
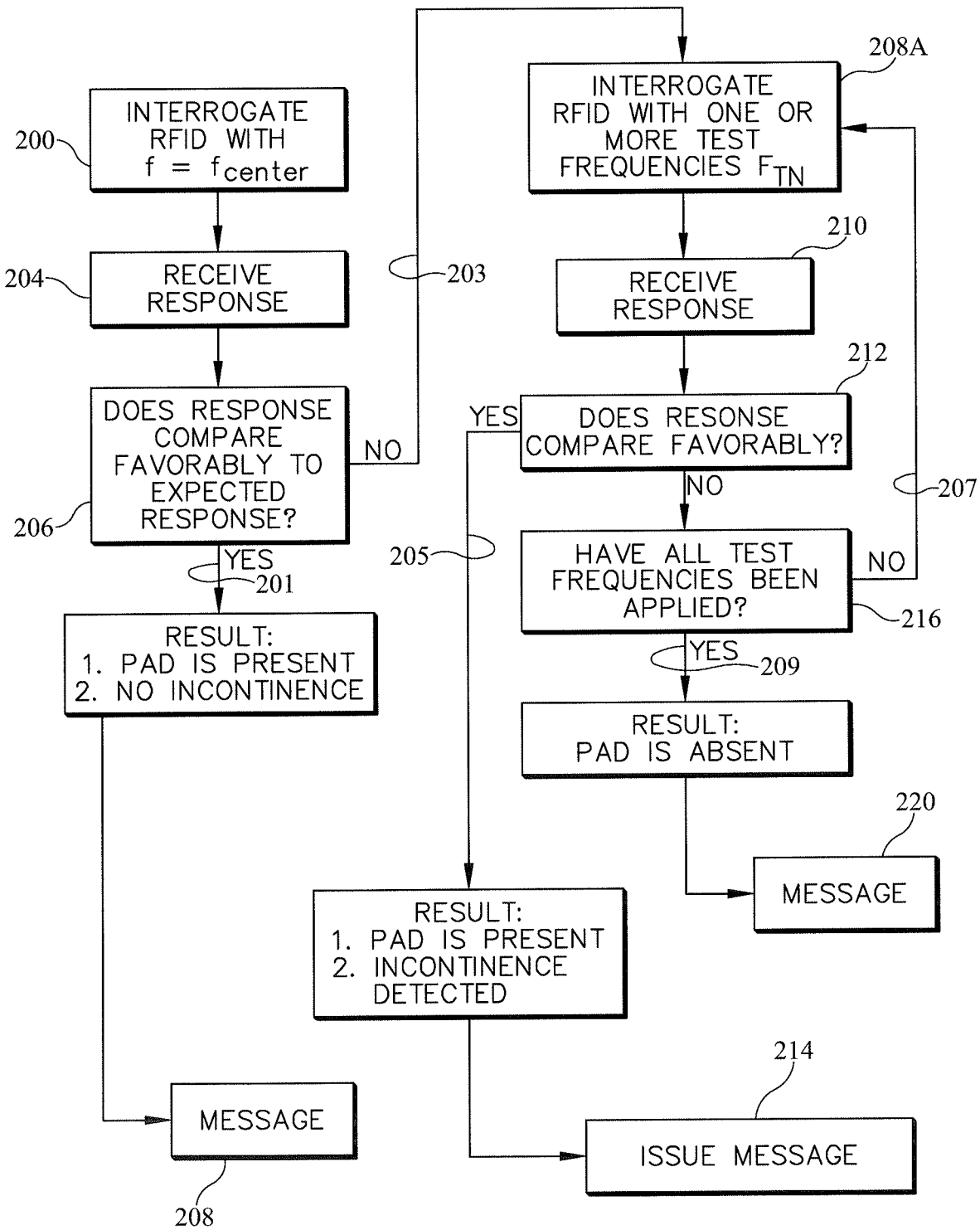
FIG. 2 is a simplified block diagram of an embodiment of a method for interrogating one or more sensors to detect the presence of moisture on an occupant support.

A method of detecting the presence of moisture on an occupant support, where one or more moisture responsive sensors are provided in a surveillance zone of the occupant support, is disclosed. The method includes exciting the one or more sensors with an electromagnetic signal; monitoring for a response from the one or more sensors; comparing the response to an expected response; and based on the comparing of the response to the expected response, issuing a first output. An illustrative embodiment of the method is shown in FIG. 2 and described below. In the embodiment of FIG. 2, the method includes interrogating a sensor to detect the presence of moisture on an occupant support. The method may be used with the architecture of FIGS. 1A and 1B. A moisture responsive sensor 104 is provided in the in a surveillance zone 103A of the occupant support. In the illustrated embodiment, the sensor is tuned to a center frequency fC (FIG. 3), and the sensor's response to an interrogation at the center frequency is used to detect moisture events. In other embodiments, other techniques may be used to analyze the sensor's output to determine whether a moisture event has occurred. For example, the signal strength of the signals emitted by the sensor over time may be analyzed (e.g., compared to known or threshold values, etc.). Further, in some embodiments, one or more of the signal characteristics are compared (e.g., frequency, amplitude); whereas, in other embodiments, variations in the signal characteristics are analyzed over time. For example, the rate of change of the signal frequency over time, or changes in the difference between the signal frequency and a target frequency (e.g., the center frequency) over time (as opposed to a comparison of the actual frequency values) may be used to detect the occurrence of a moisture event.

At block 200 the sensor is excited with an electromagnetic signal 110 having a frequency approximately equal to the center frequency. At block 204 transceiver 112 monitors for and receives a center frequency response from the sensor. The response may be a strong response or a weak response. The response may also be a "null" response, i.e. a response of no discernible RSSI or other indication of strength. At block 206 microprocessor 120 compares the center frequency response to an expected or desired center frequency response. If the center frequency response at block 206 compares favorably to the expected or desired center frequency response, the method follows path 201 so that the processor issues a first output 208 consistent with the favorable comparison. As seen in the illustration the first output is an indication that an incontinence pad is present and no incontinence is detected.

If the center frequency response does not compare favorably with the expected center frequency response, the method follows path 203. At block 208A the processor causes the transceiver to excite the sensor with one or more electromagnetic test signals having test frequencies different than the center frequency. After each excitation the transceiver monitors for a test frequency response at block 210. At block 212 the processor determines if the test frequency response from the sensor compares favorably to an expected test frequency response corresponding to the test frequency. If so, the method follows path 205 and processor 120 issues a second output 214 consistent with the favorable comparison between the test frequency response and the expected or desired test frequency response corresponding to the test frequency. The second output 214 is an indication that an incontinence pad is present and that incontinence has been detected. If not, the method proceeds to block 216 where the processor determines if all test frequencies of interest have been applied. If not, the method follows path 207 and applies additional test frequencies (block 208) and continues to monitor for a return (block 210) that compares favorably (block 212). If all test frequencies have been applied (block 216) without having received a favorable response (block 212) the method follows path 209 and the processor issues a third output consistent with the unfavorable comparison between the all the test frequency responses and their corresponding expected test frequency response. The third output is an indication that an incontinence pad is absent or a fault has occurred. The conclusion that the pad is absent may mean that the pad has been removed from the mattress, or it may mean that is has been displaced along the mattress far enough that it is out of communication with the transceiver.

As noted above in the context of the architecture of FIGS. 1A and 1B, the second output may be issued in response to a favorable comparison and without first exciting the sensor at any other test frequencies. Alternatively issuance of the second output may be deferred until at least one additional test frequency has been applied to the sensor or until all test frequencies of interest have been applied to the sensor, even if an earlier applied frequency yields a favorable comparison between the test frequency response and the expected or desired response at that test frequency. That is, the second output is not issued until the sensor has been excited at at least one frequency other than the test frequency that yielded a favorable comparison.

Rate of Change Based Method of Sensor Interrogation for Detecting Incontinence or Other Moisture Caused Abnormality.

Figure 4:
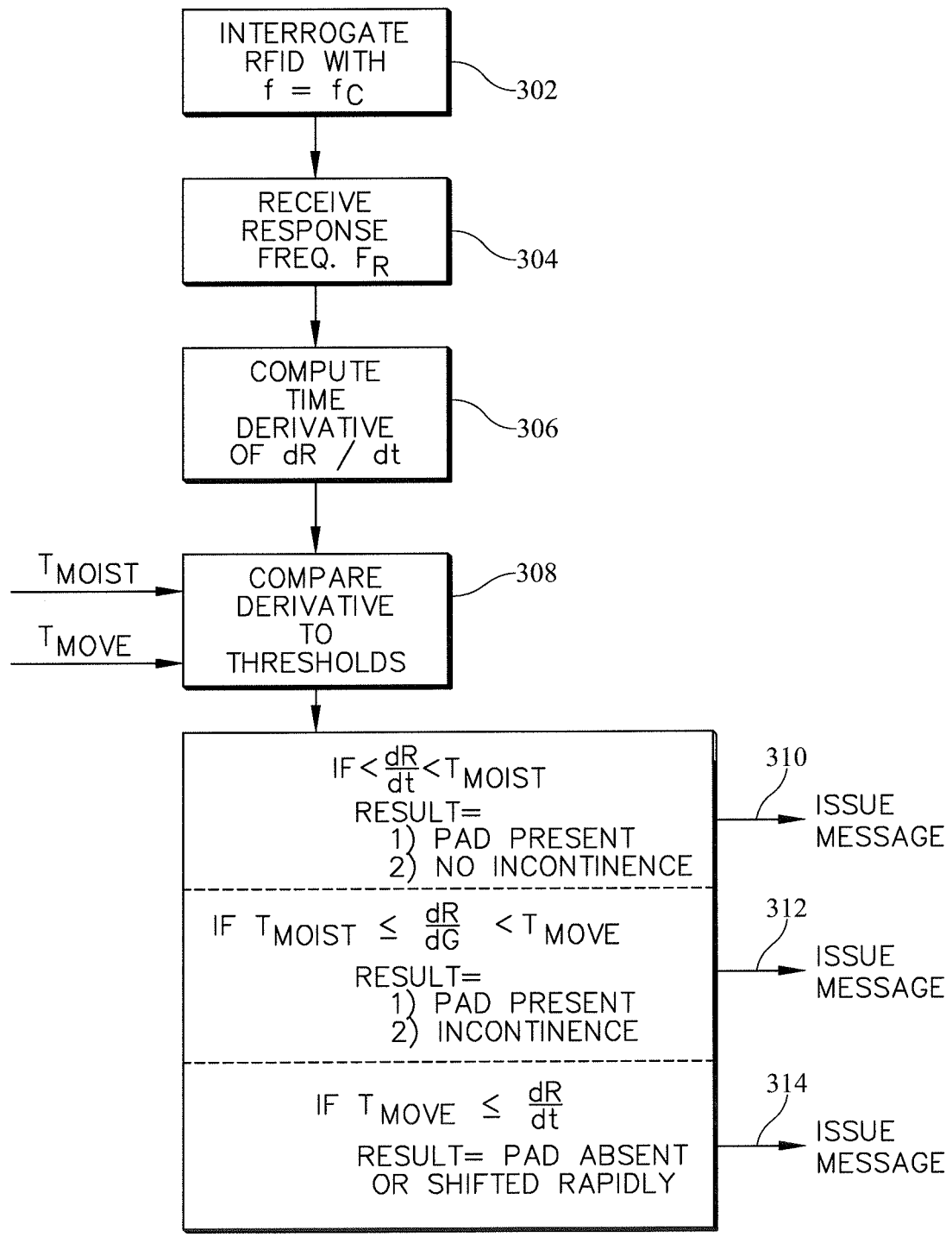
FIG. 4 is a simplified block diagram showing another embodiment of a method of interrogating one or more sensors to detect the presence of moisture on an occupant support.

FIG. 4 shows a related method of interrogating a sensor to detect the presence of moisture on an occupant support. The method may be used with the architecture of FIGS. 1A and 1B. As with the method of FIG. 3 the method includes providing a moisture responsive sensor 104 in a surveillance zone 103A of the occupant support. The sensor is tuned to a center frequency. The method also includes exciting the sensor with an electromagnetic signal having a frequency approximately equal to the center frequency (block 302) as in FIG. 2 and monitoring for and receiving a center frequency response from the sensor (which response may be a null response) (block 304).

The method recognizes that the tuning of the sensor will change as a function of moisture and that the rate at which the tuning changes can indicate the presence or absence of moisture.

Figure 5:
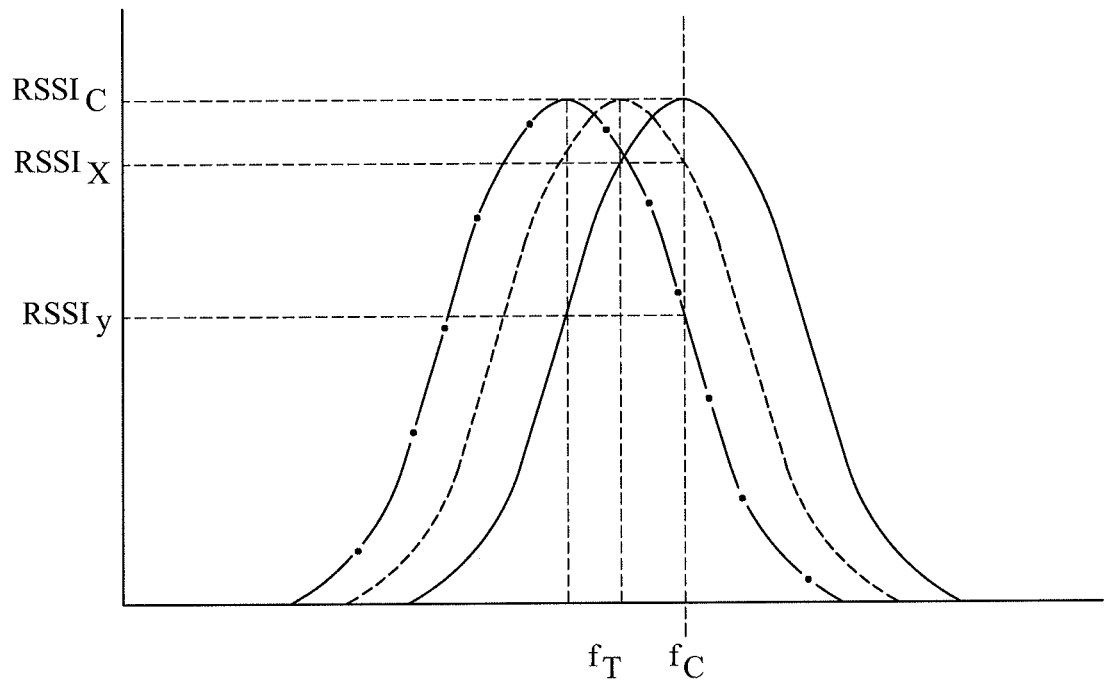
FIGS. 5-7 are simplified illustrations showing two possible ways to calculate a derivative for use in the method of FIG. 4.
Figure 6:
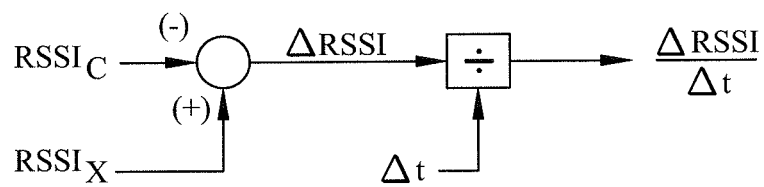
Figure 7:
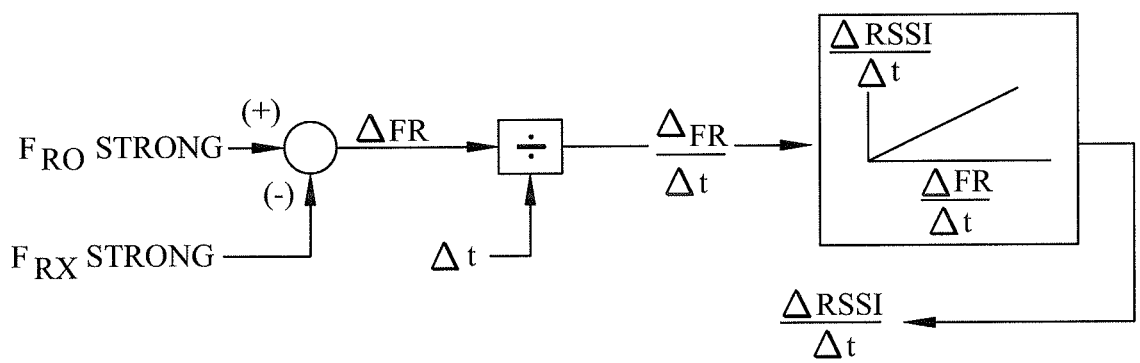

At block 306 the processor calculates a rate of change based on the center frequency responses received at different times. Referring additionally to FIGS. 5-7 two derivative calculations are shown. In FIG. 6 an initial return RSSIC corresponding to an excitation frequency fC is subtracted from a return RSSIX corresponding to an excitation at the same frequency fC applied at a later time. The difference is divided by the time difference delta-t to form a crude derivative dR/dt. The existence of a nonzero derivative (taking measurement tolerances and calculation induced inaccuracies into account) may be the result of the sensors becoming progressively out of tune (i.e. shifting from the solid bell curve to the dashed curve to the dash dot curve of FIG. 5), which yields RSSI's of RSSIC, RSSIX and RSSIY at three different times. FIG. 7 shows an alternate derivative calculation. In the alternate calculation the sensor is interrogated at fC. If the return received by the transceiver 112 changes from strong at one time t0 to weaker at a later time tX, one or more test frequencies not equal to fC are applied at time tX (the time required to apply the one or more additional test frequencies is negligible) until a strong return is again received. The processor uses the information about which excitation frequencies FRO, FRX yielded strong responses, and the time between receiving the strong returns to calculate the derivative dR/dt.

In the method of FIGS. 5-6, the calculated rate of change is a function of a change in RSSI over an interval of time. In the method of FIG. 7 the calculated rate of change is a function of the difference between two excitation frequencies each of which produces a response having approximately equal RSSI values and a correlation describing a relationship between the frequency change and the presence or absence of moisture. Other correlations may enable a determination of the identity or properties of the fluid, e.g. blood, perspiration, acidic fluid, alkaline fluid, and so forth.

Returning now to FIG. 4, the method proceeds to block 308 and compares the calculated derivative to one or more thresholds. In the example shown the derivative is compared to two thresholds Tmoist and Tmove. The processor 120 issues an output in response to the comparison as set forth in TABLE 1 below, in which the rate of change is denoted as dR/dt:

TABLE 1

| Condition | Issued output |
| --- | --- |
| dR/dt < TMOIST | First (310) |
| TMOIST ≤ dR/dt < TMOVE | Second (312) |
| TMOVE ≤ dR/dt | Third (314) |

In the context of detecting incontinence, the first output 310 is an indication that an incontinence pad is present and no incontinence is detected, the second output 312 is an indication that an incontinence pad is present and incontinence has been detected, and the third output 314 is an indication that an incontinence pad is absent.

System for Detecting Incontinence or Other Moisture Caused Abnormality Based on Protected and Exposed Sensors.

Figure 8:
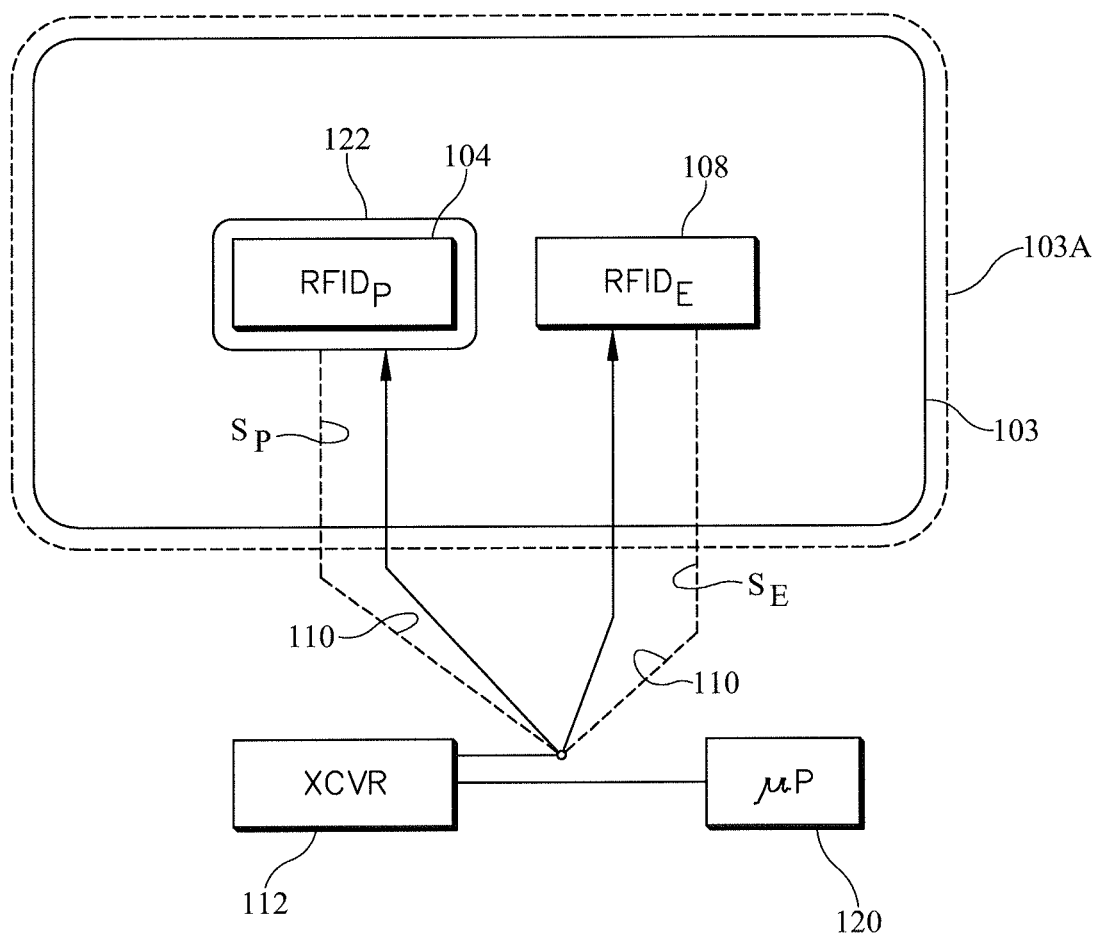
FIG. 8 is a simplified schematic view of an embodiment of a system for detecting the presence of moisture on an occupant support.

FIG. 8 shows a system for detecting the presence of moisture on an occupant support. The system comprises an incontinence pad 103, a transceiver 112 and a microprocessor 120. The pad includes first and second moisture responsive sensors for example RFID's 104, 108 (also labeled RFIDP and RFIDE) in a surveillance zone 103A of an occupant support. Each sensor is tuned to a center frequency. The sensors may be tuned to approximately the same center frequency or to different center frequencies. Sensor RFIDP is enclosed in a moisture proof or moisture resistant enclosure 122 and therefore is also referred to as a protected sensor. Sensor RFIDE is not protected from moisture which may be present on the pad in the surveillance zone and therefore is referred to as an exposed sensor.

Transceiver 112 is adapted to excite each sensor RFIDP, RFIDE with an electromagnetic signal having a frequency approximately equal to its center frequency and to monitor for a center frequency response from each sensor;

Processor 120 is adapted to compare the center frequency response SP of the first (protected) sensor to an expected center frequency response of the first sensor and to compare the center frequency response of the second sensor SE to an expected center frequency response of the second sensor, or equivalently to assess the response as "strong" or as "weak or absent". The processor is further adapted to issue an output as set forth in TABLE 2 below:

TABLE 2

| Result of comparison (response vs. expected response) or assessment for first (protected) sensor | Result of comparison (response vs. expected response) or assessment for second (exposed) sensor | Output |
| --- | --- | --- |
| RSSI strong | RSSI strong | no moisture detected sensor detected |
| RSSI strong | RSSI weak or absent | moisture detected |
| RSSI weak or absent | RSSI strong | fault |
| RSSI weak or absent | RSSI weak or absent | sensor not present or sensor moved or fault |

If the response from both sensors is strong, the sensors, and therefore pad 103, are present but the system is not detecting moisture. Accordingly the output ("no moisture detected") is consistent with that finding. If the response from the protected sensor is strong and the response from the exposed sensor is weak or absent, the mat is present (as revealed by the strong signal from the protected sensor, which, because of enclosure 122, has not suffered any change of tuning as a result of the presence of moisture) and moisture is also present (as revealed by the weak signal from the exposed sensor which has become mistuned as a result of the presence of moisture). Accordingly the output is consistent with that finding ("moisture detected"). If the response from the protected sensor is weak or absent and the response from the exposed sensor is strong it is likely that a fault exists. Accordingly the output is consistent with that finding ("fault"). If the response from both sensors is weak or absent there may be a fault or the mat may have been removed from the occupant support mattress or the position of the pad on the mattress may have changed enough that the sensors are out of range of the transceiver.

Method of Sensor Interrogation for Detecting Incontinence or Other Moisture Caused Abnormality Based on Protected and Exposed Sensors.

Figure 9:
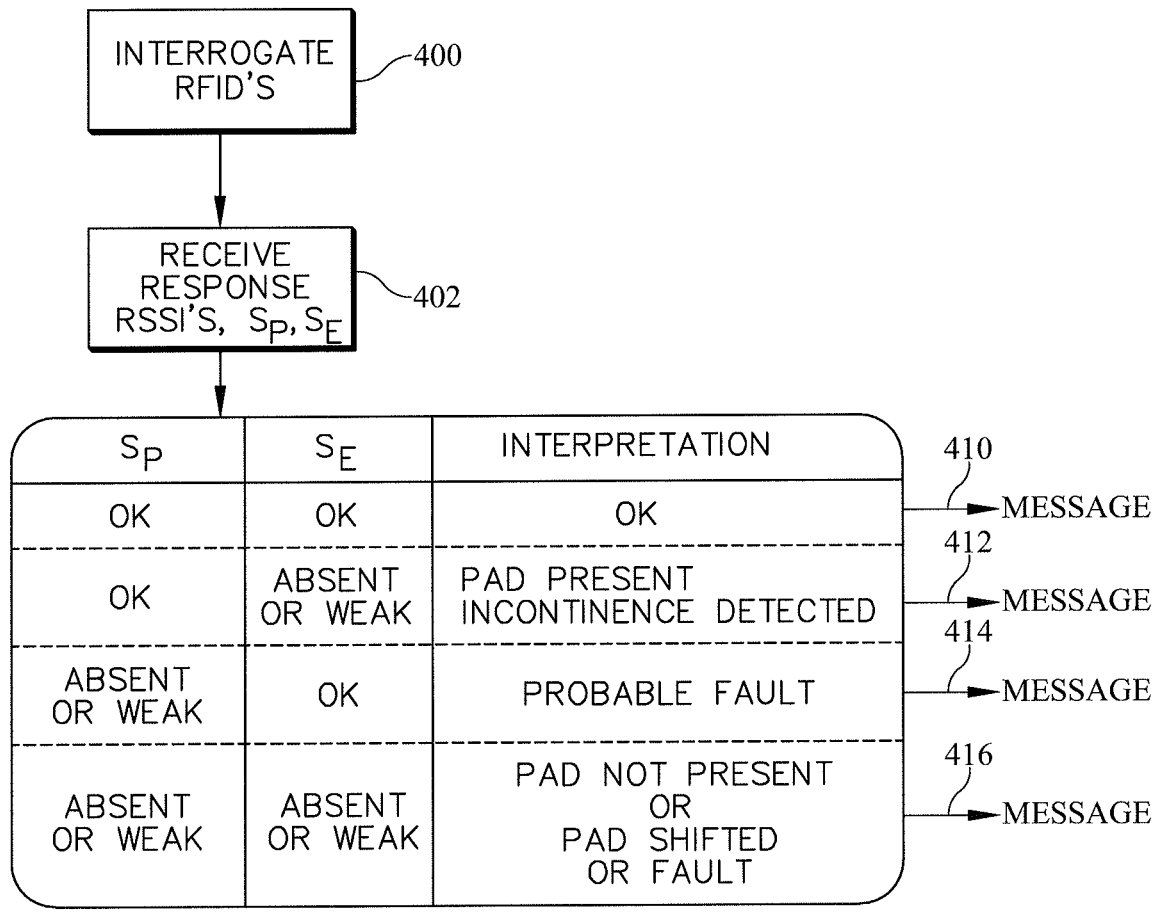
FIG. 9 is a simplified block diagram showing another embodiment of a method of interrogating one or more sensors to detect the presence of moisture on an occupant support.

FIG. 9 is a block diagram showing a method of interrogating a sensor suite (which may be a suite of two sensors as in FIG. 8) to detect the presence of moisture on an occupant support. The method may be used with the architecture of FIG. 8. Referring to FIGS. 8 and 9 the method includes providing first and second moisture responsive sensors 104, 108 in a surveillance zone of the occupant support. The sensors are each tuned to a center frequency. First sensor 104 is protected from coming into contact with moisture which may be present in the surveillance zone. Second sensor 108 exposed and therefore is susceptible to coming into contact with moisture which may be present in the surveillance zone.

The method includes exciting each sensor with an electromagnetic signal having a frequency approximately equal to its center frequency (block 400), monitoring for and receiving a center frequency response signal SP from the first, protected sensor, and monitoring for and receiving a center frequency response signal SE from the second, exposed (unprotected) sensor. As with other embodiments the response may be a null response. The method also includes comparing the center frequency responses to an expected center frequency response for each sensor, or equivalently assessing the response from each sensor as "strong" or as "weak or absent".

The method also includes issuing an output 410, 412, 414, or 416 as set forth in TABLE 3 below:

TABLE 3

| Result of comparison (response vs. expected response) or assessment for first (protected) sensor | Result of comparison (response vs. expected response) or assessment for second (exposed) sensor | Output |
| --- | --- | --- |
| RSSI strong | RSSI strong | no moisture detected sensor detected |
| RSSI strong | RSSI weak or absent | moisture detected |
| RSSI weak or absent | RSSI strong | fault |
| RSSI weak or absent | RSSI weak or absent | sensor not present or sensor moved or fault |

Method of Fluid Analysis.

Figure 10:
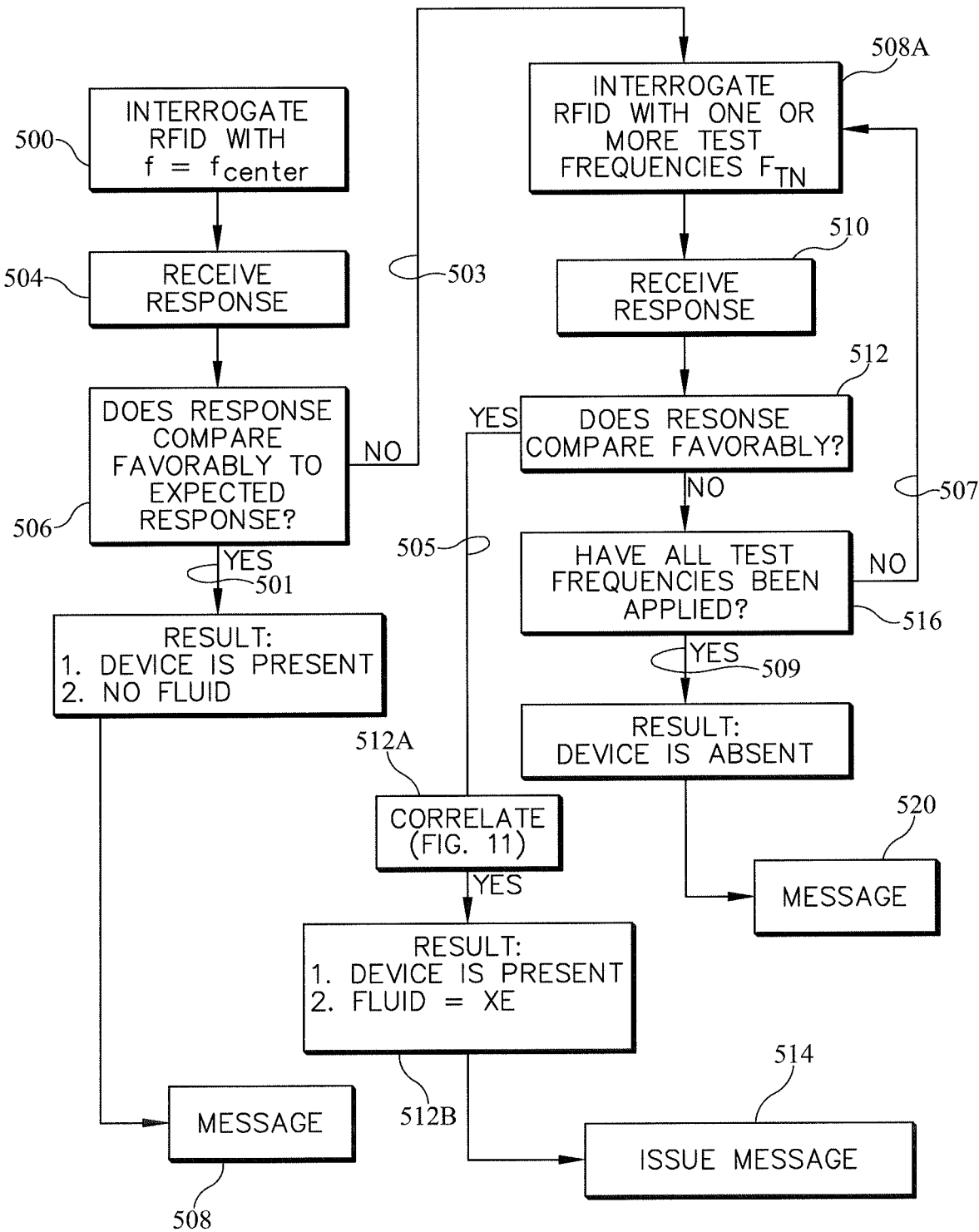
FIG. 10 is a simplified block diagram similar to that of FIG. 2 showing an embodiment of a method of interrogating one or more sensors to detect the presence of moisture on an occupant support and to analyze moisture which may be present.

FIG. 10 is a block diagram similar to that of FIG. 2 showing a method of interrogating a sensor to detect the presence of moisture on an occupant support and to analyze moisture which may be present. The blocks of FIG. 10 which are analogous to those of FIG. 2 are identified with 500-series reference numerals in lieu of the 200-series reference numerals used on FIG. 2.

The method may be used with the architecture of FIGS. 1A and 1B. A moisture responsive sensor 104 is provided in the surveillance zone 103A of the occupant support. The sensor is tuned to a center frequency fC (FIG. 3). At block 500 the sensor is excited with an electromagnetic signal 110 having a frequency approximately equal to the center frequency. At block 504 transceiver 112 monitors for and receives a center frequency response from the sensor. The response may be a strong response or a weak response. The response may also be a "null" response, i.e. a response of no discernible RSSI or other indication of strength. At block 506 microprocessor 120 compares the center frequency response to an expected or desired center frequency response. If the center frequency response at block 506 compares favorably to the expected or desired center frequency response, the method follows path 501 so that the processor issues a first output 508 consistent with the favorable comparison. As seen in the illustration the first output is an indication that a moisture detecting device is present and no moisture or fluid is detected.

If the center frequency response does not compare favorably with the expected center frequency response at block 506, the method follows path 503. At block 508A the processor causes the transceiver to excite the sensor with one or more electromagnetic test signals having test frequencies different than the center frequency. After each excitation the transceiver monitors for a test frequency response at block 510. At block 512 the processor determines if the test frequency response from the sensor compares favorably to an expected test frequency response corresponding to the test frequency. If not, the method proceeds to block 516 where the processor determines if all test frequencies of interest have been applied. If not, the method follows path 507 and applies additional test frequencies (block 508) and continues to monitor for a return (block 510) that compares favorably (block 512).

Upon detecting a test frequency response that compares favorably to an expected test frequency at block 512, the method proceeds along path 505 to block 512A where the method correlates the test frequency response with a relationship between test frequency response and fluid identity, fluid properties or both. FIG. 11 shows a sample correlation for test frequencies higher than and lower than the center frequency fC. As seen in the illustration the correlation relates a strong RSSI return at a specified frequency to the identity and/or properties of a fluid which, as a result of having contaminated the RFID, retunes the RFID to a frequency other than its noncontaminated center frequency, i.e. to the frequency correlated with the fluid or fluid property. The method then issues a second output 514 consistent with the favorable comparison between the test frequency response and the expected test frequency response and also consistent with the correlation. The second output is an indication that a moisture sensing device is present and that moisture has been detected and is also an indication of the identity of the fluid, the type of fluid or both as defined by the relationship between test frequency response and fluid identity, fluid properties or both.

If, at block 516, the method determines that all test frequencies have been applied (block 516) without having received a favorable response (block 512) the method follows path 509 and the processor issues a third output 520 consistent with the unfavorable comparison between all the test frequency responses and their corresponding expected test frequency response. The third output is an indication that a moisture sensing device is absent or a fault has occurred. The conclusion that the device is absent may mean that it has been removed from the mattress, or it may mean that it has been displaced along the mattress far enough that it is out of communication with the transceiver.

As noted above in the context of the architecture of FIGS. 1A and 1B, the second output may be issued in response to an initial favorable comparison at block 512 and without first exciting the sensor at any other test frequencies. Alternatively issuance of the second output may be deferred until at least one additional test frequency has been applied to the sensor or until all test frequencies of interest have been applied to the sensor, even if an earlier applied frequency yields a favorable comparison between the test frequency response and the expected or desired response at that test frequency. That is, the second output is not issued until the sensor has been excited at at least one frequency other than the test frequency that yielded the initial favorable comparison. This latter method may require a correlation that goes beyond the one dimensional correlation of FIG. 11 in order that processor 120 may properly interpret the significance of multiple strong RSSI returns.

System for Detecting Incontinence or Other Moisture Caused Abnormality Using Multiple RFID's or Other Sensors or Using Multiplexed RFID's or Other Sensors.

Figure 12:
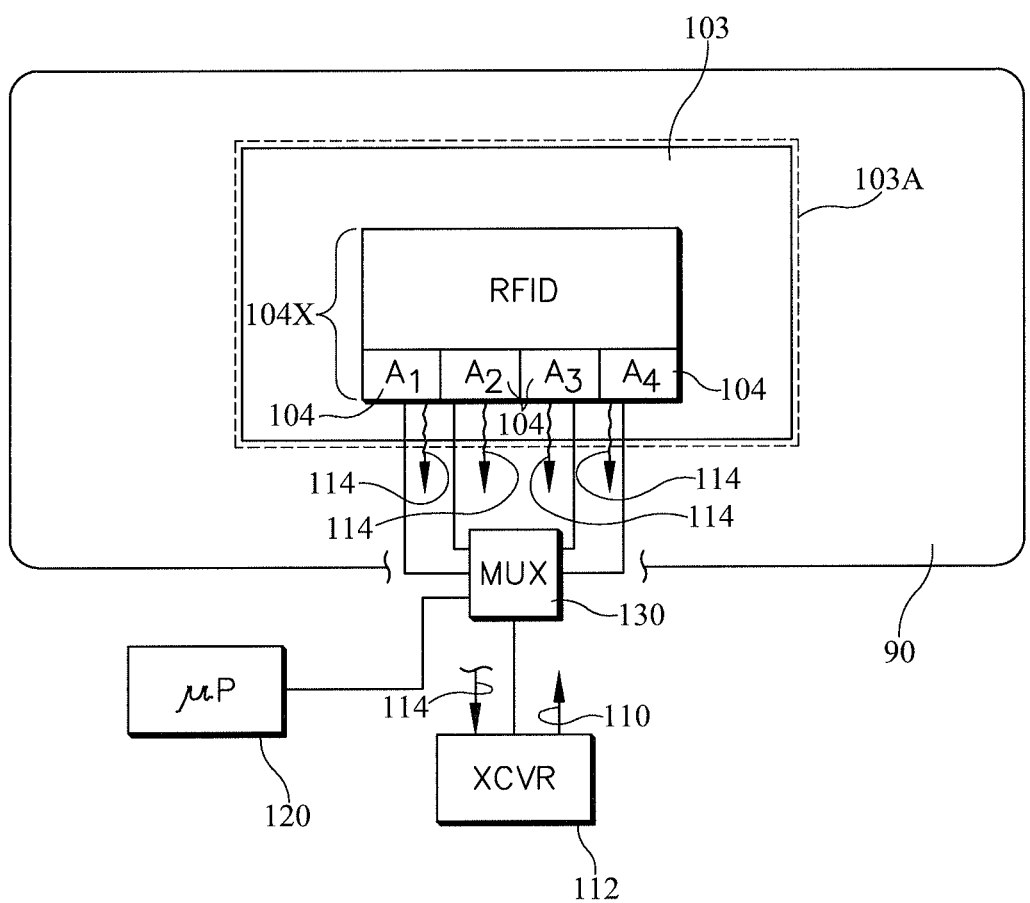
FIG. 12 is a simplified schematic view of an embodiment of a system for detecting the presence of moisture on an occupant support or for detecting the displacement of one or more sensors, or both.

FIG. 12 shows a system for detecting the presence of moisture on an occupant support or displacement of a sensor or both. The system includes multiple moisture responsive sensors 104 spatially distributed in a surveillance 103A zone of an occupant support 90. In the illustrated embodiment sensors 104 are individual antenna components (A1, A2, A3, A4) of an RFID sensor assembly 104X. Illustratively, each sensor is at least initially tuned to a center frequency. The system also includes a transceiver 112 adapted to excite the sensors with an electromagnetic signal 110 having a frequency approximately equal to the center frequency and to monitor for a center frequency response 114 from the sensor. The system also includes a multiplexer 130, in communication with each antenna and with the transceiver. The system also includes a processor 120 adapted to command the transceiver 112 to excite the sensors and to analyze the center frequency response of each sensor to detect the presence of moisture on the occupant support or displacement of a sensor or both. The processor 120 is also in communication with the multiplexer 130 so that the processor can govern which of the responses 114 the transceiver 112 detects at any given time. For example the multiplexer 130 may cycle from sensor antenna A1 to sensor antenna A2 to sensor antenna A3 to sensor antenna A4 and then continue repeating the cycle so that the transceiver 112 first detects return signal 114 from A1, then return signal 114 from A2, and so forth.

As already noted the illustrative sensors 104 are individual antenna components A1, A2, A3, A4 of a sensor assembly 104X. The processor is adapted to command multiplexer 130 to acquire response signals from each antenna component. The illustration shows only a single sensor assembly 104X, however more than one such assembly may be used.

Figure 13:
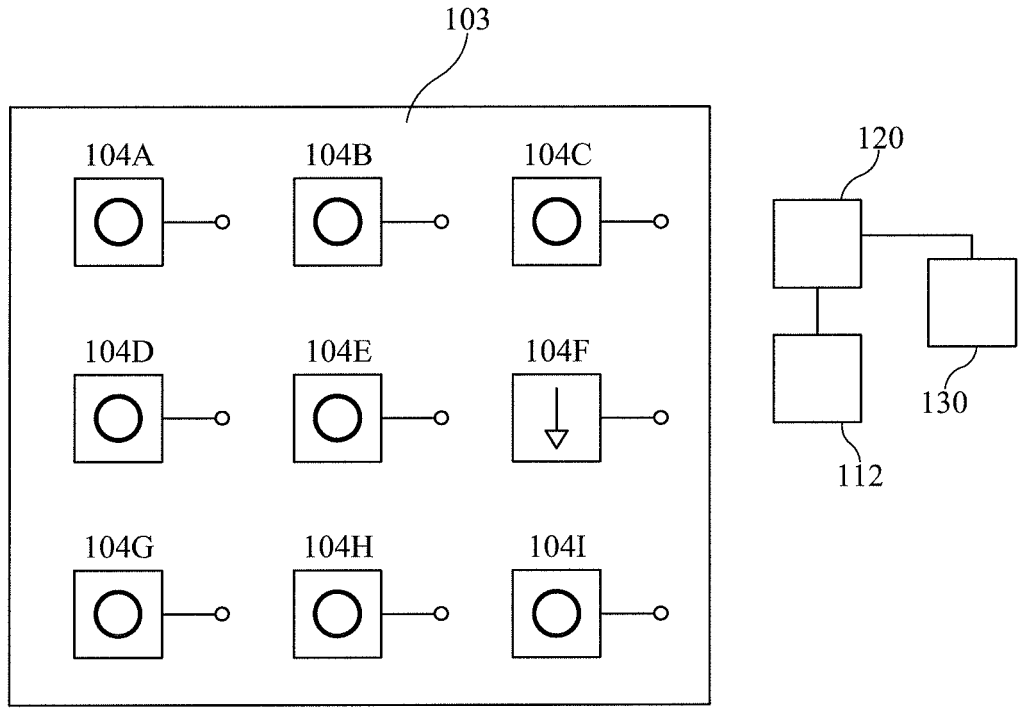
FIGS. 13-14 are simplified schematic plan views each showing an embodiment of a sensor array and an example response to the presence of moisture in contact with at least one of the individual sensors.
Figure 14:
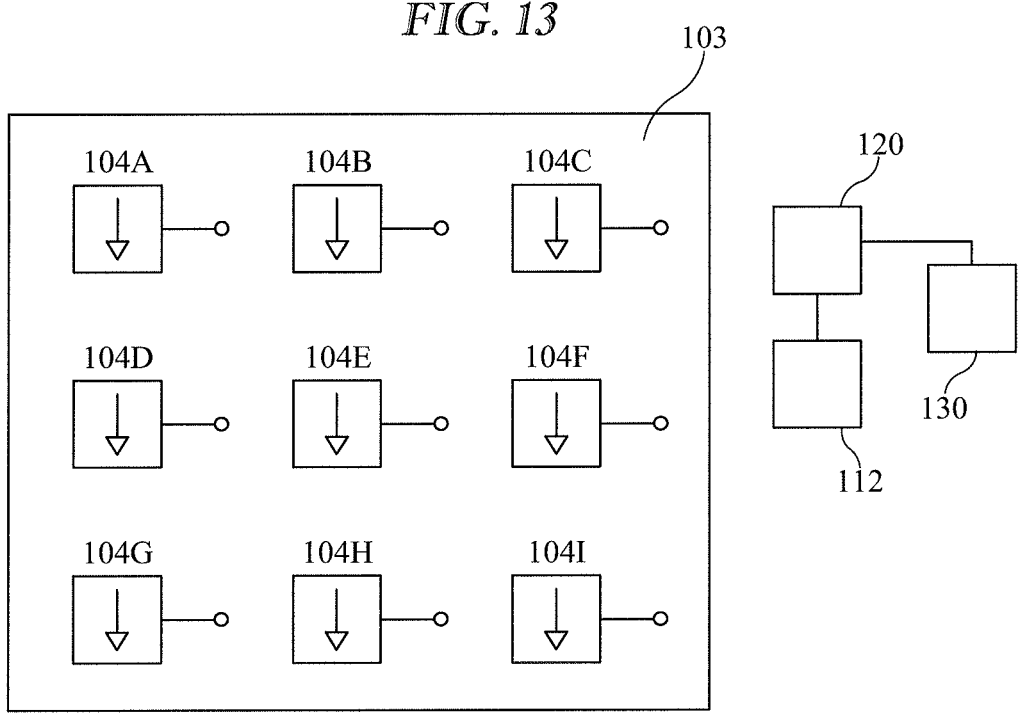

Alternatively the sensors 104 may be individual sensors such as RFID 104 of FIGS. 1A and 1B or RFID's 104A through 104I of FIGS. 13-14, each of which individual sensors has its own antenna A. Processor 130 is adapted to command multiplexer 130 to acquire response signals from each antenna component, e.g. in a successive sequence.

A system may contain one or more assemblies 104X each having two or more antenna components or may have multiple sensors 104 each having its own antenna. Or a system may use a mix of assemblies 104X and individual sensors 104. For example, each or any surveillance zone of the occupant support may contain one or more sensors, where each sensor is coupled to an antenna, or the sensors and/or antennas may be located in multiple different zones. Further, within a single zone or across different zones, the sensors 104 may be disposed according to different spatial arrangements. For example, a single zone may be configured with two sensors each disposed at opposite edges of the zone (e.g., spaced apart from one another by a width or a length of the occupant support) but disposed at different (e.g., vertical) distances from the occupant support or the bottom of the pad 103. Alternatively or in addition, the sensors may be disposed at different locations with respect to the length or the width of the pad 103 or the occupant support. For instance, a zone of the occupant support may contain two sensors that are located on opposite lateral sides of the pad 103 but which are not collinear (e.g., so that one sensor is disposed a first distance from an end of the pad 103; while the other sensor is disposed a second, different distance, from the same end of the pad 103). Of course, any zone may be configured with only one sensor. No matter which option is employed, electrical circuitry, e.g., a processor 130, is adapted to command the multiplexer to acquire response signals from all the antennas present whether the antennas are components of a multi-antenna assembly (components 104 of assembly 104X as in FIG. 14) or are dedicated antennas (antennas 104 or A as in FIG. 13). The processor is also adapted to command the transceiver to analyze the frequency response of each sensor to detect the presence of moisture on the occupant support or displacement of a sensor or both.

Method for Detecting Incontinence or Other Moisture Caused Abnormality Using Multiple RFID's or Other Sensors or Using Multiplexed RFID's or Other Sensors and Based on Highest Return Signal Strength.

Figure 15:
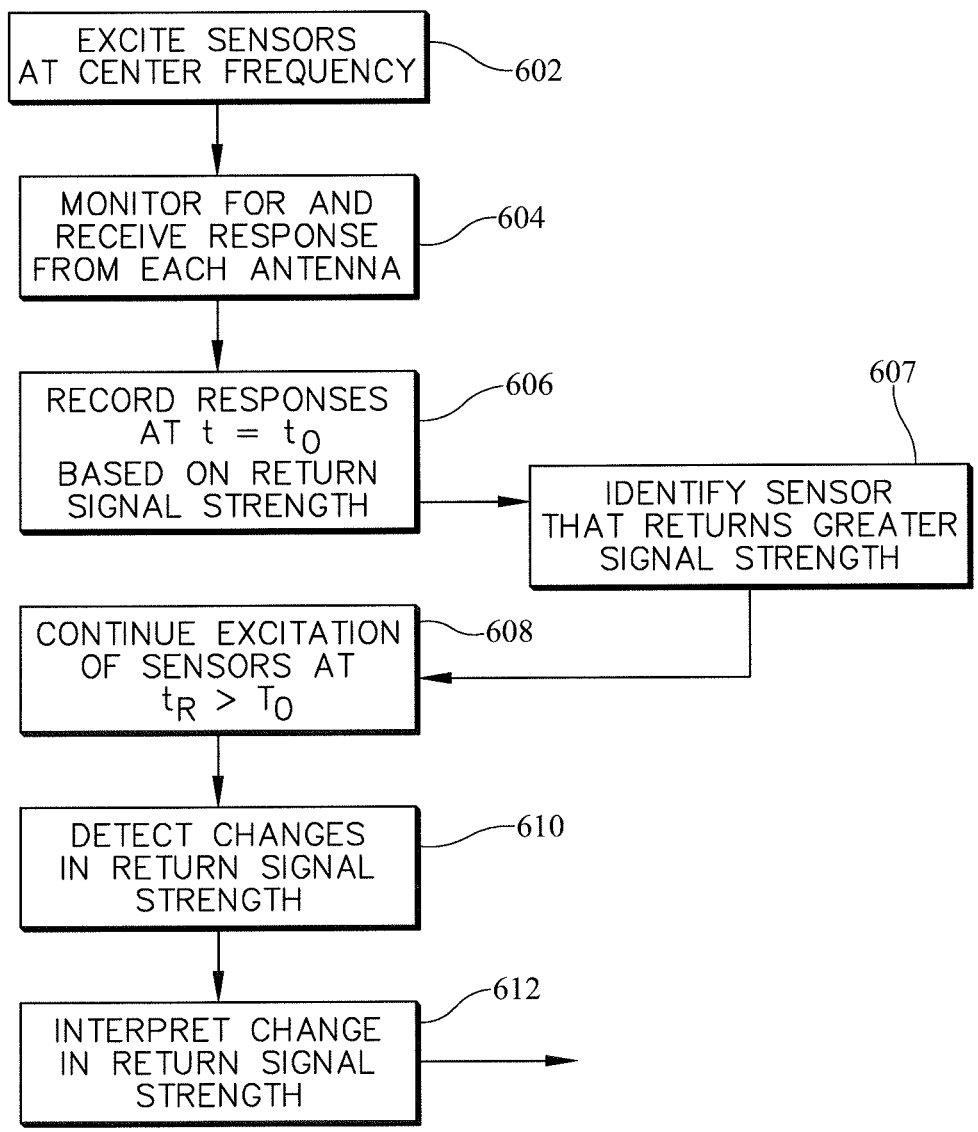
FIG. 15 is a simplified block diagram showing an embodiment of a method of detecting the presence of moisture on an occupant support and distinguishing between moisture presence and sensor displacement relative to some initial sensor position.

FIG. 15 is a block diagram showing a method of detecting the presence of moisture on an occupant support and of distinguishing between moisture presence and sensor displacement relative to some initial sensor position. The method may be used with the system architecture of FIGS. 12-14. The method includes providing two or more moisture responsive sensors 104 in a surveillance zone 103A of the occupant support. Each sensor is tuned to a center frequency fC. Transceiver 112 excites the sensors with an electromagnetic signal 110 having a frequency approximately equal to the center frequency (block 602). The transceiver receives center frequency responses from the sensors at a time t0 (block 604). As previously noted the time required for multiplexer 130 to cycle through the sensors is much shorter than any time interval of interest associated with detecting an incontinence event or detecting sensor displacement. Accordingly, any given sampling cycle which occurs between time t−δ and time t+δ is considered to have occurred at time t. The processor identifies which of the sensor returns 114 at time t0 is strongest (block 607). At times t>t0 (blocks 608 and beyond) the transceiver continues to excite at least the identified sensor (and may excite additional sensors as well) (block 608) and receives responses (block 610). The processor carries out an analysis to determine if the return signal strength of the identified sensor has diminished over time. If so the processor analyzes the center frequency return signal strengths from the excitation at time t0 in comparison to the responses obtained as a result of the continuing excitation to detect moisture presence or sensor displacement or both (block 612).

Method for Detecting Incontinence or Other Moisture Caused Abnormality Using Multiple RFID's or Other Sensors or Using Multiplexed RFID's or Other Sensors.

Figure 16:
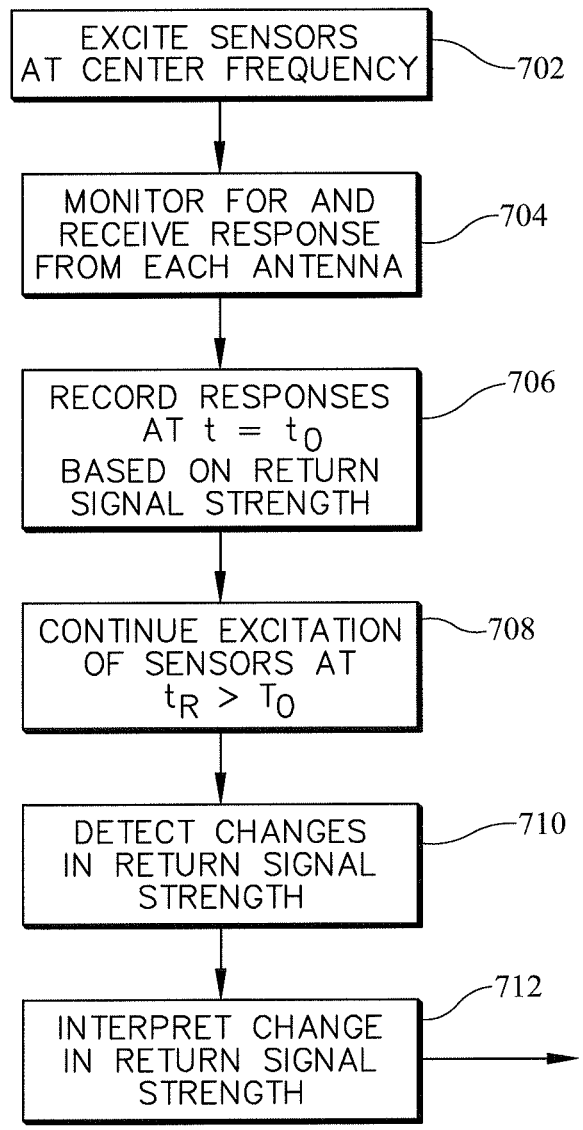
FIG. 16 is a simplified block diagram showing another embodiment of a method of detecting the presence of moisture on an occupant support, detecting displacement of a moisture sensor or both.

FIG. 16 shows another method of detecting the presence of moisture on an occupant support, displacement of a moisture sensor or both. The method includes providing two or more moisture responsive sensors in a surveillance zone of the occupant support, which sensors are tuned to a center frequency. The method may be used with the system architecture of FIGS. 12-14. Transceiver 112 excites the sensors with an electromagnetic signal 110 having a frequency approximately equal to the center frequency (block 702). Transceiver 112 receives center frequency responses from the sensors (block 704) and records the individual center frequency responses at a time t=0 (block 706). At times t>0 transceiver 112 continues to excite the sensors and to monitor for and receive responses (block 608). At block 710 the processor detects changes in return signal strength, i.e. the differences at times t>0 relative to time t0. At block 712 the processor analyzes the differences determined at block 710 to discern moisture presence, sensor displacement or both. As noted in the discussion of FIGS. 12-14 the sensors may be individual sensors each coupled to an antenna or may be individual antenna components of a sensor assembly.

FIGS. 13-14 show two examples, both of which rely on a 3×3 array of sensors labeled 104A through 104I. The symbols within each sensor show how that sensor's return frequency response signal (RSSI) has changed between time t0 and a later time. The "0" symbol indicates no change while the downwardly pointing arrow symbols indicate a decrease in return signal strength. In FIG. 13 fewer than all of the sensors exhibit a diminished signal strength (RSSI) and the remainder of the sensors exhibit constant return signal strength. Analysis at block 712 of FIG. 16 therefore reveals that the sensor pad 103 is still in place in its original (t=t0) position but that the sensors exhibiting reduced strength have been contaminated with moisture. This conclusion is based on the observation that the center frequency response from a first set of one or more sensors (sensor 104F) has become weaker at a time t>0 relative to its center frequency response at an earlier time t0, and that the response of a second set of sensors (all but 104F) which does not include members of the first set (104F) have substantially the same response strength at time t>0 than they did at the earlier time t0.

In FIG. 14 the sensors all exhibit reduced return strength relative to strength at t=0. Hence, the sensors are still in their original location, or have all become moist, or some combination of the two. Distinguishing between the two possibilities or determining that both have occurred can rely on techniques such as those described in the context of FIGS. 2-9. In one embodiment sensor displacement is declared as a result of the center frequency response from all or substantially all the sensors having become weaker at a time t>0 relative to their center frequency response at an earlier time t0. In other embodiments, changes in the sensor's response over time (e.g., comparisons to earlier-received sensor responses), or changes in the difference between the sensor's response and the expected response, may be used to determine sensor displacement.

Hybrid Incontinence Detection System.

Figure 17:
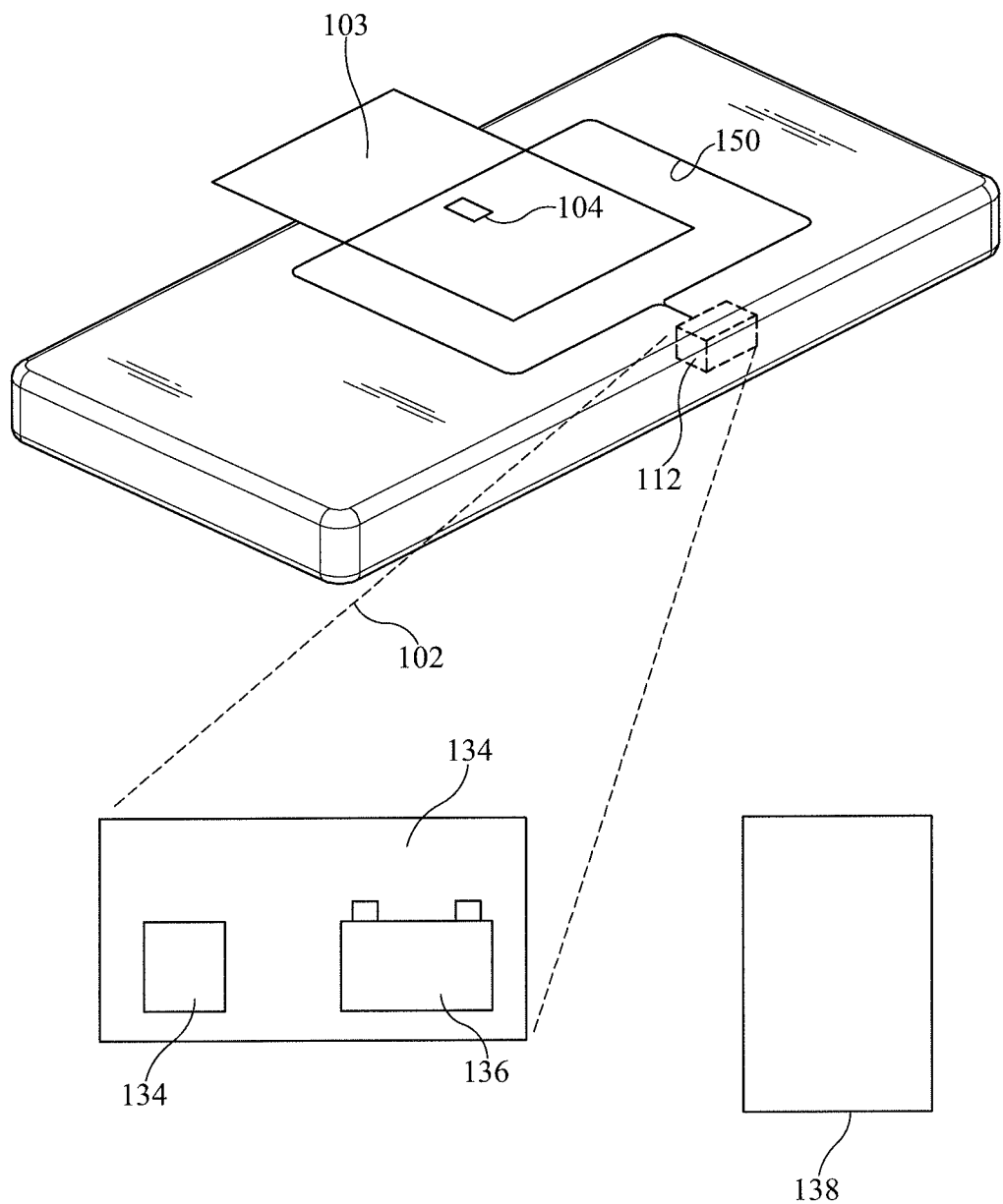
FIG. 17 is a simplified diagram of an embodiment of a system in which a transceiver for exciting an RFID tag is integrated into an occupant support.

FIG. 17 shows a system in which the transceiver is integrated into an occupant support. If the occupant support is a bed the transceiver may be integrated into the frame (not shown) or into the mattress 102. The system includes a sensor 104 such as an active or passive RFID tag. Alternatively the sensor may be a circuit printed on a paper. The sensor, irrespective of the technology on which it is based, may be in the form of a sticker. The sensor is made a part of a pad such as incontinence pad 103, for example by sewing or adhering. For example if the sensor is a sticker it may be adhered to the pad at a suitable location, which may be inside of or in the interior of the pad rather than on the surface of the pad. At least the sensor is disposable. The pad may also be disposable.

The system also includes a transceiver 112, which may be integrated with the bed, for example with the mattress 102. In some embodiments, the transceiver 112 is not considered to be disposable. The system may be referred to as a hybrid system because it includes disposable and nondisposable components. In some embodiments, the nondisposable component (e.g., the transceiver 112) is integrated into the occupant support whereas the pad and sensor are easily disassociated from the occupant support. In other embodiments, the transceiver 112 may be spaced apart from the occupant support. For example, the transceiver may be placed at any convenient location within the patient's environment, such as on a chair, in a mattress, in a headwall or support column, on the patient's clothing or body, etc.

The sensor is in wireless communication with the reusable transceiver 112. The illustrative transceiver 112 includes electrical circuitry, such as a processor chip 134 and may also include a battery 136. In one embodiment the battery 136 is a flexible or foldable battery.

The transceiver 112 is also in wired or wireless communication with a facility information network 138 to provide for information exchange between the transceiver and the facility network. In one example the communication with network 138 enables an alert to be sent to caregivers to alert them of the incontinence event (or other moisture containing contamination). In another example the communication can also enable updates to be made to electronic records. Such alerts and updates may be configured based on one or more characteristics or preferences of a patient or caregiver. The alerts and updates can be communicated (e.g., by the transceiver 112 and the network 138) to one or more notification devices, such as bed-mounted visual indicators (e.g., a SafeView® light, which is a feature of certain products of the Hill-Rom Company, Inc.), nurse's stations, mobile communication devices, flat-screen monitors, dome lights, electronic status boards, and/or other devices that are capable of displaying or otherwise presenting notifications and updates to caregivers and/or recipients of that information.

In one embodiment a transceiver antenna 150 loops around sensor 104. The antenna may be integral with the mattress or with a ticking or other cover on the mattress. One example of an integral antenna construction is an antenna made of metal thread which is woven or otherwise integrated into the mattress. Another example is a conductive ink applied to the ticking or mattress. Yet another example is conductive fabric.

Fluid Reservoir (Absorbent or Dissolving)

FIGS. 18-23 show variants of an architecture for a moisture detection article or pad 103 such as an incontinence pad. The pads include at least one sensor 104 such as an RFID tag. The following discussion of the various embodiments of FIGS. 18-23 relates to the architecture or construction of the pad. The RFID tag or tags can be used for moisture detection and/or analysis as described elsewhere in this specification. Further, it should be noted that while the sensor 104 is described with reference to some embodiments as a component of the architecture of the pad 103, in other embodiments, the sensor 104 may be embodied as a separate component that can be installed in a pad, either during manufacture of the pad or at a later time. For instance, the sensor 104 may be mounted to a substrate to form a "sensor sheet" as described further below, and one or more sensor sheets may then be incorporated into a moisture-absorbent pad or other similar product.

Figure 18:
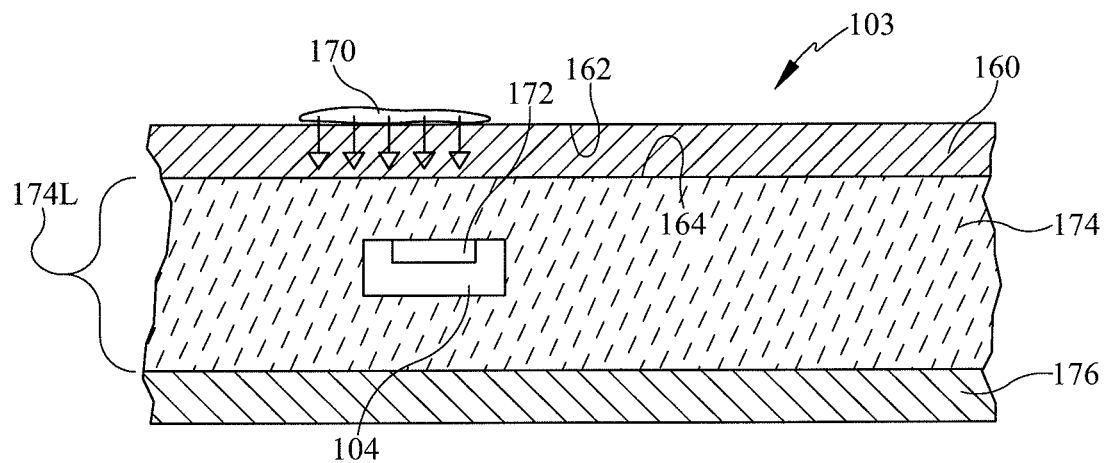
FIGS. 18-23, including

Referring first to FIG. 18 the moisture detection apparatus 103 includes a deposition or receptor layer 160 having an exposed side 162 susceptible to moisture contamination and a nonexposed side 164. The deposition or receptor layer is so named because it is the layer of the construction upon which, in customary use, fluid will be deposited or received. The illustration also shows a region or site 170 of actual fluid contamination or deposition.

The apparatus also includes a moisture sensor 104 having a moisture responsive element 172 separated from the deposition layer by a reservoir material 174. The reservoir material is so named because, as will be explained in greater detail below, its capacity to store a volume of fluid introduces an intentional time delay between the initial deposition of fluid on exposed side 162 and contact between the fluid and the moisture responsive element 172. The volume storage capacity helps prevent false alarms or oversensitivity that might otherwise be triggered by inconsequential amounts of fluid. In the embodiments of FIGS. 19-22 the reservoir material is adjacent to the nonexposed side 164 of deposition layer 160 as distinct from being adjacent to the exposed side 162. The apparatus may also include a base layer 176. At least a portion of the base layer is spaced from the deposition layer such that the reservoir material 174 is between the base layer and the deposition layer. Moisture 170 deposited on exposed side 162 must traverse or otherwise overcome the reservoir material in order to come into contact with the moisture responsive element 172. Moisture deposited on exposed side 162 is impeded (by the reservoir layer) from contacting the moisture responsive element 170 until the reservoir layer reacts to the presence of the moisture. As used herein, "reacts" is used in the sense of responding and does not necessarily mean a chemical reaction, but can mean a chemical reaction.

Figure 19:
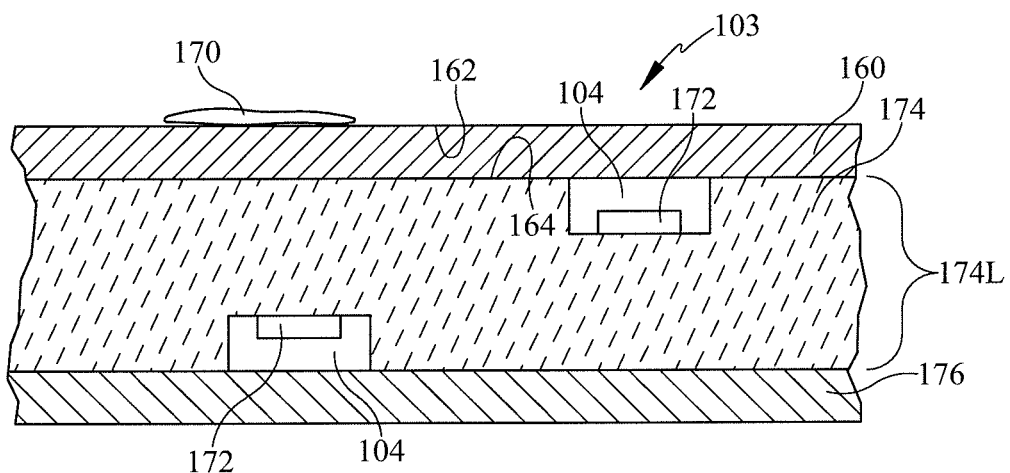
Figure 22:
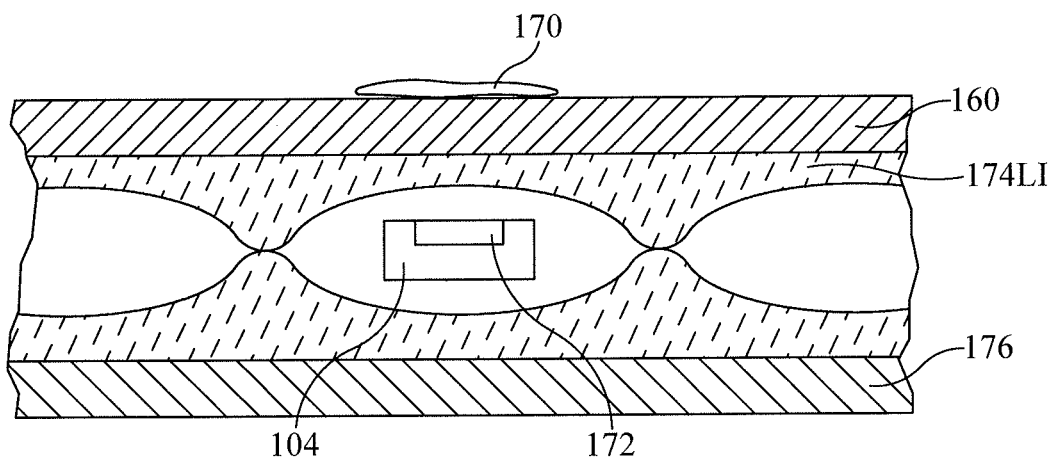
Figure 23:
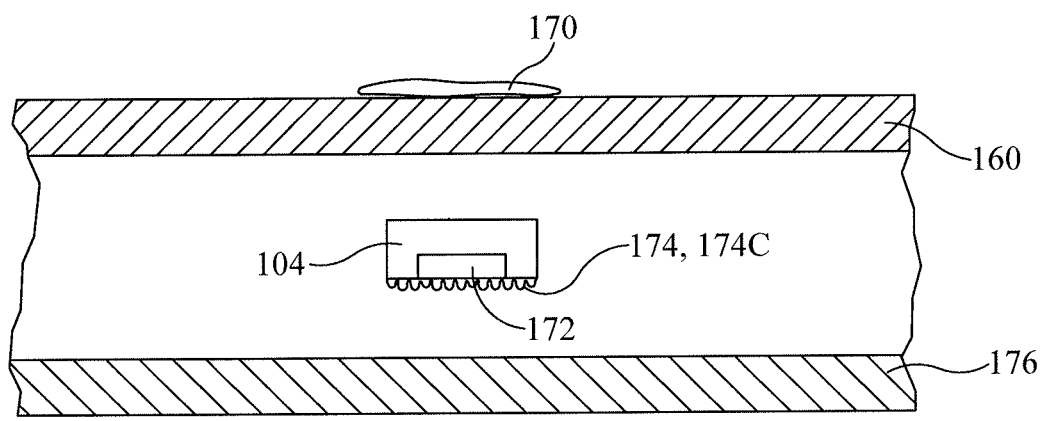

In the variants of FIGS. 18 and 19 the reservoir material is a reservoir layer 174L and the sensor 104 resides within the reservoir layer. The reservoir layer extends between base layer 176 and deposition layer 160. In the variants of FIGS. 18, 20, 21 and 22 the moisture responsive element 172 faces toward the deposition layer. In FIG. 23 the moisture responsive element faces toward the base layer. FIG. 19 shows two sensors, one having a moisture responsive element that faces toward the deposition layer and one having a moisture responsive element that faces toward the base layer. Any particular variant of the architecture may have moisture responsive elements that all face toward the deposition layer or may have moisture responsive elements that all face toward the base layer or may have an assortment of moisture responsive elements some of which face toward the deposition layer and some of which face toward the base layer.

Figures 20, 21:
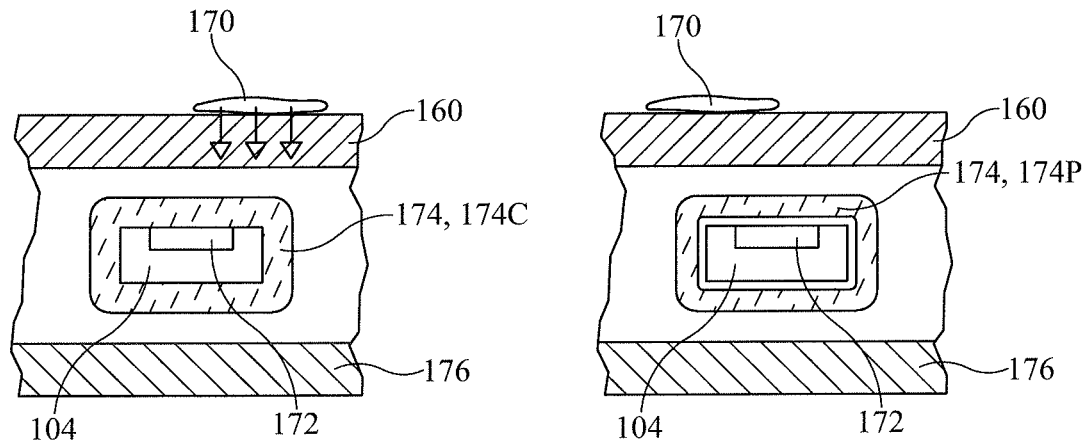

In the variant of FIG. 20 the reservoir material 174 is a coating 174C which encapsulates the sensor 104. In the variant of FIG. 21 the reservoir material 174 is in the form of a pocket 174P which encapsulates the sensor 104. In the embodiments of FIGS. 20-21 (and 23) the reservoir material is considered to be localized whereas in the embodiments of FIGS. 18-19 (and 22) the reservoir material is nonlocalized.

Figure 22A:
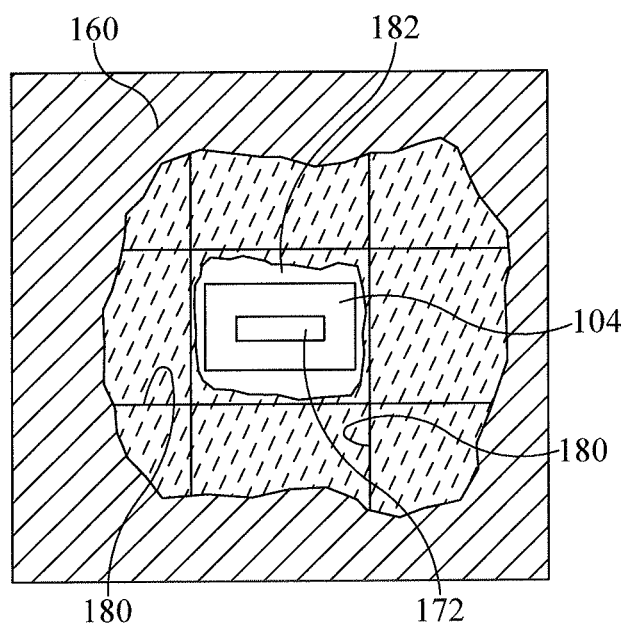
FIG. 22A, are simplified schematic side elevation views showing variants of an embodiment of an architecture for a moisture detection article or pad such as an incontinence pad.

In the embodiments of FIGS. 20 and 23 the reservoir material is a coating over at least the moisture responsive element 172. In FIG. 20 the reservoir material is a coating over the entire sensor 104. In FIG. 23 the reservoir material is a coating that extends only slightly beyond the moisture responsive element. In the embodiment of FIGS. 22 and 22A the reservoir material 174 is a lining 174LI. In the specific embodiment illustrated, lining 174LI also lines base layer 176, and the lining is pinched together at pinch lines 180 to form one or more capsules 182. Sensor 104 resides within the capsule.

In some embodiments the reservoir material may be an absorbent material which, because of its capacity to store a volume of fluid, retards migration of fluid from the fluid deposition site 170 to the sensor element. The volume storage capacity helps prevent false alarms or oversensitivity that might otherwise be triggered by inconsequential amounts of fluid. Examples of such materials include woven textiles. The porosity of the finished textile can be affected by controlling the parameters of the weaving process during manufacture of the woven textile. Affecting the porosity affects the absorbency of the material. As a result the designer of the moisture detection apparatus can regulate the time lapse between deposition of moisture on the deposition layer 160 and contact between the moisture and moisture responsive element 172. The absorption characteristics of the material 174 also can be used to ensure that the moisture comes into contact with the moisture responsive element 172 only if at least a minimum quantity of moisture is present. That is, a "small" amount of moisture would be completely absorbed by and stored in the material 174 without the moisture being able to migrate the entire distance between deposition site 170 and moisture responsive element 172. By contrast, at least some of a "large" quantity of moisture would be able to migrate the entire distance between deposition site 170 and moisture responsive element 172.

Specific examples of materials from which the absorbent reservoir material may be made include polyester, cotton and polyamide materials. In some embodiments the reservoir material 174 may be a material which initially acts as a barrier but then dissolves when exposed to moisture in order to retard migration of the moisture from the fluid deposition site 170 to the moisture responsive element 172 until dissolution of the material is complete enough to expose the moisture responsive element to the fluid. An example of such a material is a polymer with the chemical formula: $-(CH_2-CHOR)_n-$ where R is $-H$ or $-COCH_3$. The foregoing chemical formula is the formula for one type of polymer known as polyvinyl alcohol which is also referred to as PVA or PVOH.

The dissolution characteristics of the dissolvable material 174 enables the designer of the moisture detection apparatus to regulate the time lapse between deposition of moisture on the deposition layer 160 and contact between the moisture and moisture responsive element 172. For example a material that dissolves quickly will shorten the time lapse whereas a material that dissolves slowly will lengthen the time lapse. The dissolution characteristics of the material 174 also can be used to ensure that the moisture comes into contact with the moisture responsive element 172 only if at least a minimum quantity of moisture is present. That is, a "small" amount of moisture may be insufficient to dissolve enough of the material 174 to expose moisture responsive element to the moisture. By contrast, a "large" quantity of moisture would be able to effect sufficient dissolution and come into contact with moisture responsive element 172.

Directional Architecture—Capillary.

Figure 24:
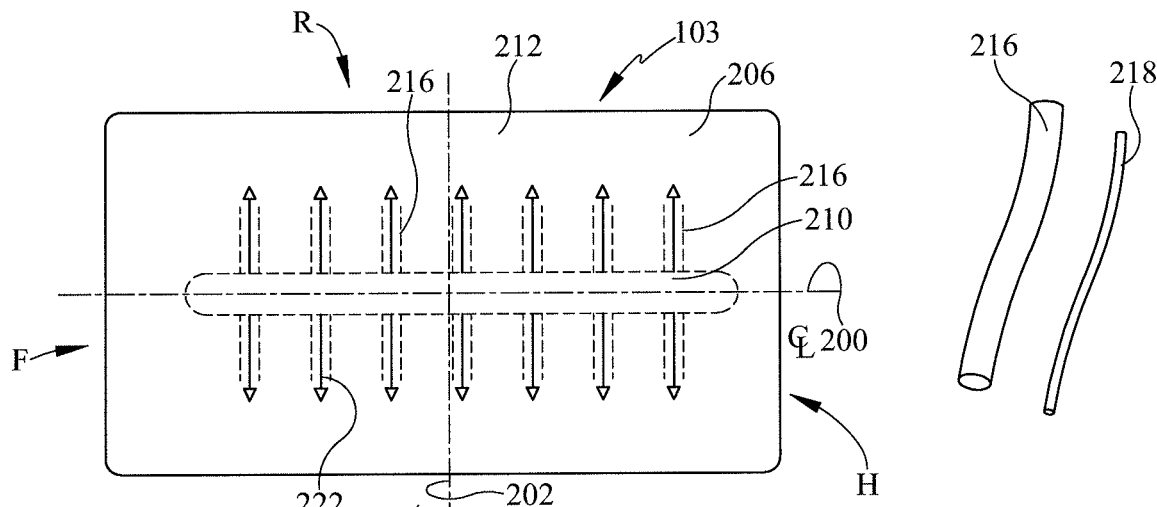
FIGS. 24-26 are simplified depictions of variants of an embodiment of an architecture for a moisture handling apparatus, which may be an incontinence pad, in which a capillary property directs moisture from a source to a destination.
Figure 25:
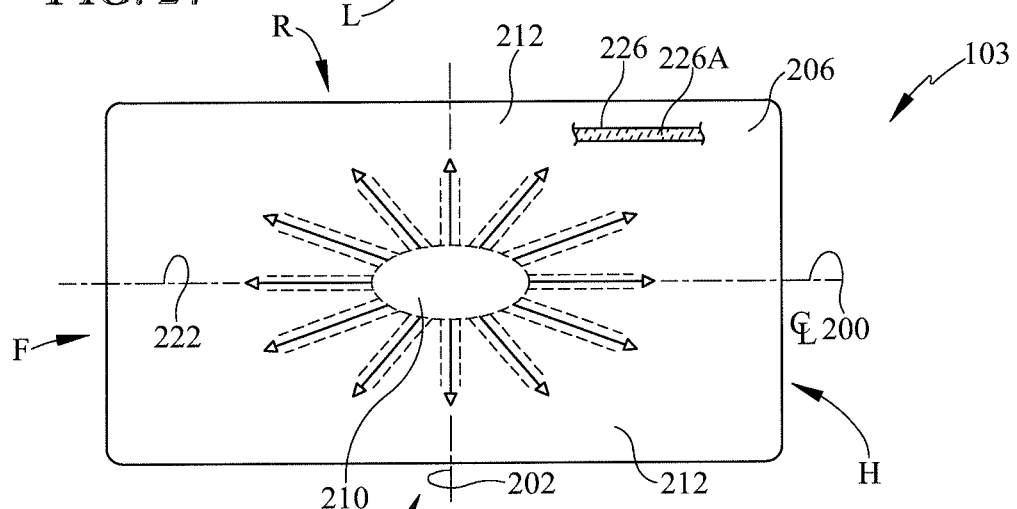
Figure 26:
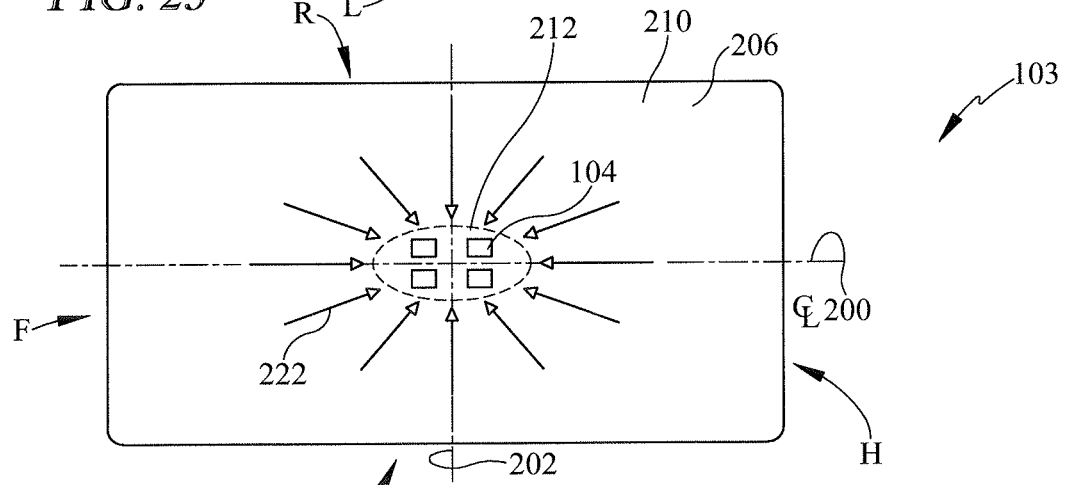

FIGS. 24-26 show variants of an architecture for a moisture handling apparatus, which may be an incontinence pad. The illustrations illustrate a pad-like apparatus having a head end H, a foot end F longitudinally spaced from the head end, a left side L and right side R laterally spaced from the left side. The illustrations also show longitudinally and laterally extending centerlines 200, 202. The apparatus comprises a sheet 206 of material having a capillary property for encouraging moisture migration from a source zone 210 to a destination zone 212. The sheet of material 206 may be located within an interior region of an incontinence pad or diaper, in some embodiments. As seen in FIG. 24 the capillary property may be imparted to the apparatus by capillary tubes 216, or by capillary fibers 218. The tubes 216 or fibers 218 are spatially arranged or oriented, and therefore the capillary property is spatially arranged or oriented, so as to encourage moisture migration from source zone 210 to destination zone 212.

In the example embodiment of FIG. 24 the source zone 210 is an inboard zone (within dashed lines) whose longitudinal dimension substantially exceeds its lateral dimension. Zone 210 is approximately laterally centered on centerline 200. Destination zone 212 is the outboard perimetral region between the point of fluid flow arrows 222 and the lateral edges of the pad. Alternatively the destination zone may be any zone of the apparatus outside the source zone. As used herein the term "inboard" refers to locations relatively remote from the edges of the bed whereas "outboard" refers to locations relatively closer to the edges of the bed. The capillary property is arranged to define one or more capillary pathways (suggested by the fluid flow arrows) extending substantially exclusively laterally from the source zone to the destination zone. Each flow arrow may be considered to represent a capillary pathway. Alternatively all the flow arrows extending in either the left or right direction may be considered to be a single pathway. Alternatively all the flow arrows extending all directions may be considered to be a single pathway.

In the embodiment of FIG. 25 the source zone 210 is an oval shaped inboard zone (within dashed lines) Destination zone 212 is the outboard perimetral region between the point of fluid flow arrows 222 and the lateral edges of the pad. Alternatively the destination zone may be any zone of the apparatus outside the source zone. The capillary property is arranged to define one or more capillary pathways extending both laterally and longitudinally from the source zone to the destination zone. The pathways of FIG. 25 may be considered to be radial pathways in that they radiate away from the source zone, i.e. from inboard to outboard.

In the embodiment of FIG. 26 the destination zone 212 is an oval shaped inboard zone (within dashed lines) Source zone 210 is the outboard perimetral region between the origins of fluid flow arrows 222 and the lateral edges of the pad. Alternatively the source zone may be any zone of the apparatus outside the destination zone. The capillary property is arranged to define one or more capillary pathways extending both laterally and longitudinally from the source zone 210 to the destination zone 212. The pathways of FIG. 26 may be considered to be radial pathways in that they radiate toward the destination zone, i.e. from outboard to inboard.

The arrangement of FIGS. 24-25 may be useful for drawing moisture away from an occupant lying on the apparatus, for example for removing urine from the site of an incontinence accident. The arrangement of FIG. 26 may be useful for directing the moisture toward a sensor 104, such as an RFID technology based sensor, which is responsive to the moisture. In another variant the destination zone includes an indicator responsive to the moisture. For example the destination zone may be constructed of a material that changes color in response to contact with urine and/or other fluids of interest or may include a decal that is similarly color responsive to urine and/or other fluids of interest. In another variant the destination zone includes a collector or may be a collector for collecting the migrated moisture. Such a collector 226 is shown schematically in FIG. 25 as an absorbent material 226A. The material of which the sheet of material 206 is made is a microfiber. A microfiber has a lineic mass of less than about 1 g/10 km, a diameter of less than about 9 micrometers, or both. The above described apparatus could be part of a system which includes an electrical circuitry, such as a processor or controller (e.g., a phase-locked loop or PLL), for detecting or analyzing fluid that comes in contact with a sensor 104 in destination zone 112.

Directional Architecture—Hydroaffinity.

FIGS. 27-29 show variants of an architecture for a moisture handling apparatus, which may be an incontinence pad. The illustrations illustrate a pad-like apparatus having a head end H, a foot end F longitudinally spaced from the head end, a left side L and right side R laterally spaced from the left side. The illustrations also show longitudinally and laterally extending centerlines 200, 202. The apparatus comprises a sheet 206 of material having a hydroaffinity property for encouraging moisture migration from a source to a destination. "Hydroaffinity" as used herein refers to the degree to which the material is hydrophilic, hydrophobic, or some combination of hydrophilic and hydrophobic, such as exhibiting a hydrophilic/hydrophobic gradient. The hydroaffinity property encourages moisture migration from a source zone 210 to a destination zone 212. The hydroaffinity property is spatially arranged or oriented so as to encourage moisture migration from the source zone 210 to the destination zone 212.

In the example embodiment of FIG. 27 the source zone 210 is an inboard zone (within dashed lines) whose longitudinal dimension substantially exceeds its lateral dimension. Zone 210 is approximately laterally centered on centerline 200. Destination zone 212 is the outboard perimetral region between the points of fluid flow arrows 222 and the lateral edges of the pad. Alternatively the destination zone may be any zone of the apparatus outside the source zone. As used herein the term "inboard" refers to locations relatively remote from the edges of the bed whereas "outboard" refers to locations relatively closer to the edges of the bed. The hydroaffinity property is arranged to define one or more fluid migration pathways (suggested by the fluid flow arrows 222) extending substantially exclusively laterally from the source zone to the destination zone. Each flow arrow may be considered to represent a fluid migration pathway. Alternatively all the flow arrows extending in either the left or right direction may be considered to be a single fluid migration pathway. Alternatively all the flow arrows extending all directions may be considered to be a single fluid migration pathway. FIG. 27 includes a graph whose abscissa axis represents the left to right dimension of the apparatus 103 and whose ordinate axis shows a gradation of hydroaffinity. The graph shows that the sheet of material is relatively more hydrophobic in the vicinity of centerline 200 and is more hydrophilic at the left and right lateral edges.

In the embodiment of FIG. 28 the source zone 210 is an elongated oval shaped inboard zone (within dashed lines) Destination zone 212 is the outboard perimetral region between the points of fluid flow arrows 222 and the lateral edges of the pad. Alternatively the destination zone may be any zone of the apparatus outside the source zone. The hydroaffinity property is arranged to define one or more fluid migration pathways extending both laterally and longitudinally from the source zone to the destination zone. The pathways of FIG. 28 may be considered to be radial pathways in that they radiate away from the source zone, i.e. from inboard to outboard. FIG. 28 includes graphs similar to that of FIG. 27 showing a gradation of hydroaffinity in both the lateral and longitudinal directions. One graph shows that the sheet of material is relatively more hydrophobic in the vicinity of centerline 200 and is more hydrophilic at the left and right lateral edges. The other graph shows that the sheet of material is relatively more hydrophobic in the vicinity of centerline 202 and is more hydrophilic at the head and foot edges.

In the embodiment of FIG. 29 the destination zone 212 is an oval shaped inboard zone (within dashed lines) Source zone 210 is the outboard perimetral region between the origins of fluid flow arrows 222 and the lateral edges of the pad. Alternatively the source zone may be any zone of the apparatus outside the destination zone. The hydroaffinity property is arranged to define one or more fluid migration pathways extending both laterally and longitudinally from the source zone 210 to the destination zone 212. The pathways of FIG. 29 may be considered to be radial pathways in that they radiate toward the destination zone, i.e. from outboard to inboard. FIG. 29 includes graphs similar to those of FIG. 28 but with an opposite gradation of hydroaffinity to account for the fact that the destination zone is an inboard zone and the source zone is an outboard zone. The graphs show that the sheet of material is relatively more hydrophilic in the vicinity of centerline 200 and more hydrophobic at the left and right lateral edges and that the sheet of material is relatively more hydrophilic in the vicinity of centerline 202 and is more hydrophobic at the head and foot edges.

The arrangement of FIGS. 27-28 may be useful for drawing moisture away from an occupant lying on the apparatus, for example for removing urine from the site of an incontinence accident. The arrangement of FIG. 29 may be useful for directing the moisture toward a sensor 104, such as an RFID technology based sensor, which is responsive to the moisture.

In another variant the destination zone includes an indicator responsive to the moisture. For example the destination zone may be constructed of a material that changes color in response to contact with urine and/or other fluids of interest or may include a decal that is similarly color responsive to urine and/or other fluids of interest. In another variant the destination zone includes a collector or may be a collector for collecting the migrated moisture. Such a collector 226 is shown schematically in FIG. 29 as an absorbent material 226A. As seen from the foregoing explanation and illustrations the hydroaffinity property is arranged to be more hydrophobic at the source zone and more hydrophilic at the destination zone. The above described apparatus could be part of a system which includes electrical circuitry, such as a processor or PLL, for detecting or analyzing fluid that comes in contact with a sensor 104 in destination zone 112.

Visual Indicators—Color Changing.

Figure 30:
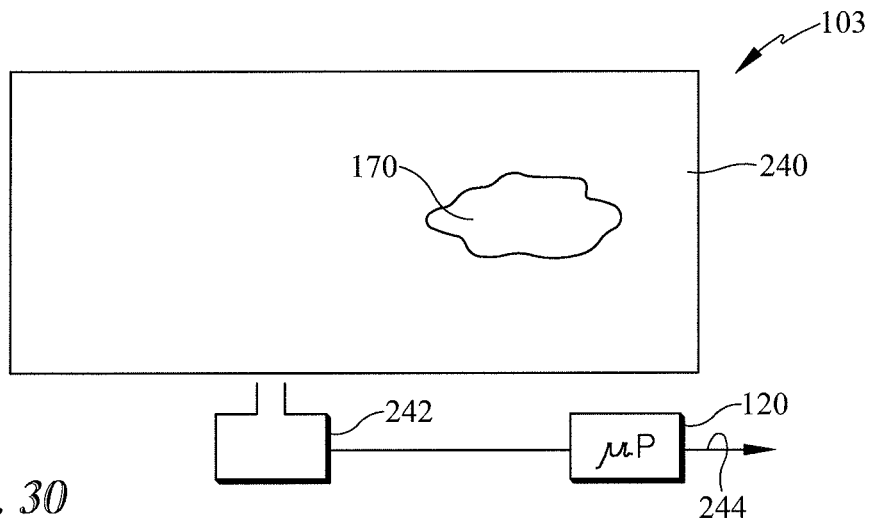
FIGS. 30-32 are simplified depictions of variants of an embodiment of an architecture for a color changing moisture detecting system, which may be an incontinence pad.
Figure 31:
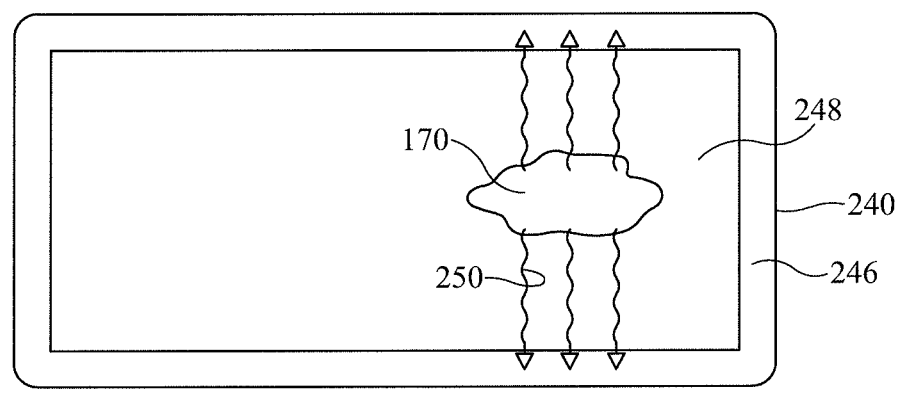
Figure 32:
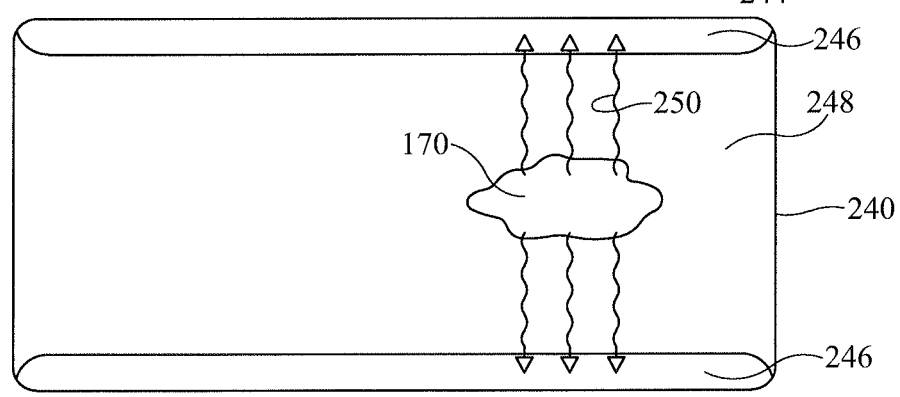

FIGS. 30-32 show variants of an architecture for a moisture detecting system, which may be an incontinence pad 103. Referring principally to FIG. 30, the moisture detecting system comprises a sheet of material 240 adapted to change color in response to the presence of moisture 170. The system also comprises a camera 242 or other color detection circuitry for observing the color change or lack thereof. The absence of a color change is a limit case which may be considered to be a "null" color change. The system also includes a controller 120 in communication with the camera. The controller processes the observations of the camera and issues a response 244. In the case of the absence of color change the response may be a null response. If a color change occurs the response may be a signal which activates an alerting or reporting system and/or records the event, such as an incontinence event, in an electronic medical record.

FIGS. 31-32 show a variant in which sheet 240 has an indicator portion 246 adapted to change color in response to the presence of moisture and a transport portion 248 adapted to transport moisture from a site of deposition thereof 170 to the indicator portion 246 as indicated by the fluid migration arrows 250. In FIG. 31 the indicator portion 246 is a perimetral portion 246. In FIG. 32 the indicator portion 246 is an edge portion 246 along one or both lateral sides of sheet 240.

The embodiment of FIG. 30 and may include features such as those of FIGS. 24-29 to transport moisture from a deposition site 170 to another site. The embodiments of FIGS. 31-32 may include features such as those of FIGS. 24-29 to transport moisture from a deposition site 170 at the transport portion 248 to the indicator portion 246 and to help transport moisture further into the interior of the indicator portion.

The color changing property referred to above is a reflective property in which the reflected wavelengths are in the visible portion of the electromagnetic spectrum. Alternatively materials that undergo a reflectivity change such that the "dry" reflected wavelengths, the "moist" reflected wavelengths, or both are not in the visible spectrum may also be used with accompanying changes to the detection circuitry.

Visual Indicators—UV from any Source+Camera.

Figure 33:
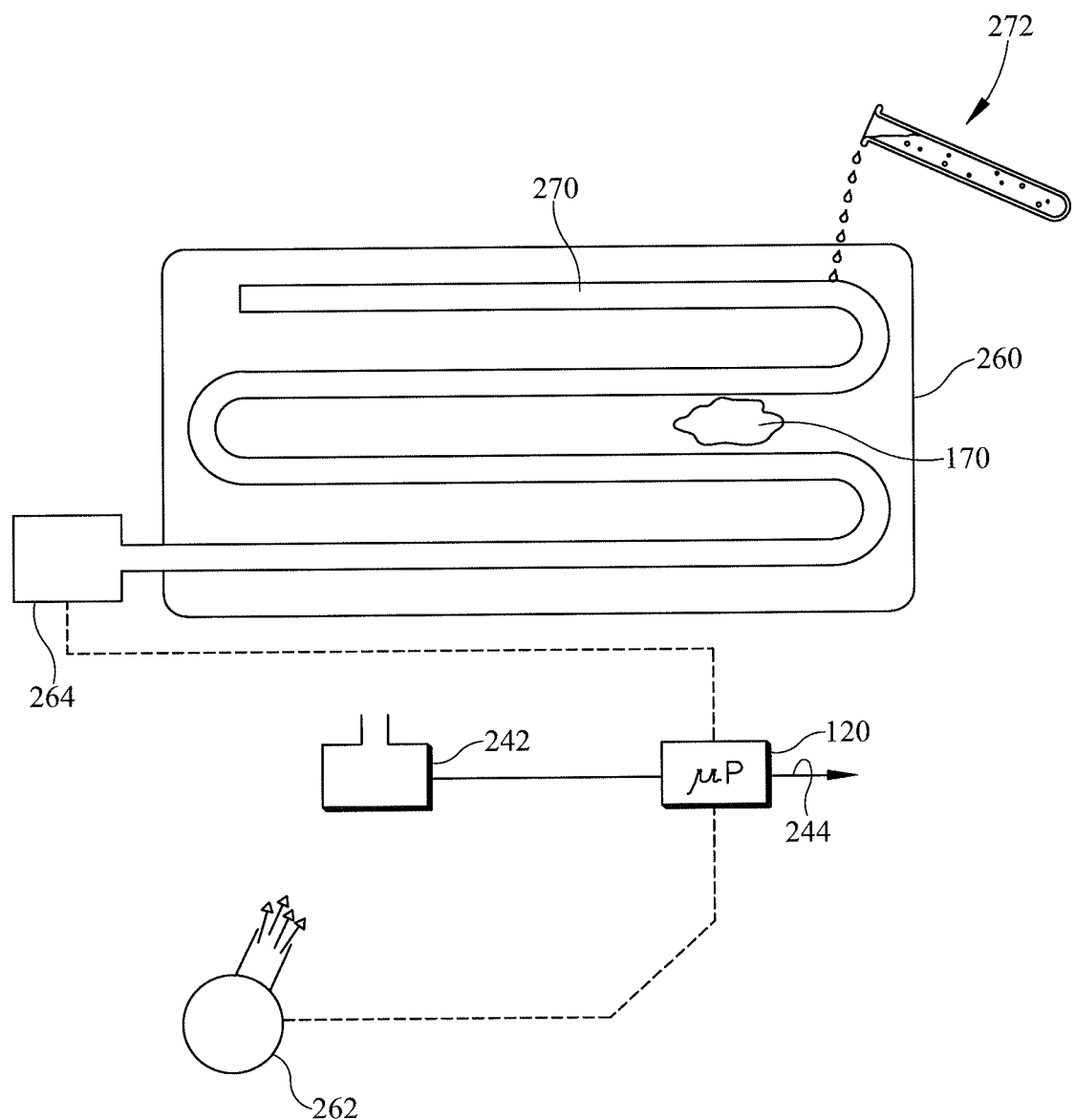
FIG. 33 is a simplified depiction of an embodiment of an architecture of another moisture detecting system, which may be an incontinence pad, and which indicates moisture presence as a result of exposure to ultraviolet radiation and which may use a camera to detect changes indicative of the presence of moisture on a previously dry surface.

FIG. 33 shows an architecture of another moisture detecting system, which may be an incontinence pad 103. The detecting system comprises a sheet of material 260 which receives the moisture 170. The system also includes a source of ultraviolet radiation adapted to expose at least a target portion of the sheet of material to ultraviolet radiation. In one embodiment the source is an external source 262. In another embodiment the source is an integrated or on-board source 264. Source 264 includes a light tube 270 that extends through the pad.

The system also includes a camera 242 or other emission detection circuitry for observing emission of radiation or lack thereof in response to the presence of moisture 170 within the target region and excitation of the moisture by the ultraviolet radiation. The absence of emitted radiation in response to the ultraviolet radiation is a limit case which may be considered to be a "null" emission.

The system also includes a controller 120 in communication with the camera and with the ultraviolet light source 262 or 264/270. The controller processes the observations of emitted radiation or a change in emitted radiation made by camera 242 (the emissions being in response to the ultraviolet excitation) and issues a response 244. In the case of the absence of emission or absence of a change in emission the response may be a null response. If an emission or change of emission is detected, the response may be a signal 244 which activates an alerting or reporting system and/or records the event, such as an incontinence event, in an electronic medical record.

The controller may periodically activate and deactivate the source of ultraviolet radiation 262 or 264/270. Alternatively the source may be manually activated at the discretion of a caregiver. Sheet of material 260 may be chemically treated 272 to intensify the radiated emission thereby making it more readily detectable.

Visual Indicators—UV from Light Tube.

In another embodiment camera 242 and processor are absent and the system comprises the sheet of material 260 which receives the moisture and a source of ultraviolet radiation comprising an ultraviolet radiation generator 264 and a light tube 270 that extends through the sheet for distributing the ultraviolet radiation to the target region thereby exposing at least a target portion of the sheet of material to the ultraviolet radiation. FIG. 33 shows an ultraviolet excited pad architecture similar to the color changing pad architecture of FIG. 30. However the ultraviolet excited pad architecture could be some other architecture such as that of FIGS. 31 and 32 which have both an indicator portion and a transport portion.

Multifunctional Sensor Pad

Figure 34:
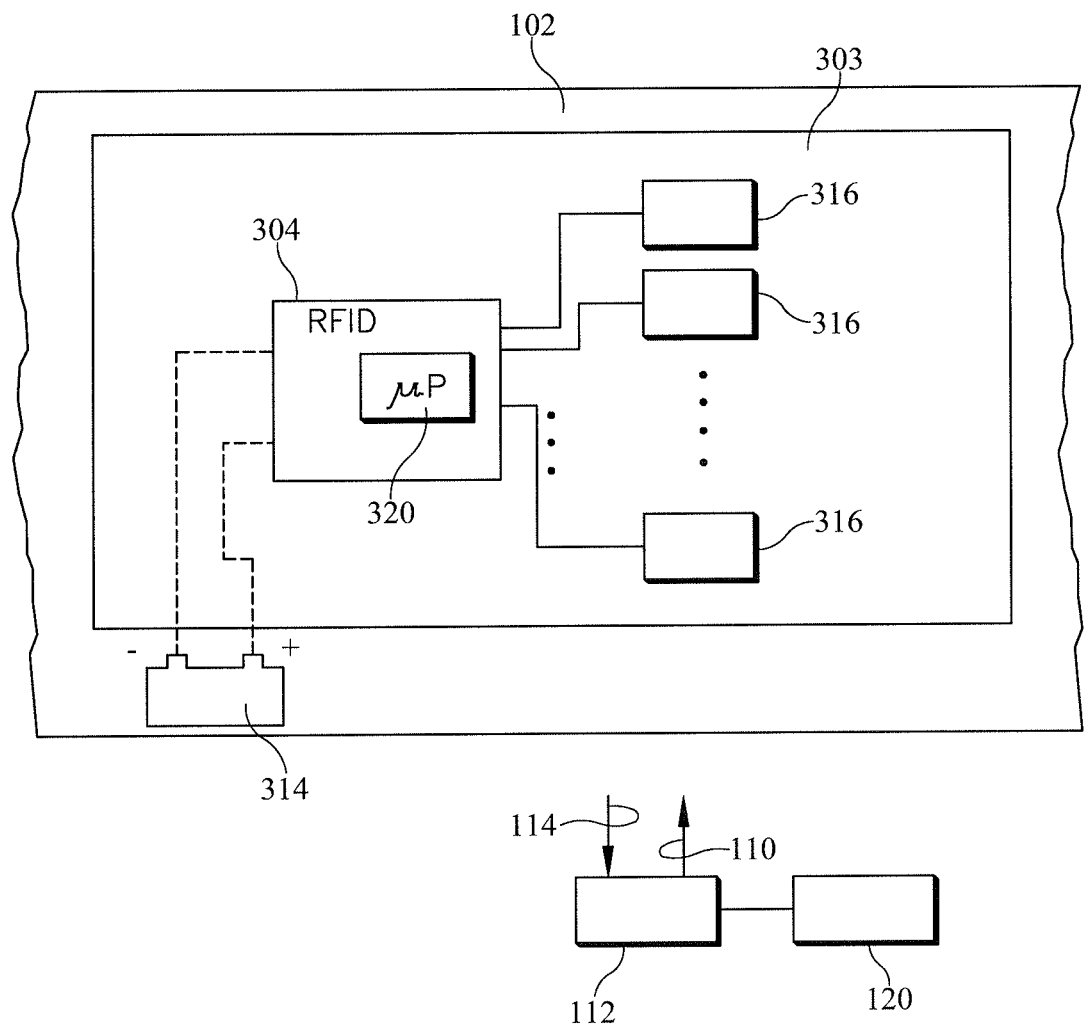
FIG. 34 is a simplified depiction of an embodiment of a sensor pad having an RFID tag with a processor adapted to process inputs obtained from multiple sensors which have different parameter sensing capabilities.

FIG. 34 shows a sensor pad 303 resting on a mattress 102 of a bed. The bed and pad are associated with an occupant or patient assigned to the bed. The sensor pad comprises at least one RFID tag 304. Tag 304 includes electrical circuitry, e.g., a processor such as microprocessor 320, adapted to process inputs obtained from multiple sensors 316 even though the sensor have disparate sensing capabilities. One suitable RFID tag is the Texas Instruments model RF430FRL152H tag. Processor 320 receives the input from sensors 316 in the form of electric or electromagnetic signals. For example sensors 316 may have sensing capabilities such as moisture sensing, odor sensing, chemical identity sensing, chemical property sensing, interface pressure sensing, sound sensing, and vital sign sensing to detect vital signs (e.g. blood pressure, heart rate, respiration rate, skin temperature, internal temperature) of a patient associated with the pad. On a given pad 303 sensors may all have the same sensing capability (e.g. interface pressure sensing) or a pad may have sensors 316 for sensing two or more parameters. The technology upon which the sensing capability is based may be any suitable technology such as an accelerometer or a vibration sensor or a sensor based on piezoelectric, piezoresistive, capacitive, inductive, or resistive principles.

Certain sensors may be able to sense a parameter of interest directly and report the value of the sensed parameter to processor 320 by way of an electric or electromagnetic signal. Other sensors may respond to the sensed parameter in a way that requires interpretation by the processor 320.

As already noted in this application, RFID sensors can be employed to sense moisture, for example urine deposited on the mat as the result of patient incontinence. Nevertheless sensors 316 may also be used to sense moisture. Alternatively, the RFID can be relied on for its ability to indicate the presence of moisture as a result of its moisture dependent properties, and the other sensors 316 may be relied on for their capability to sense parameters other than moisture. Battery 314 is optional and may be included to enable RFID tag 304 to actively broadcast a signal.

Sensor/Switch Closed by Dissolution of Insulator.

FIGS. 35-36 show a sensor pad which may be an incontinence pad 103. The pad includes a sensor 330 comprising a switch 332 having a first terminal 334, a second terminal 336, and an electrically conductive bridge 340 at one end of a shank 342. The sensor also includes a fuse 346. The illustrated fuse is a patch of electrically insulative material interposed between bridge 340 and terminals 334, 336. A coil spring 350 urges the bridge against the fuse.

The fuse, and therefore the switch, has an open state (FIG. 35) in which the fuse impedes the establishment of an electrical connection between the terminals. The fuse, and therefore the switch, also has a closed state (FIG. 36) in which the fuse enables the establishment of the electrical connection in response to a stimulus acting on the fuse by allowing the bridge to contact the terminals. In the illustrated embodiment the fuse is dissolvable by urine and the stimulus is the presence of urine 352 on the fuse. The urine dissolves the fuse and, as a result, spring 350 urges bridge 340 into contact with terminals 334, 336.

FIG. 37 shows an alternative embodiment in which the fuse is a membrane 356 which counteracts the force of spring 350 until contact with urine dissolves the membrane.

Figure 38:
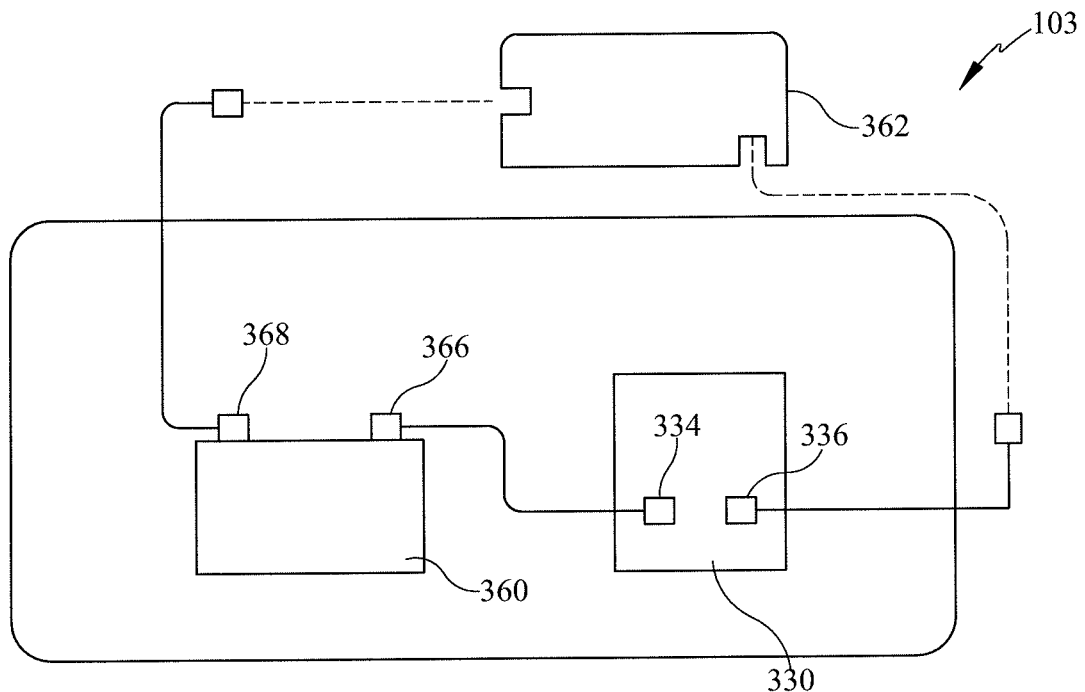
FIGS. 38-39 are simplified depictions of alternative embodiments of the system of FIGS. 35-36.
Figure 39:
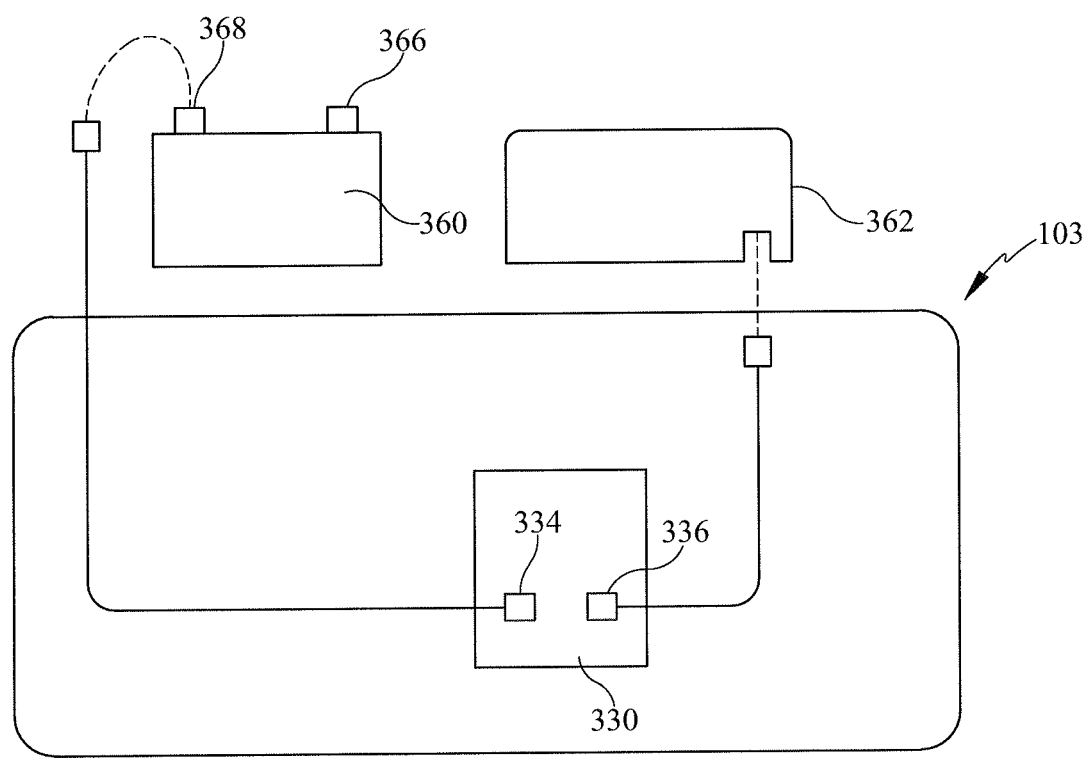

Returning to FIG. 35, one of the sensor switch terminals 334 is connected to a battery 360 and the other of the sensor switch terminals 336 is connected to a load 362. Load 362 is an alarm that responds to completion of the circuit as a result of the fuse having dissolved. The alarm may be an audible alarm or a visible alarm. As seen in FIG. 35 switch 332, battery 360 and load 362 are all components of pad 103. In another embodiment (FIG. 38) pad 103 includes only sensor 330 and battery 360. One of the battery terminals 366 is connected to terminal 334 of the sensor switch and the other of the battery terminals 368 is connectable to the load 362, which is not a component of pad 103. Switch terminal 336 is also connectable to load 362. In another embodiment (FIG. 39) pad 103 includes only sensor 330. Switch terminal 334 is connectable to battery terminal 368. Switch terminal 336 is connectable to load 362.

The foregoing example the fuse is dissolvable in response to contact with urine. Accordingly, the presence of urine in contact with the fuse is the stimulus. However the fuse can be configured to respond to a stimulus other than contact with urine, such as temperature, pressure and vibration, in which case the mechanism responsible for the change of state of the sensor switch may be something other than dissolution.

RFID with Antenna Segments United by Dissolution of Insulator.

Figures 40, 41:
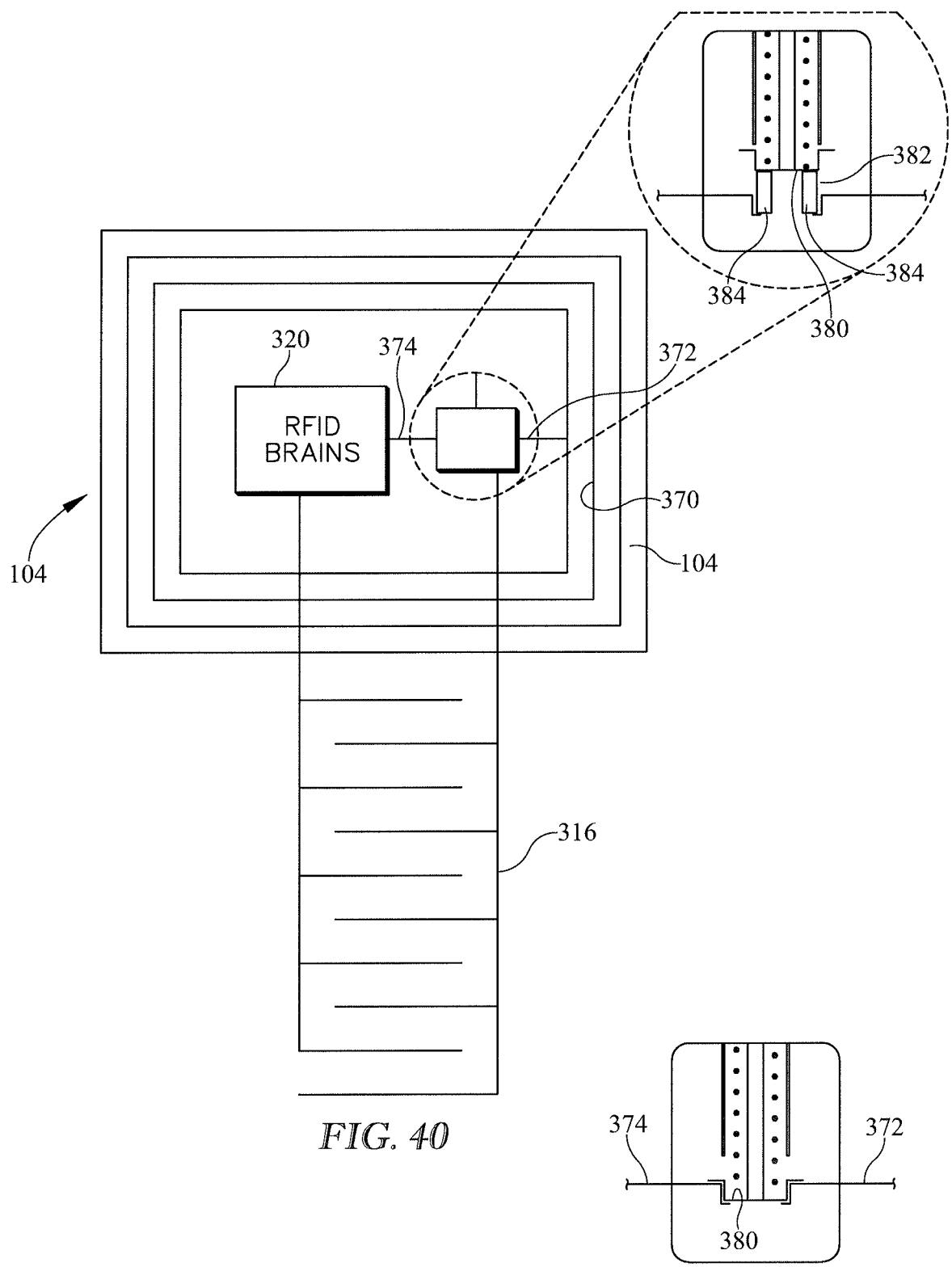
FIGS. 40-41 are simplified schematic views showing an embodiment of a sensor in the form of an RFID tag having two antenna segments and which includes a bridge which is transitionable between a first state in which a separator impedes unification of the segments and a second state in which the separator does not impede unification of the segments and in which transition from the first state to the second state occurs in response to an agent acting on the separator.

FIGS. 40-41 shows a sensor 104 in the form of an RFID tag, the tag includes an antenna 370 having at least two antenna segments 372, 374. The RFID tag also includes a bridge 380 adapted to unite the segments, and a separator 382 which is transitionable between a first state (inset of FIG. 40) in which the separator impedes unification of the antenna segments and a second state (FIG. 41) in which the separator does not impede unification of the antenna segments. In the illustrated embodiment the separator is a pair of short pillars 384. Transition from the first state (inset of FIG. 40) to the second state (FIG. 41) occurs in response to an agent acting on the separator. For example the agent may be urine which causes the separator to dissolve when the urine comes into contact with the separator. Alternatively the sensor can be configured to respond to an agent other than contact with urine, such as temperature, pressure and vibration, in which case the mechanism responsible for the change of state of the sensor switch may be something other than dissolution.

In one embodiment a single sensor subject to a state change, e.g. due to the presence of a dissolvable sensor as described above, may be excited at two different times and the return signals may be interpreted as in TABLE 4 below:

TABLE 4

| t = t0 | t = t1 | Interpretation |
|---|---|---|
| weak return | strong return | moisture present |
| weak return | weak return | moisture absent |

In another embodiment multiple sensors subject to a state change are used. One of the sensors is a first, protected sensor and one is a second, exposed sensor as described earlier in this application. A comparison of the actual response of the sensors to the expected response can be interpreted as set forth in TABLE 5 below:

TABLE 5

| Result of comparison (response vs. expected response) or assessment for first (protected) sensor | Result of comparison (response vs. expected response) or assessment for second (exposed) sensor | Interpretation (output from circuitry) |
|---|---|---|
| RSSI weak | RSSI weak | no moisture detected |
| RSSI weak or absent | RSSI strong | moisture detected |
| RSSI strong | RSSI weak or absent | fault |
| RSSI strong | RSSI weak or absent | fault |

Sensor 104 of FIG. 40 may be of the type shown in FIG. 34 which includes circuitry, such as a processor 320, in communication with adjunct sensors 316 and adapted to process inputs obtained from multiple adjunct sensors even though the adjunct sensors have disparate sensing capabilities.

Figure 42:
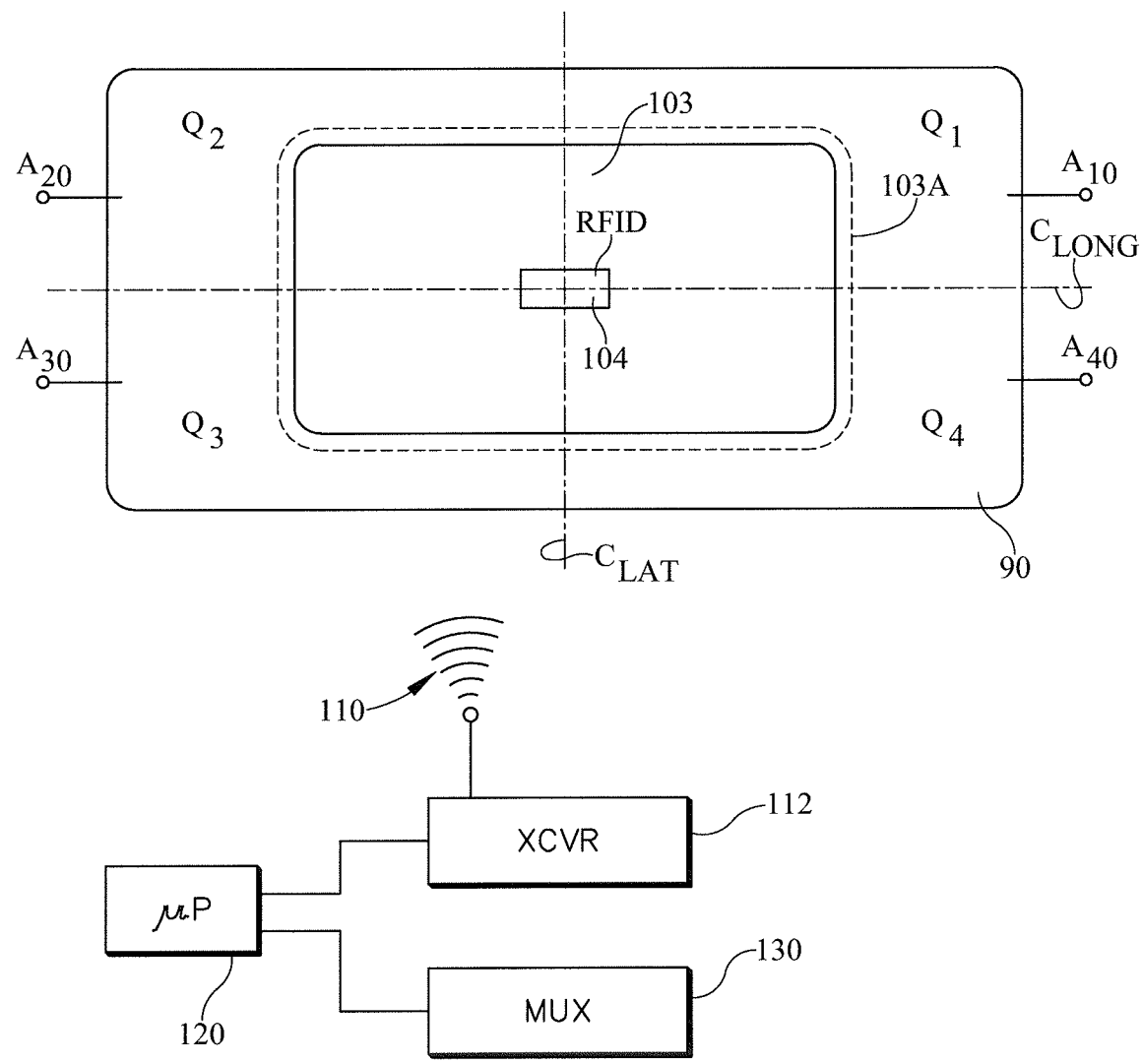
FIG. 42 is a simplified schematic view of an embodiment of a bed with an incontinence pad and a sensor and also having a set of bed antennas each of which is associated with a sector of the bed for distinguishing between the presence of moisture and displacement of the pad.

FIG. 42 shows a bed 90 having a pad 103 in a surveillance zone 103A. The pad includes a moisture responsive sensor 104 such as an RFID tag. The sensor and the mat are centered on the intersection of longitudinally extending centerline $C_{LONG}$ and laterally extending centerline $C_{LAT}$. The centerlines define four sectors or quadrants Q1, Q2, Q3 and Q4. The bed also includes four bed antennas, A10, A20, A30 and A40. The bed antennas may be components of the mattress or may be components of the bed frame. Each antenna is associated with one of the quadrants. Transceiver 112 excites the RFID at a center frequency as previously described. The multiplexer 130 causes the antennas to be powered one at a time in a desired sequence, for example first A10, then A20, then A30 then A40 and then repeats the cycle as often as desired. Electrical circuitry, such as a microprocessor 120 analyzes the returns from the antennas to distinguish between the presence of moisture on the pad and displacement of the pad. For example if the return signals from each bed antenna are all strong for an excitation cycle beginning at time t0 but are all weak for an excitation cycle beginning at a slightly later time t1, then the presence of moisture is the most probable cause of the degraded signal provided a fault has been ruled out. In a second example if an excitation cycle beginning at time t0 produces strong returns from all four antennas but an excitation cycle beginning at a slightly later time t1 produces strong returns from A20 and A30 but weaker returns from A10 and A40, then the most likely cause is that mat 103 has been displaced longitudinally toward A20 and A30. In a third example if an excitation cycle beginning at time t0 produces strong returns from all four antennas but an excitation cycle beginning at a slightly later time t1 produces strong returns from A10 and A20 but weaker returns from A30 and A40, then the most likely cause is that mat 103 has been displaced laterally toward A10 and A20. Although the foregoing example shows four sectors and four antennas, as few as two sectors and antennas may be used, and more sectors and antennas may be used to achieve additional resolution.

Referring now to FIGS. 43-47, various illustrative embodiments of a moisture (e.g., fluid) management apparatus are shown. In some embodiments, the moisture management apparatus may be embodied as or include the pad 103, described above, which may be configured as shown in any of FIGS. 43-47 and described below. In other embodiments, the moisture management apparatus may include other types of articles alternatively or in addition to the pad 103. For example, the moisture management apparatus may be embodied as or incorporated into a bed sheet, a mattress, a mattress overlay, a mattress topper, a mattress ticking, a diaper, a pad, a garment or undergarment, or another type of item, and may be disposable or re-usable, in different embodiments. For simplicity, FIGS. 43-47 illustrate the various sectional views using a rectangular shape; however, it should be understood that each or any of the embodiments of the moisture management apparatus shown may be constructed to have any desired shape (e.g., with rounded corners, or having a circular, square, oval, or other type of shape).

In general, the various embodiments of the moisture management apparatus include a number of layers of fabric material, including, in some embodiments, combinations of material having different levels of moisture permeability, such as absorbent or moisture permeable materials and moisture-impermeable materials. Such materials may include woven material, nonwoven material, directional fabrics, moisture-wicking fabrics, textiles, a combination of any of the foregoing, and/or others. Such materials may include three-dimensional materials (such as fibrous or woven materials) in which the structural arrangement of the three-dimensional fibers provides capillary action or wicking properties to direct moisture in, for example, a horizontal or vertical direction. In some cases, the fibers may be arranged in a particular pattern to urge the transfer of moisture to a desired moisture collecting region or "reservoir." Alternatively or in addition, such materials may include woven or non-woven material that is specially treated (e.g., after manufacture) to have a certain arrangement of hydrophilic/hydrophobic properties or gradients that results in the transfer of moisture to the desired collecting region. Such treatments may include, for example, physicochemical modifications of the material and/or plasma treatments.

Also in general, each of the various embodiments of the moisture management apparatus includes a top surface that is configured to interface with a body portion of a person and a bottom surface that is spaced from the top surface by a thickness of an interior region of the apparatus, where the thickness may be defined by the number of stacked layers of material in the interior region and/or the physical composition or structure of such layers of material. The bottom surface of the moisture management apparatus may be configured to engage a surface of another support structure, such as a mattress, an internal section of a mattress, a mattress cover, a deck section of a bed, a portion of an undergarment, etc. The top and bottoms surfaces may be contiguous (e.g. to form a unitary cover structure) or may be coupled by one or more fasteners (e.g., hook and loop, zipper, VELCRO brand fastener, stitching, welding, etc.).

Further, in general, the various embodiments of the moisture management apparatus include at least one sensor, which is configured to wirelessly indicate occurrences of moisture events as described elsewhere in this document. Such sensor(s) may be placed on or in a layer of material within the interior region of the moisture management apparatus. The position of the sensor(s) may be fixed using any suitable fastening technique, including an adhesive, stitching, and/or others. The sensor(s) may be shown in the drawings as having a circular or elliptical shape, for simplicity. However, it should be understood that each of the sensor(s) may have any suitable shape.

Figure 43:
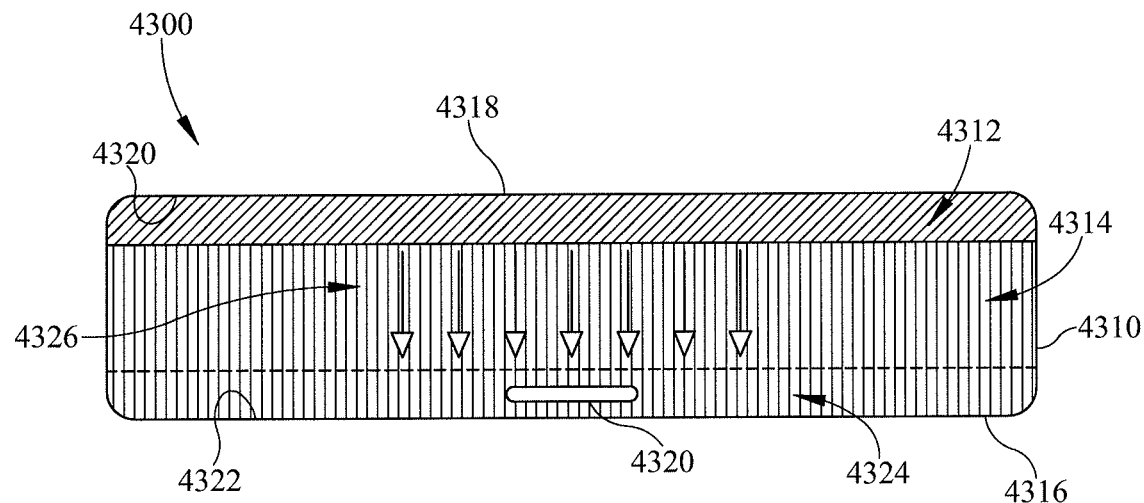
FIG. 43 is a simplified sectional view of at least one embodiment of a moisture management apparatus including at least one sensor and a number of internal layers of material having varying moisture absorption properties.

FIG. 43 illustrates a simplified sectional view of a moisture management apparatus 4300, showing the internal composition of the apparatus 4300, which includes an arrangement of layers of fabric material designed to direct moisture away from a body portion of a person interfacing with an upper surface 4318 of the apparatus 4300. A cover 4310 defines an interior region that includes an upper layer 4312, a middle layer 4314, and a lower layer 4324. A top portion of the cover includes the upper surface 4318 and a lower surface 4320. The upper surface 4318 of the top portion of the cover 4310 is constructed of a hydrophilic material (e.g., an absorbent material such as cotton). The lower surface 4320 of the top portion of the cover 4310 is positioned opposite the upper surface 4318, and is constructed of a hydrophobic material (e.g., a water resistant or waterproof material, such as plastic or a plastic-coated textile). The configuration of the hydrophilic material 4318 backed by the hydrophobic material 4320 allows fluid (e.g., moisture) to be absorbed by the upper layer 4312 and travel downwardly (e.g., by the force of gravity) through the hydrophobic material 4320, but typically does not allow the fluid to travel back through the hydrophobic material 4320 in the reverse direction. As such, moisture absorbed by the upper layer 4312 exits the upper layer 4312 by traveling downwardly through the middle layer 4314 rather than upwardly back toward the body portion of the person. Moisture is primarily retained in the middle layer 4314 and/or the lower layer 4316 (e.g., depending on the volume of moisture absorbed by the apparatus 4300).

As indicated by the arrows 4326, the middle layer 4314 is constructed with a directional wicking material, such as a moisture wicking fabric or directional fabric (e.g., polyester or poly/cotton blend). Some examples of such materials are commercially available under brand names such as COOL-MAX, DRY FIT, and/or others. The material or combination of materials in the middle layer 4314 is configured to urge or direct moisture absorbed by the upper layer 4312 toward the lower layer 4316. Accordingly, the apparatus 4300 is designed so that moisture collects in a "moisture reservoir" area 4324, which is spaced from the upper layer 4312 and the upper surface 4318 more particularly. One or more sensors 4320 are positioned in the moisture reservoir area 4324. For simplicity, only one sensor is shown in the drawings of FIGS. 43-46; however, it should be understood that any suitable number of sensors may be incorporated into any of the embodiments of the moisture management apparatus, in accordance with the requirements of a particular design.

The sensor(s) 4320 are configured to wirelessly indicate moisture events, locally at the moisture management apparatus 4300 and/or at another device (such as a hospital bed or siderail unit, a mobile device, an electronic status board, a dome light, and/or others). For example, the sensor(s) 4320 may be embodied as radio frequency identification (RFID) sensors configured to operate in any of the manners described elsewhere in this document (e.g., by responding to an electromagnetic signal in different ways depending on the degree to which moisture is present or absent in the moisture reservoir 4324 of the moisture management apparatus 4300). In other embodiments, the sensor(s) 4320 may include a humidity sensor (e.g., a relative humidity sensor) or another type of sensor that can detect the presence of moisture. Additionally, each or any of the sensor(s) 4320 may be embodied in a rigid material, a semi-rigid material, or a flexible material, according to the requirements of a particular design. For example, the sensor(s) 4320 may be printed on paper or plastic film, or may be a capacitive fabric sensor (in which an insulating layer is sandwiched between conductive fabric layers), or another suitable type of sensor. In some embodiments, the sensor(s) 4342 may be constructed using a water soluble fabric (e.g., polyvinyl alcohol or PVA) that arranged so that when it dissolves, it closes an electric circuit and thereby indicates the occurrence of a moisture event. With such a hard-contact closure, the occurrence of a moisture event can be detected and communicated without requiring a power source (e.g., a battery), without requiring wireless connectivity, or without requiring a specially configured bed or support surface 4730, in some embodiments.

In general, the indicating of a moisture event by one or more of the sensors 4320 is accomplished by the sensor 4320 or another electronic component connected thereto generating a human-perceptible output, such as an alert, signal, or notification (e.g., a visual, audible, or tactile notification). The detection of moisture may be effectuated using any of the sensor structures and techniques described earlier in this document, for example. In some cases, the absence of output, rather than the presence thereof, may indicate a moisture event. Such output (or absence thereof) may be presented or made evident locally, e.g., at the moisture management apparatus, communicated to and presented or made evident at an adjacent device (such as a bed frame, control module, or display), or communicated to and presented or made evident at a remote device (such as an electronic status board located in a healthcare facility, or a computing device) (such as a desktop or wall-mounted nurse's station of a nurse call system, or a mobile computing device, such as a smart phone, tablet computer, or wearable computing device (e.g., a VOCERA® device, GOOGLE GLASS, smart watch, etc.).

Figure 44:
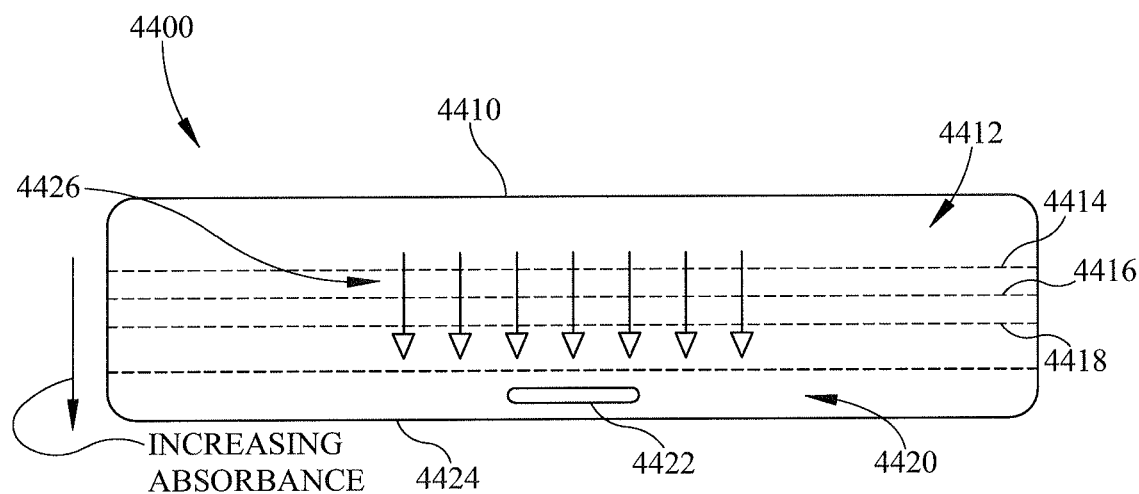
FIG. 44 is a simplified sectional view of at least one embodiment of a moisture management apparatus including at least one sensor and a number of internal layers of material having varying moisture absorption properties.

Referring now to FIG. 44, a simplified sectional view of another embodiment 4400 of a moisture management apparatus includes a cover 4410, which defines an interior region 4412. The cover 4410 includes an upper surface 4424 and a lower surface 4426. The lower surface 4426 is spaced from the upper surface 4424 by a thickness of the interior region 4412, where the thickness is defined by the number of stacked layers and the physical composition of each of the stacked layers. The upper surface 4424 is configured to interface with a body portion of a person, while the lower surface 4426 may be configured to interface with another support structure, as described above. The interior region 4412 of the moisture management apparatus 4400 includes a number of stacked layers of material, e.g., 4414, 4416, 4418, etc., each of which may be constructed using the materials described above or a combination thereof. Accordingly, the description of such materials is not repeated here.

Additionally, the layers of the interior region 4412 are arranged and/or configured to provide a hydrophobic/hydrophilic gradient such that layer(s) of material 4414 that are positioned nearer the top surface 4424 have a lesser degree of absorbency than the layer(s) of material 4418 that are positioned nearer to the bottom surface 4426. For example, the layer(s) 4416 may have a greater degree of absorbency than the layer(s) 4414 and the layer(s) 4418 may have a greater degree of absorbency than the layer(s) 4416. To do this, the layers 4414, 4416, 4418 may be constructed of different materials (e.g., each layer is constructed using a different fiber or type of fiber), or may be constructed using the same material but which is treated to have varying degrees of absorbency in the different layers, for example. As a result, moisture received by the top surface of the apparatus 4400 tends to travel through the upper layers (e.g., the area between the top surface 4424 and the layer 4414) of the interior region 4412 rather than being absorbed therein. Such moisture is thus absorbed primarily by the lower layers of the interior region 4412 (e.g., the area between the layer 4418 and the bottom surface 4426), and tends to collect in a moisture reservoir 4420. One or more sensors 4422 are positioned in the moisture reservoir 4420 and are configured to indicate moisture events. The sensor(s) 4422 may have the same or similar structure, features, and functionality as the sensor(s) 4326 described above, and/or any of the other sensors described herein. Accordingly, such description is not repeated here.

Figure 45:
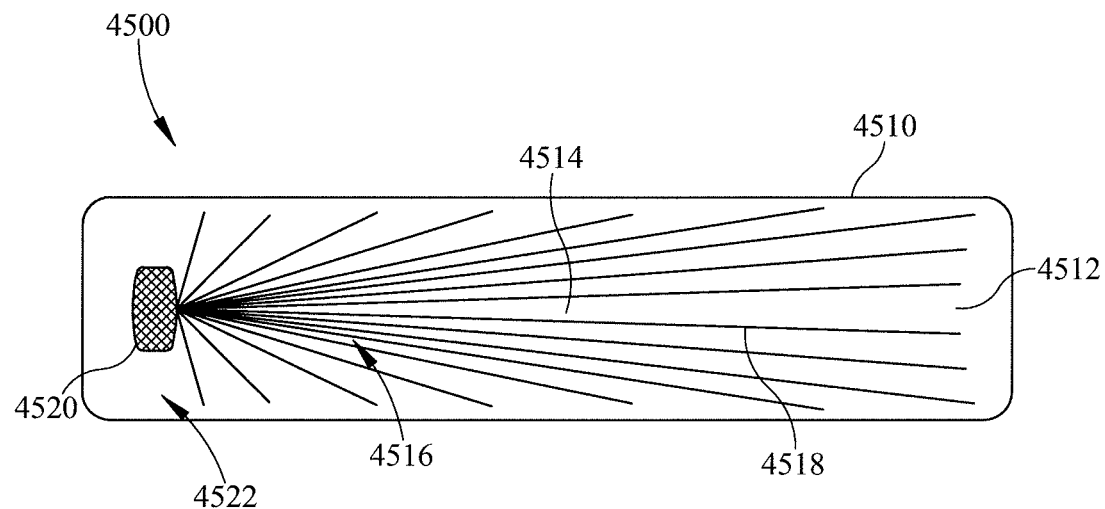
FIG. 45 is a simplified plan view of at least one embodiment of an internal layer of a moisture management apparatus and a sensor positioned near an edge of the internal layer, where the internal layer includes material having moisture transfer properties configured to transfer moisture toward the sensor.

Referring now to FIG. 45, a simplified top plan view of an embodiment 4500 of a moisture management apparatus is shown. The apparatus 4500 comprises at least one layer of material such as any of the fabric materials described above or a combination of such materials. In some cases, the apparatus 4500 constitutes a sub-layer of a larger moisture management apparatus. For example, the apparatus 4500 may constitute a portion of the moisture reservoir 4324 of the apparatus 4300 or a portion of the moisture reservoir 4420 of the apparatus 4400. In any event, the apparatus 4500 is constructed of a fabric layer 4512, which has an outer perimeter 4510, the shape of which may be defined by a number of contiguous edges, and an internal or central portion 4514. The layer 4512 is constructed using the materials and/or techniques described above to provide a moisture transfer feature 4516. The moisture transfer feature 4516 includes a number of elongated fluid pathways 4518 arranged in a pattern that extends a distance across the layer 4512. The pathways are configured to urge or direct fluid toward a fluid collecting region 4522, which is positioned adjacent the perimeter 4510 (e.g., near a longitudinal or lateral edge of the layer 4500, in embodiments in which the layer 4500 has a square or rectangular shape). A sensor 4520 is positioned in the fluid collecting region 4522. While the fluid collecting region 4522 and thus the sensor 4520 are shown as positioned adjacent a lateral side of the layer 4512 such that the fluid pathways 4518 extend longitudinally across the layer 4512, it should be understood that the fluid collecting region 4522 and thus the sensor 4520 may be positioned adjacent a longitudinal edge of the perimeter 4510 such that the fluid pathways 4518 extend laterally across the layer 4512, in other embodiments. The fluid pathways 4518 are formed by, for example, an arrangement of fibers configured to provide capillary action or with material to which a physico-chemical treatment is applied to provide a hydrophobic/hydrophilic gradient, as discussed above. For instance, areas of the layer 4512 that are farther away from the fluid collecting region 4522 are constructed with material that is more hydrophobic and areas of the layer 4512 that are closer to the fluid collecting region 4522, as well as the fluid collecting region 4522 itself, are constructed with material that is more hydrophilic. In FIG. 45, the fluid pathways 4518 emanate radially from the fluid collecting region 4522; e.g., the fluid pathways 4518 are arranged so that they tend to converge toward the location of the sensor 4520.

Figure 46:
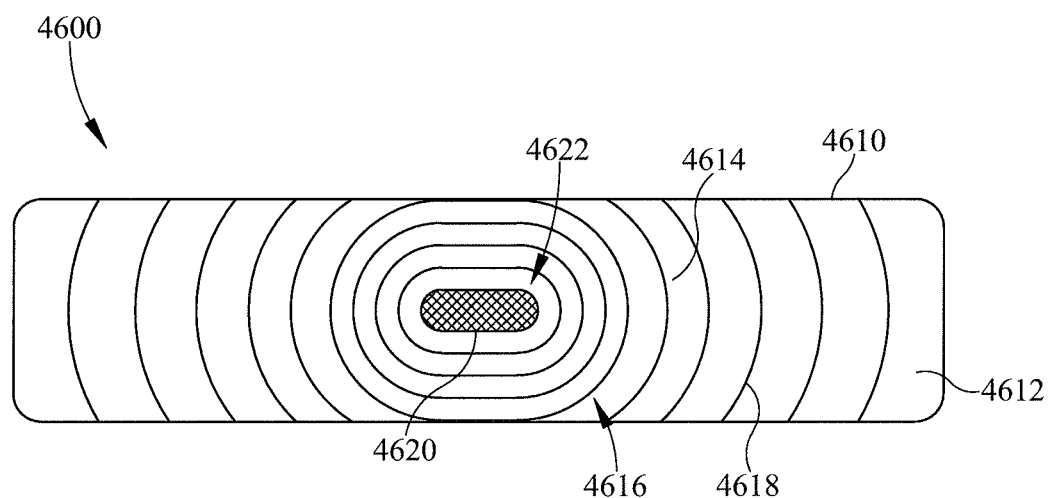
FIG. 46 is a simplified plan view of at least one embodiment of an internal layer of a moisture management apparatus and a sensor positioned near an central portion of the internal layer, where the internal layer includes material having moisture transfer properties configured to transfer moisture toward the sensor.

FIG. 46 shows a simplified top plan view of an embodiment 4600 of a moisture management apparatus, which includes a layer of material 4612 having an outer perimeter or boundary 4610 and an internal portion 4614. The embodiment 4600 is similar in many respects to the embodiment 4500, and therefore the description will not be repeated here. In FIG. 46, however, a fluid collecting region 4622 is located at or near a central area of the internal portion 4614, and a number of fluid pathways 4618 emanate substantially concentrically outwardly away from the fluid collecting region 4622, toward the perimeter 4610. As a result of this arrangement, areas of the layer 4612 that are located toward the perimeter edges 4610 are more hydrophobic while areas of the layer 4612 that are located nearer to the fluid collecting region 4622, as well as the fluid collecting region 4622, itself, are more hydrophilic. While shown as substantially elliptical for simplicity, it should be understood that each of the fluid pathways 4618 may have any suitable closed shape, such as circular, elliptical, or polygonal. As should be understood, the sensors 4520, 4620 may have the same or similar structure, features, and functionality as the sensor(s) 4326, 4422 described above, and/or any of the other sensors described herein. Accordingly, such description is not repeated here.

Figure 47:
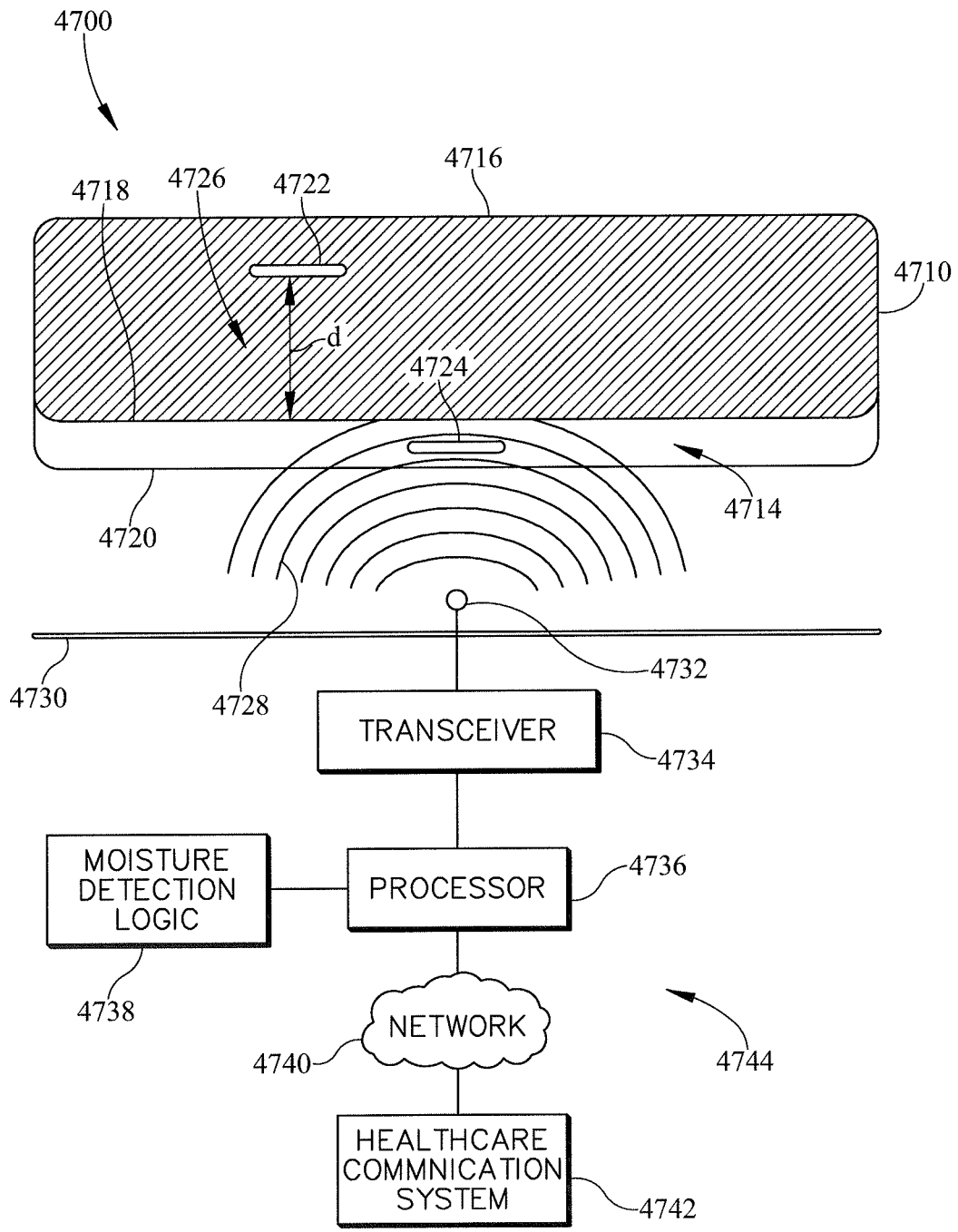
FIG. 47 is a simplified sectional view of at least one embodiment of a moisture management apparatus including at least two sensors positioned in different layers of the moisture management apparatus, and a simplified schematic view of a computer system in wireless communication with the sensors of the moisture management apparatus.

Referring now to FIG. 47, a simplified sectional view of an embodiment 4700 of a moisture management apparatus is shown. The moisture management apparatus 4700 includes a cover 4710, which defines an interior region including an upper layer 4712 and a lower layer 4714. The cover 4710 includes an upper surface 4716 and a lower surface 4714. The upper surface 4716 is configured to interface with a body portion of a person, and the lower surface 4714 is configured to be supported by another support surface 4730, such as a deck section of a bed (e.g., a seat section of a hospital bed). The embodiment 4700 has many of the same features and materials as the embodiments 4300, 4400 described above, and thus, such description is not repeated here. In the embodiment 4700, the upper layer 4712 is constructed with an absorbent material (e.g., cotton), and a layer 4718 separates the upper layer 4712 from the lower layer 4714. The layer 4718 is moisture impermeable, so that moisture absorbed by the upper layer 4712 cannot enter the lower layer 4714. The lower layer 4714 may be constructed of any suitable support material, such as foam, a three-dimensional fiber network, and/or others.

A sensor or "wet" tag 4722 is positioned in the upper layer 4712 so that it is spaced a vertical distance d from the moisture impermeable layer 4718. Another sensor or "dry" tag 4724 is positioned in the lower layer 4714, e.g., vertically below or underneath the moisture impermeable layer 4718. The sensor 4724 is kept dry by the moisture impermeable layer 4718 and/or a protective (e.g., plastic or other waterproof material) covering or enclosure, for example. In the event that moisture is received by the top surface 4716, such moisture will be absorbed by the absorbent material of the upper layer 4712 and, due to the force of gravity and/or the structural characteristics or composition of the upper layer 4712, travel downwardly toward the moisture impermeable layer 4718. As a result, moisture will tend to collect in an area 4726 of the upper layer 4712, which is vertically below or underneath the sensor 4722 and above the sensor 4714. In other words, the moisture will tend to collect in an area that is between the sensor 4722 and the sensor 4724.

The sensors 4722, 4724 communicate with a moisture management system 4744. Illustratively, a transceiver (e.g., an RF antenna) 4734 is mounted to the support surface 4730 so that it is positioned vertically below or underneath the moisture management apparatus 4700. The transceiver 4734 transmits wireless signals (e.g., radio waves) 4728 in the direction of the sensors 4722, 4724 (e.g., upwardly), and the sensors 4722, 4724 respond to such signals with corresponding wireless signals, for example as described earlier in this document. However, if a moisture event occurs that results in fluid collecting in the region 4726, the fluid in the region 4726 will absorb the signals 4728 before they reach the sensor 4722 and eventually completely prevent the signals 4728 from being received by the sensor 4722. When this happens, the sensor 4722's response to the signals 4728 will be altered and eventually cease. As a result, a large difference between the response signals received by the transceiver 4734 from the sensor 4724 and the response signals received by the transceiver 4734 from the sensor 4722 may be used to detect a moisture event.

The illustrative moisture management system 4744 includes electrical circuitry such as a processor (e.g., a microprocessor, microcontroller, digital signal processor, etc.) 4736, which is in communication with the transceiver 4734 and with computer memory (not shown) having embodied therein a computerized module, routine, or instructions executable by the processor 4736 to analyze the signals received by the transceiver 4734 and apply moisture detection logic 4738 thereto, to determine if a moisture event has occurred. An illustrative example of a method 4800 that may be executed by the processor 4736 alone or in combination with other components of the moisture detection system 4744, as moisture detection logic 4738, is shown in FIG. 48 and described below.

In some embodiments, the processor 4736 is communicatively coupled to one or more other computing systems, such as a healthcare communication system 4742 (e.g., a nurse call system and/or a medical records system), by one or more networks 4740 or other communication links. As such, occurrences of moisture detection events detected by the processor 4736 executing the moisture detection logic 4738 can be communicated to one or more other electronic devices, as described above. Any of the communication links coupling the transceiver 4734, the processor 4736, the network 4740, and the healthcare communication system 4742 may be embodied as wired connections, wireless signal paths, or a combination thereof, using any suitable electronic signal communication technique and/or protocol.

In some cases, the processor 4736 may directly communicate with an assigned caregiver's electronic device based on the incontinence event. Some examples of systems in which incontinence alerts are communicated to nurse call systems and particular caregivers are contacted directly by a monitoring system in response to an alarm condition are described in U.S. Pat. Nos. 5,537,095 and 7,319,386, which are incorporated herein by reference. For example, alerts may be sent by the processor 4736 to wireless communication devices (pagers, cell phones, PDA's, etc.) of caregivers in response to alarm conditions detected by the moisture detection sensors 4722, 4724. In general, any of the disclosed moisture detection/management devices (e.g., incontinence detection devices) can signal a nurse call system or other communication systems to communicate moisture events to wireless communication devices carried by caregivers.

Figure 48:
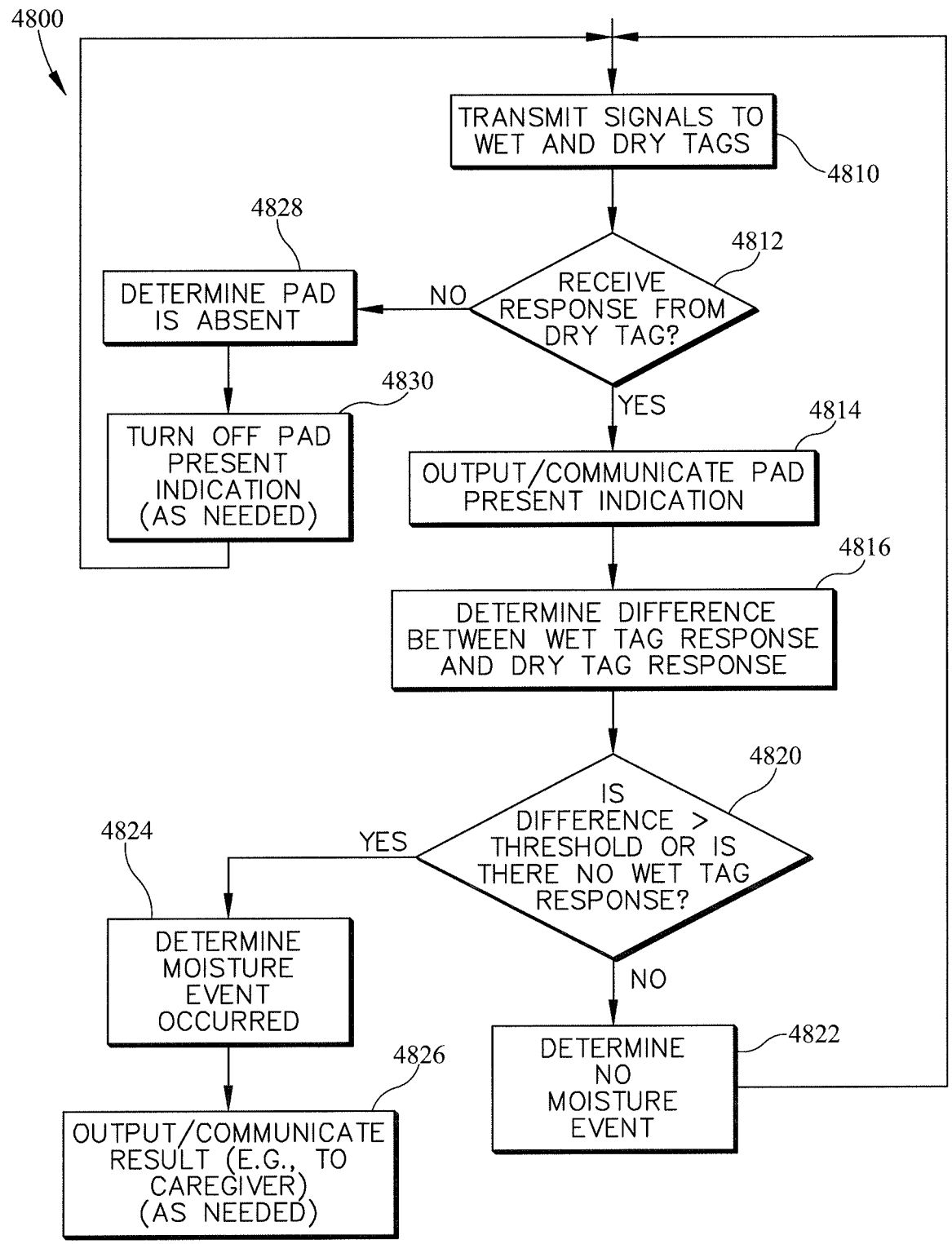
FIG. 48 is a simplified flow diagram of at least one embodiment of a method for detecting a moisture event with a moisture management apparatus as disclosed herein.

Referring now to FIG. 48, the method 4800 includes a number of computer-executable steps or instructions that can be embodied as the moisture detection logic 4738 and executed by various components of the moisture detection system 4744. At block 4810, the method 4800 (e.g., by the transceiver 4734) transmits the reference signals (e.g., RF waves of a known frequency) in the direction of the sensors 4722, 4724. At block 4812, the method 4800 (e.g., by the transceiver 4812 and/or the processor 4736) determines whether a response signal is received from the tag 4724. If a response signal is not detected as having been received from the tag 4734, the method 4800 (e.g., by the processor 4736) determines that the moisture management apparatus 4700 is in fact not in the expected location on the support surface 4730 (block 4828) and at block 4830 deactivates or disables a "present" notification if such notification had been previously active (e.g., if the moisture management apparatus 4700 had been previously detected but is no longer detected as being present in the expected location of the support surface 4730). Following block 4830, the method 4800 returns to block 4810 and continues transmitting the reference signals to monitor for the presence of the moisture management apparatus 470 and the occurrence of a moisture event.

If at block 4812 the method 4800 (e.g., by the processor 4736) determines that a response signal has been received from the tag 4724, the method 4800 proceeds to output or communicate a "present" indication (e.g., locally or to another device, as described above) (block 4814), and determine the difference between the response signal received from the tag 4722 and the response signal received from the tag 4724 (if any) during the same sample time period (which may be defined according to the requirements of a particular design of the system 4744). To do this, the method 4800 may compare the magnitude or frequency of the response signals received from the tags 4722, 4724 (e.g., the RSSI difference, as described above). At block 4820, the method 4800 analyzes the difference between the two response signals, by comparing the difference to a defined threshold value, or simply determines whether a response signal has been received from the sensor 4722 at all. If the difference between the two response signals exceeds the defined threshold value or if no response signal has been received from the tag 4722 within the sample time period, the method determines that a moisture event has occurred (block 4824) and outputs or communicates the result (e.g., an alert or notification of the moisture event) (block 4824), locally at the moisture management apparatus 4700 and/or at another device, as described above. While not specifically shown in FIG. 48, it should be understood that following block 4826, the method 4800 may return to block 4810 and continue monitoring. If at block 4820 the method 4800 determines that the difference between the response signals received from the tags 4722, 4724 does not exceed the defined threshold value, the method 4800 determines (block 4822) that a moisture event has not occurred, and returns to block 4810 to continue monitoring for a moisture event. The threshold value used by the method 4800 may be predefined in accordance with prior research, experimentation and/or test results. Alternatively or in addition, such threshold value may be determined or adjusted during operation of the system 4744, e.g., during a set-up or calibration phase, and may be adjusted over time based on, for example, a history of caregiver responses to moisture event notifications. In some embodiments, the sensors 4722, 4724 may be embodied as ultra-high frequency RF sensors (e.g., in the range of about 900 MHz), while in other embodiments, high frequency RF sensors (e.g., in the range of about 13.56 MHz) or low frequency RF sensors (e.g., in the range of about 125 KHz) RF sensors may be used.

Figure 49:
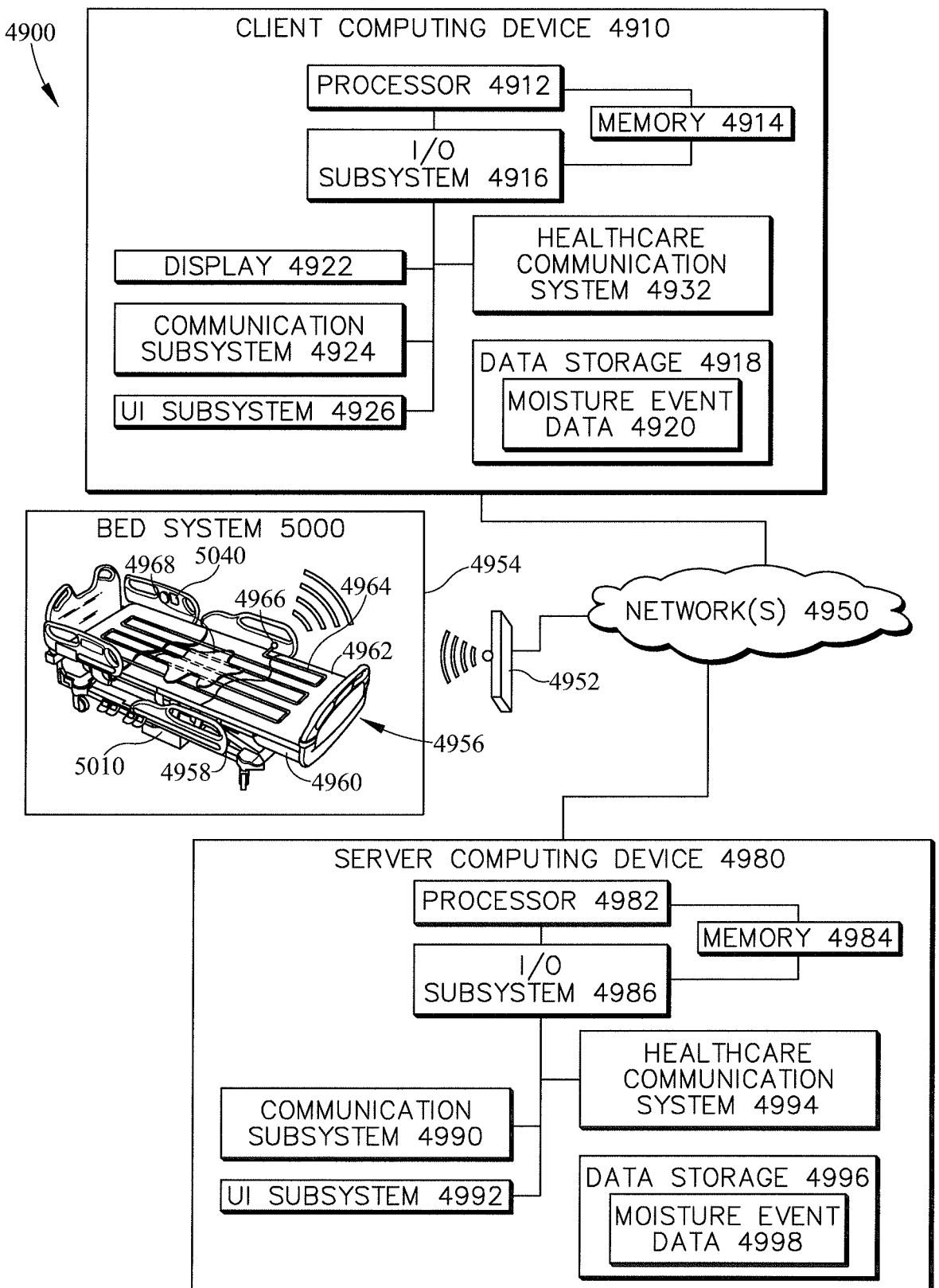
FIG. 49 is a simplified block diagram of at least one embodiment of a computing system including moisture management features as disclosed herein.

Referring now to FIG. 49, a computing system 4900 for the monitoring and detection of human-generated moisture on an occupant support includes a client computing device 4910, a server computing device 4980, and a bed system 5000, which are communicatively coupled to one another by one or more electronic communications networks 4950. The bed system 5000 includes a moisture management apparatus 4962, 4964, 4966, 5010, which detects moisture 4968 in an area supported by a patient support apparatus 4956, and communicates moisture detection indications (e.g., electromagnetic signals) to the network 4950 for use by client computing device 4910 and/or the server computing device 4980. For example, the server computing device 4980 may store the moisture detection indications in a data storage 4996 (e.g., as moisture event data 4998) for future use (e.g., reporting, auditing, or other purposes) or may determine which of any number of client computing devices 4910 should receive the moisture detection indications and transmit the moisture detection indications to such client computing devices 4910. For example, the server computing device 4980 may operate a "back end" of a healthcare communication system 4994 to transmit moisture event notifications to a "front end" of the healthcare communication system 4932 for display on a display 4922 of a client computing device 4910. In doing so, a portion of the moisture event data 4920 may be stored, at least temporarily, in a data storage device 4918 of the client computing device 4910. Such communications between the server computing device 4980 and the client computing device 4910 may be facilitated by the respective communication subsystems 4990, 4924.

In more detail, the patient support apparatus 4956 includes a frame 4958, a deck supported by the frame 4958 to support a patient in at least a horizontal position, and the moisture management apparatus 4962, 4964, 4966, 5010, which is supported by the frame 4958 or the deck, or another portion of the patient support apparatus 4956, such as a patient support surface 4960. The deck may be embodied as part of the frame 4958, in some embodiments, or may be a separate structure coupled to the frame 4958 (e.g., an articulating deck having longitudinally-spaced head, seat, and foot sections, which can pivot independently of the frame 4958), in other embodiments. The patient support apparatus 4956 may be embodied as, for example, any of the hospital beds, stretchers, lifts, or other patient support products available from the Hill-Rom Company, Inc., and the patient support surface 4960 may be embodied as, for example, any of the mattresses or other support surfaces available from the Hill-Rom Company, Inc. The illustrative moisture management apparatus includes a substrate 4962 (e.g., a moisture-absorbent pad or sensor-supporting substrate). Coupled to or disposed in the substrate 4962 is a moisture-responsive sensor 4964, which is configured to detect the presence of human-generated moisture in an area 4968 that is supported by the frame 4958 or the deck of the patient support apparatus 4956. In some embodiments, the substrate 4962 may be an integral part of the patient support surface 4960 (e.g., as an internal layer of the patient support surface 4960), while in other embodiments, the substrate 4962 may form a separate structure (e.g., a pad or a sensor sheet that can be installed on or in a pad), which is supported by the patient support surface 4960 (e.g., positioned on top of the patient support surface 4960). In either case, the substrate 4962 may be positioned within or outside of a cover. In some embodiments, the substrate 4962 is embodied as sheet or other type of supporting structure capable of supporting one or more sensors 4964 such that the sensors 4964 can perform the functions described herein.

Figure 53:
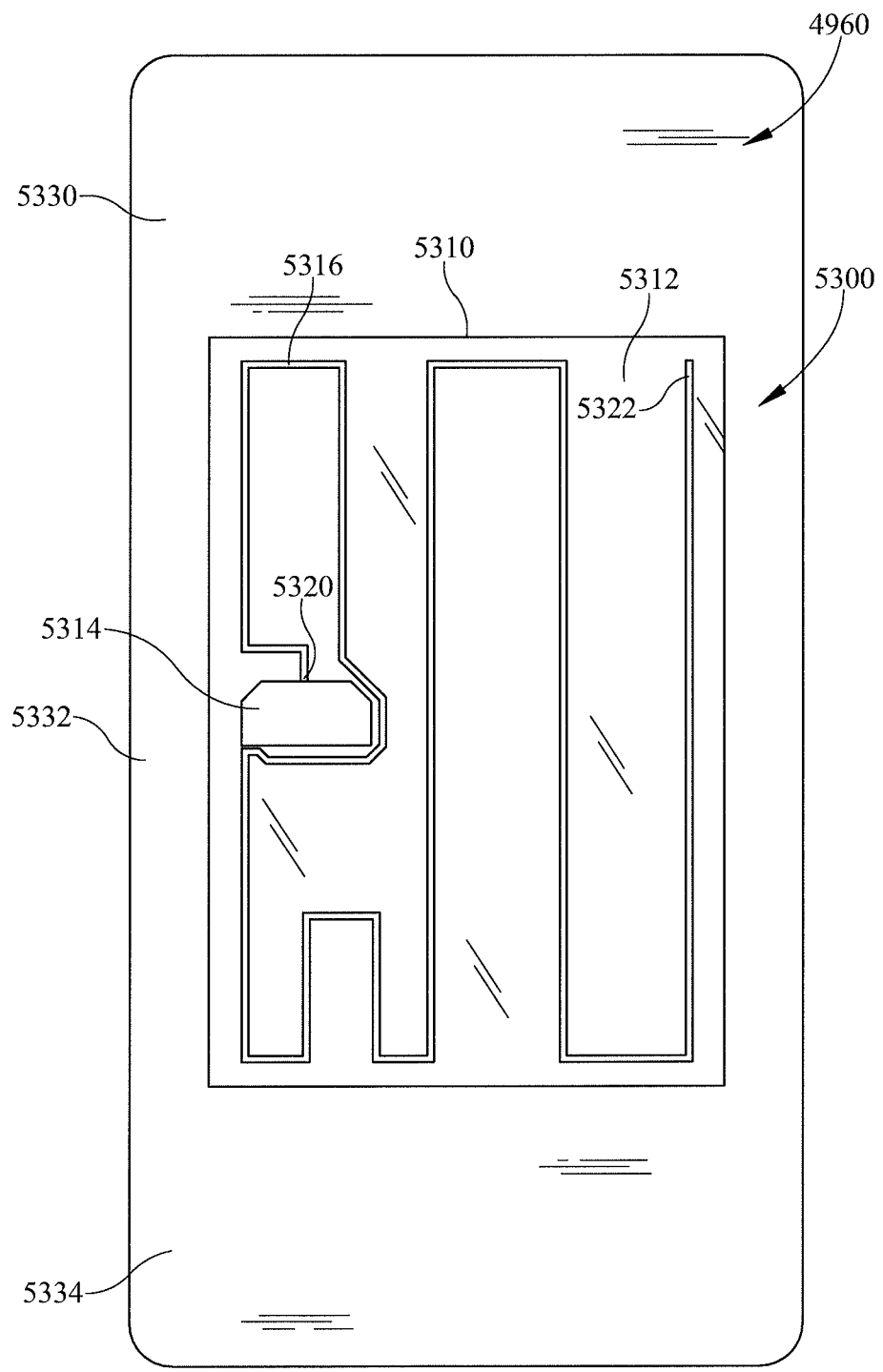
FIG. 53 is a simplified plan view of at least one embodiment of an internal layer of a moisture management apparatus, including a sensor and a moisture-responsive circuit.

Electrical circuitry, e.g. a bed controller or bed control unit 5010, and/or a transceiver 4966, is configured to communicate a moisture detection indication to a user interface device 5040, 4910 (e.g., a component of a user interface subsystem 4926), 4980 (e.g., a component of the user interface subsystem 4992), in response to a detecting by the sensor 4964 of patient-produced moisture in the area 4968 supported by the frame or the deck of the patient support apparatus 4956. In the illustrated embodiment, the transceiver 4966 communicates moisture detection indications wirelessly to a wireless access point 4952 of the network(s) 4950. The sensor 4964 may be configured according to any of the sensor embodiments described herein. For example, the sensor 4964 may be embodied as an RFID sensor that is periodically interrogated by the transceiver 4966 as described above. As such, the sensor 4964 may include or be coupled to an antenna 5026 (not shown in FIG. 49), which communicates sensor response signals (e.g., moisture event indications) generated by the sensor 4964 back to the transceiver 4966. While a single sensor 4964 is shown in FIG. 49, multiple sensors may be used in other embodiments. In some embodiments, the antenna or multiple antennas are mounted to the frame 4958 or the deck of the patient support apparatus 4956. For example, a number of antennas 5026 (e.g., two or more) may be coupled to a seat section of the deck (e.g., mounted within a molded plastic insert, which is then attached to the frame 4958 or deck of the patient support apparatus 4956 by adhesive or other suitable fastener). The number, configuration, and/or positioning of the antenna or antennas 5026 may define a sensing (or surveillance zone) (e.g., the area 4968) in which moisture events may be detected with respect to the patient support apparatus 4956. The antenna(s) 5026 may be configured to establish multiple different surveillance zones or areas 4948, in some embodiments. At least the substrate 4962 and the sensor 4964 may be enclosed in a cover (not shown), which may also enclose the patient support surface 4960, or portions thereof, in some embodiments. An outline of the applicable sensing zone may be printed on the cover for ease of reference by, for example, a caregiver. Further, in some embodiments, sensing zone indicators may be provided on, for example, head and foot siderails of the patient support apparatus 4956. The sensing zone may coincide with the size of the substrate 4962, in some embodiments. For example, if the dimensions of a planar surface of the substrate 4962 substantially correspond to the dimensions of a planar surface of the patient support surface 4960, the sensing zone may cover substantially the entire area of the patient support surface 4960. Alternatively, the sensing zone may encompass less than the entire area of the patient support surface 4960, as shown in FIG. 53, described below. While a single bed system 5000 is shown, it should be understood that any number of similar bed systems 5000 may be coupled to the network(s) 4950 in a similar fashion. Thus, the client computing device 4910 and/or the server computing device 4980 may receive moisture detection indications from many different bed systems 5000 (e.g., any or all of the beds on a floor, wing, or unit of a health care facility). Additional components of the bed system 5000 are described in more detail below with reference to FIG. 50.

Referring now in more detail to the client computing device 4910, the illustrative client computing device 4910 includes electrical circuitry such as at least one processor 4912 (e.g. a microprocessor, microcontroller, digital signal processor, etc.), memory 4914, and an input/output (I/O) subsystem 4916. The client computing device 4910 may be embodied as any type of computing device capable of performing the functions described herein, such as a personal computer (e.g., desktop, laptop, tablet, smart phone, body-mounted device, etc.), a server, an enterprise computer system, a network of computers, a combination of computers and other electronic devices, or other electronic devices. For example, in some embodiments, the client computing device 4910 is a "dashboard" (e.g., a wall-mounted graphical display unit or smart TV) of the healthcare communication system 4932. Alternatively or in addition, the client computing device 4910 may be embodied as a mobile computing device, such as a smartphone or tablet computer used by a caregiver or healthcare facility personnel.

Although not specifically shown, it should be understood that the I/O subsystem 4916 typically includes, among other things, an I/O controller, a memory controller, and one or more I/O ports. The processor 4912 and the I/O subsystem 4916 are communicatively coupled to the memory 4914. The memory 4914 may be embodied as any type of suitable computer memory device (e.g., volatile memory such as various forms of random access memory).

The I/O subsystem 4916 is communicatively coupled to a number of hardware components and/or other computing systems including the display 4922, the communication subsystem 4924, and the user interface subsystem 4926, which includes one or more user input devices (e.g., a touchscreen, keyboard, virtual keypad, microphone, etc.) and one or more output devices (e.g., speakers, displays, LEDs, etc.). The I/O subsystem 4916 is also communicatively coupled to one or more storage media 4918 (in which the moisture event data 4920 may be stored), and the healthcare communication system 4932. The healthcare communication system 4932 may be embodied as, for example, any type of nurse call system, such as the NAVICARE system available from The Hill-Rom Company, Inc. It should be understood that each of the foregoing components and/or systems may be integrated with the computing device 4910 or may be a separate component or system that is in communication with the I/O subsystem 4916 (e.g., over a network 4950 or a serial bus connection).

The storage media 4918 may include one or more hard drives or other suitable data storage devices (e.g., flash memory, memory cards, memory sticks, and/or others). Portions of the moisture event data 4920 and/or other data may be copied to the memory 4914 during operation of the client computing device 4910, for faster processing or other reasons. The communication subsystem 4924 may communicatively couple the client computing device 4910 to one or more of the communication networks 4950, which may be embodied as, e.g., a local area network, wide area network, personal cloud, enterprise cloud, public cloud, and/or the Internet, for example. Accordingly, the communication subsystem 4924 may include one or more wired or wireless network interface software, firmware, or hardware, for example, as may be needed pursuant to the specifications and/or design of the particular client computing device 4910.

The server computing device 4980 may be embodied as any suitable type of computing device capable of performing the functions described herein, such as any of the aforementioned types of devices or other electronic devices, or a combination thereof. For example, in some embodiments, the server computing device 4980 may include one or more server computers including storage media 4996, which may be used to store portions of the moisture event data 4998 (which may include moisture event data from many different bed systems 5000), and/or other data. The illustrative server computing device 4980 also includes a user interface subsystem 4992 and a communication subsystem 4990, which may be embodied similarly to the components 4926, 4924, respectively, described above. The computing system 4900 may include other components, sub-components, and devices not illustrated in FIG. 49 for clarity of the description. In general, the components of the computing system 4900 are communicatively coupled as shown in FIG. 49 by signal paths, which may be embodied as any type of wired or wireless signal paths capable of facilitating communication between the respective devices and components.

Collection of the moisture event data 4998 by the server computing device 4980 (e.g., as "cloud data") can facilitate various types of reporting. For example, the healthcare communication system 4994 may aggregate the moisture event data 4998 for multiple bed systems 5000 and/or monitor and report on each bed system 5000 individually. Reporting that may be provided by the healthcare communication system 4994 may include real-time notifications of moisture events and historical information about recorded moisture events. The healthcare communication system 4994 may link and/or communicate such reports to particular caregivers or particular locations within the healthcare facility, via the network(s) 4950. The healthcare communication system 4994 and/or the moisture management apparatus of the bed system 500 can track the amount of elapsed time between the reporting of a moisture event and the time at which the moisture event is addressed (e.g., by replacing the substrate 4962), and store such information in, e.g., the data storage 4996.

Figure 50:
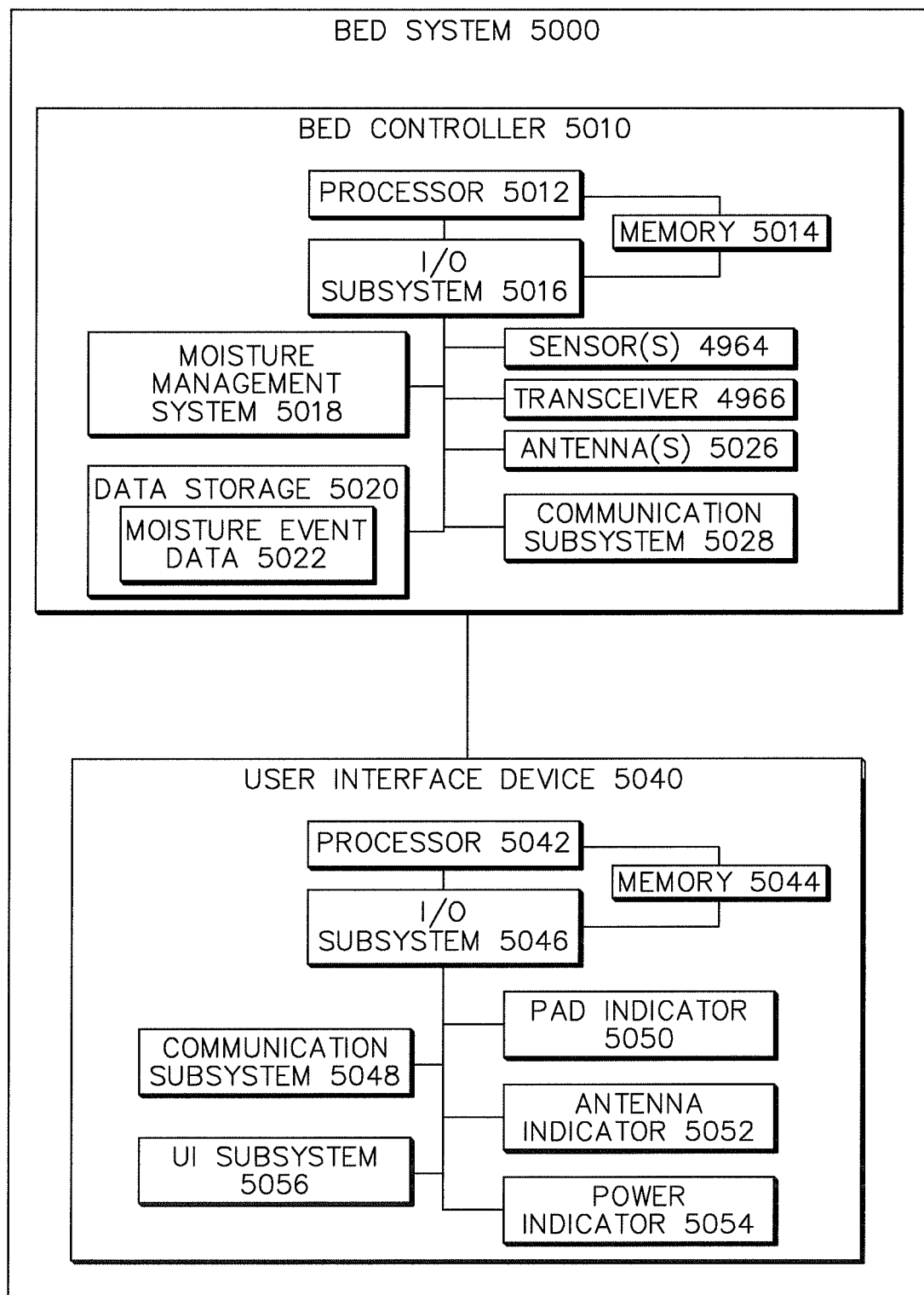
FIG. 50 is a simplified block diagram of at least one embodiment of the bed system of FIG. 49.

Referring now to FIG. 50, components of the bed control unit 5010 and the user interface device 5040 are shown in more detail. The bed control unit 5010 may be embodied as a control unit for a patient support apparatus as is provided in any of the commercially available bed products of the Hill-Rom Company, Inc. In other words, in addition to performing the moisture management functions disclosed herein, the bed control unit 5010 may operate and control many other features and functions of the patient support apparatus 4956 and/or the patient support surface 4960 (e.g., frame/deck articulation, mattress inflation/deflation, etc.). The bed control unit 5010 is communicatively coupled to the user interface device 5040 by an electrical connection (e.g., one or more wired or wireless signal paths, such as a bus, a network, insulated wiring, etc.) (e.g., a Controller Area Network or Echelon network). The user interface device 5040 may be embodied as a patient and/or caregiver user interface device of a patient support apparatus, such as a siderail unit, a footboard or headboard unit, or a pendant controller. Alternatively or in addition, the user interface device may be incorporated into a mobile computing device, such as a smartphone or tablet computer of a caregiver or health care facility personnel. Illustrative embodiments of the user interface device 5040 are shown in FIGS. 51-52, described below.

The illustrative bed control unit 5010 includes electrical circuitry such as at least one processor 5012 (e.g. a microprocessor, microcontroller, digital signal processor, etc.), memory 5014, an input/output (I/O) subsystem 5016, storage media 5020, and a communication subsystem 5028. Components of the bed control unit 5010 having the same or similar name as components already described above in connection with FIG. 49 may be embodied similarly. As the foregoing description applies to these similarly-named components, the description will not be repeated here. The moisture responsive sensor(s) 4964, the transceiver 4966, and the antenna(s) 5026 are in wired or wireless communication with the bed control unit 5010. The moisture responsive sensor(s) 4964, the transceiver 4966, and the antenna(s) 5026 may be embodied as described above (e.g., RFID sensors and antennas to communicate the sensor signals to the transceiver 4966), and are communicatively coupled to the I/O subsystem 5016 of the bed control unit 5010. In other words, moisture detection indications from the sensor(s) 4964 can be communicated to the bed control unit 5010 via the I/O subsystem 5016 and can also be communicated from the sensor(s) 4964 to the other devices on the network(s) 5950 via the transceiver 4966 and wireless access point 4952. The moisture management system 5018 is illustratively embodied as computer program logic that receives and processes the sensor signals (e.g., moisture detection indications), determines whether a moisture event has occurred, and updates a display of the user interface device 5040 to indicate moisture detection indications. Alternatively or in addition, the moisture management system 5018 executes computer logic to process the sensor signals, determine whether the sensor 4964 and/or its substrate 4962 (e.g., a moisture absorbent pad) is present on the patient support apparatus 4960, and updates a display of the user interface device 5040 to indicate the status of the sensor 4964 or the substrate 4962 (e.g., whether the moisture absorbent pad is present or whether a moisture event has occurred).

The user interface device 5040 includes electrical circuitry such as at least one processor 5042 (e.g. a microprocessor, microcontroller, digital signal processor, etc.), memory 5044, an input/output (I/O) subsystem 5046, a communication subsystem 5048, and a user interface subsystem 5056. Components of the user interface device 5040 having the same or similar name as components already described above in connection with FIG. 49 may be embodied similarly. As the foregoing description applies to these similarly-named components, the description will not be repeated here. Additionally, a pad indicator 5050, an antenna indicator 5052, and a power indicator 5054 are communicatively coupled to the processor 5042 via the I/O subsystem 5046. Each of the indicators 5050, 5052, 5054 may be embodied as, for example, a visual (e.g., one or more lights or light-emitting diodes) or audio (e.g. a speaker) output mechanism. The pad indicator 5050 is configured to activate (e.g., illuminate) if the moisture management system 5018 detects the presence of the sensor 4964 (e.g., embodied in a moisture absorbent pad) on the patient support apparatus 4960. The antenna indicator 5052 is configured to activate if the moisture management system 5018 detects that the antenna(s) 5026 are operational (e.g., supplied with electrical power). Similarly, the power indicator 5054 is configured to activate if the moisture management system 5018 detects that the sensor(s) 4964 are operational (e.g., supplied with electrical power). In this way, the indicators 5050, 5052, 5054 provide a real-time indication (e.g., to a caregiver) as to whether the moisture management apparatus 4962, 4964, 4966 is operational.

Figure 51:
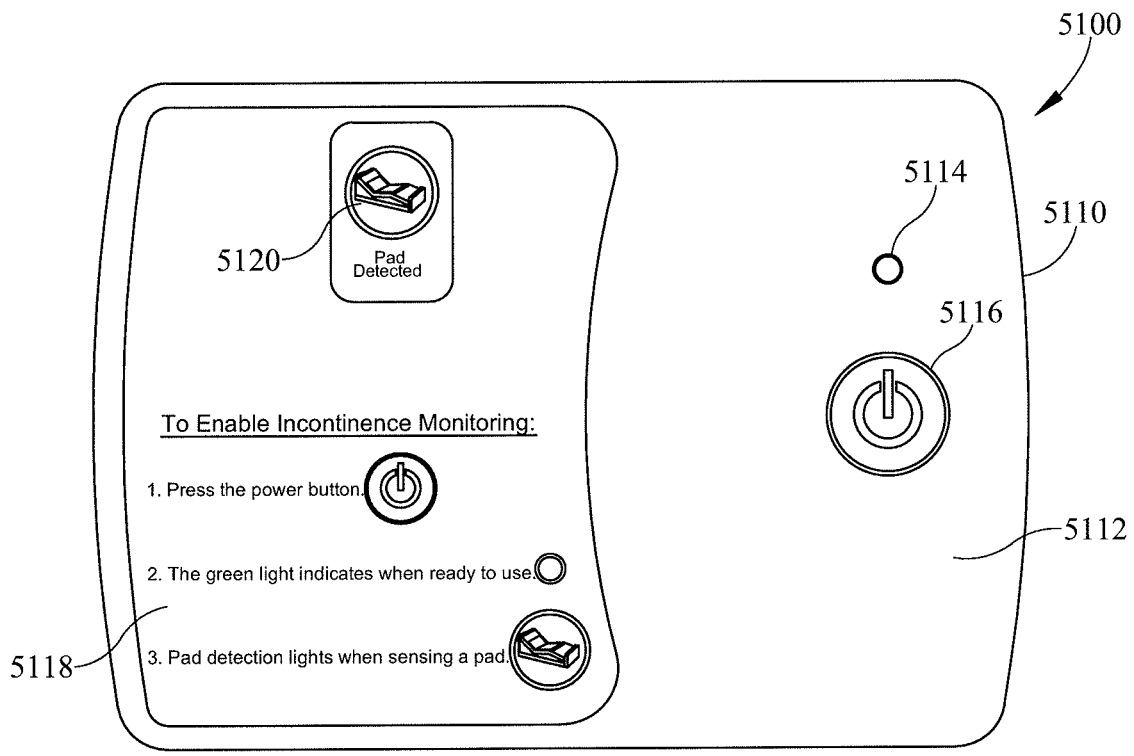
FIGS. 51-52 are simplified plan views of illustrative user interface devices of the bed system of FIG. 49.
Figure 52:
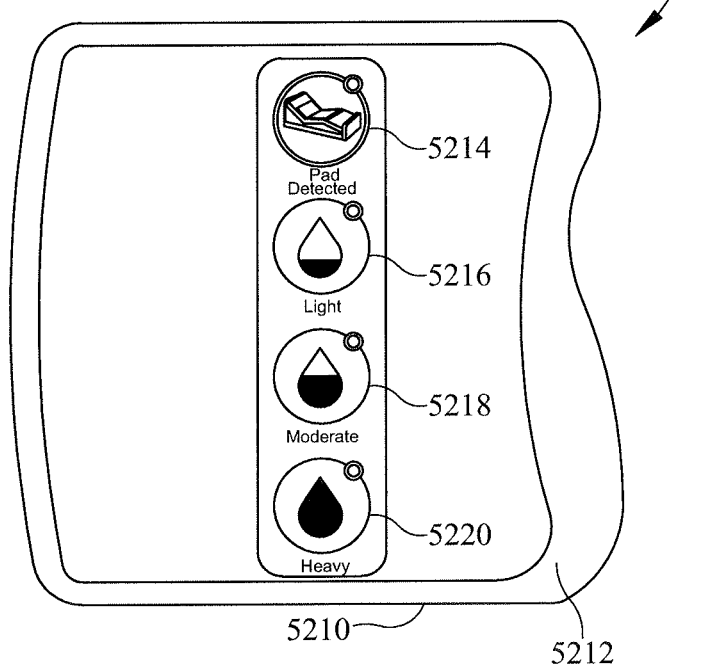

Referring now to FIG. 51, an embodiment of a user interface device 5100 is shown. The user interface device 5100 includes a housing 5110 (e.g., one or more molded plastic components), which defines an interior region in which electrical circuitry embodying the functional components shown in FIG. 50 are supported. The housing 5110 may be coupled to the frame 4958 of the patient support apparatus 4956. For example, the housing 5110 may be configured to reside on or within a siderail or endboard of the patient support apparatus 4956, in some embodiments. In other embodiments, the housing 5110 may be removably tethered to the patient support apparatus 4956 (e.g., as a pendant controller).

A user interface panel 5112 (e.g., a molded plastic piece) is part of or supported by the housing 5110. The panel 5112 supports a visual indicator 5114, an on/off power button 5116, a set of user instructions 5118, and a pad detected indicator 5120. The visual indicator 5114 is configured as, for example, a light-emitting diode, to activate (e.g., illuminate) when the moisture management system 5018 is ready to use (e.g., the antenna 5026 is operational, and the electrical power is on). In other words, the indicator 5114 may indicate that the system 5018 is ready to be used to detect the sensor 4964 and/or to detect moisture, and may not necessary indicate that the sensor 4964 is present. The pad detected indicator 5120 is configured to activate (e.g., illuminate) when the sensor 4964 is detected on the patient support apparatus 4960. The button 5116 is user-activatable (e.g., by a caregiver) to turn the moisture management system 5018 on and off.

Referring now to FIG. 52, another embodiment of a user interface device 5200 is shown. Portions of the user interface device 5200 may be constructed similarly to the user interface device 5200, and therefore the description of similar components is not repeated here. The user interface device 5200 includes a housing 5210, which supports or includes a user interface panel 5212. The user interface panel 5212 supports a number of visual indicators and selectors, including a pad detected indicator 5214 and a plurality of user input mechanisms/indicators 5216, 5218, 5220 to select a moisture level for monitoring by the moisture management system 5018. In the illustrative embodiment, each of the user input mechanisms 5216, 5218, 5220 is user-selectable to specify a progressively greater amount of moisture as the threshold for indicating that a moisture event has occurred. For instance, if a user selects the button 5216, moisture events may be detected by the system 5018 more frequently than if the user selects the button 5218. Likewise, if a user selects the button 5220, the system 5018 may detect moisture events less frequently than if the button 5218 were selected. If the button 5218 is selected, the system 5018 may detect moisture events more frequently than if the button 5220 were selected but less frequently than if the button 5216 were selected. Once a button 5216, 5218, 5220 is selected, a corresponding visual indicator may activate (e.g., illuminate) to indicate the selection. It should be noted that the system 5018 may be configured so that only one of the buttons 5216, 5218, 5220 may be activated at a time (e.g., so that the system 5018 monitors for only one type of moisture event at a time). Further, in other embodiments, multiple levels of monitoring may be specified for different moisture types, alternatively or in addition to the amount or volume of moisture. Once a moisture level is selected via a button 5216, 5218, 5220, the system 5018 communicates moisture detection indications only when the moisture-responsive sensor 4964 detects an amount of moisture that meets or exceeds the selected moisture level.

While not specifically shown, each or either of the user interface devices 5100, 5200 may include a graphical user interface, such as a touchscreen device. The graphical user interface may graphically display data indicating one or more areas of moisture that are detected by the moisture management apparatus in the area supported by the patient support apparatus. For example, the graphical display may take the form of a "map" in which different colors are used to represent different amounts, concentrations, or types of moisture that are present.

Referring now to FIG. 53, an embodiment of a moisture management apparatus 5300 is shown. The illustrative moisture management apparatus 530 may be incorporated into or supported by the patient support surface 4960. Illustratively, the patient support surface 4960 includes a head section 5330, a seat section 5332, and a foot section 5334, and the moisture management apparatus 5300 is disposed on or in the seat section 5332. The moisture management apparatus 5300 includes substrate 5312, which supports a sensing device, where the sensing device includes a sensor 5314 and a moisture directing circuit 5316. The moisture directing circuit 5316 connects to the sensor 5314 by a proximal end 5320, and terminates at a distal end 5322. Between the proximal end 5320 and the distal end 5322, the moisture directing circuit 5316 is arranged in a serpentine pattern, which illustratively extends laterally across and longitudinally along a substantially planar surface of the substrate 5312. The sensor 5314 may be embodied as any of the types of sensors described herein (e.g., one or more RFID sensors), and the moisture directing circuit 5316 may be embodied as any type of moisture directing circuit described herein (e.g., using capillary action or hydroaffinity properties of the substrate 5312). The substrate 5312 may include a non-absorbent layer that supports the moisture directing circuit 5316. The moisture directing circuit may be embodied as conductive ink or conductive thread that is applied to the substrate 5312.

The sensor 5314 is, illustratively, located adjacent to an outer border 5310, which is defined by a plurality of spaced-apart edges of the substrate 5312. The sensor 5314 may be located in the middle of a moisture absorbent pad relative to top and bottom surfaces of the pad, and near at least one edge or border of the pad. In other words, a moisture absorbent pad may include spaced-apart substantially planar top and bottom surfaces that define an interior region, and the moisture-responsive sensor may be spaced-apart from both the top and bottom surfaces so that the moisture-responsive sensor is positioned in the middle of the interior region (depthwise) (e.g., a distance greater than zero from both the top and bottom surfaces of the pad). Positioning the sensor 5314 substantially in the middle of the pad (e.g., vertically) and toward an edge of the pad (e.g., adjacent a boundary of the pad) may improve patient comfort. Further, placing the sensor in the middle of the substrate, depthwise, may allow for greater flexibility in the placement of the substrate 5312 with respect to the support surface 4960, e.g., to reduce the potential for displacement of the substrate 5312 or displacement of the sensor 5314 during use.

Figure 54:
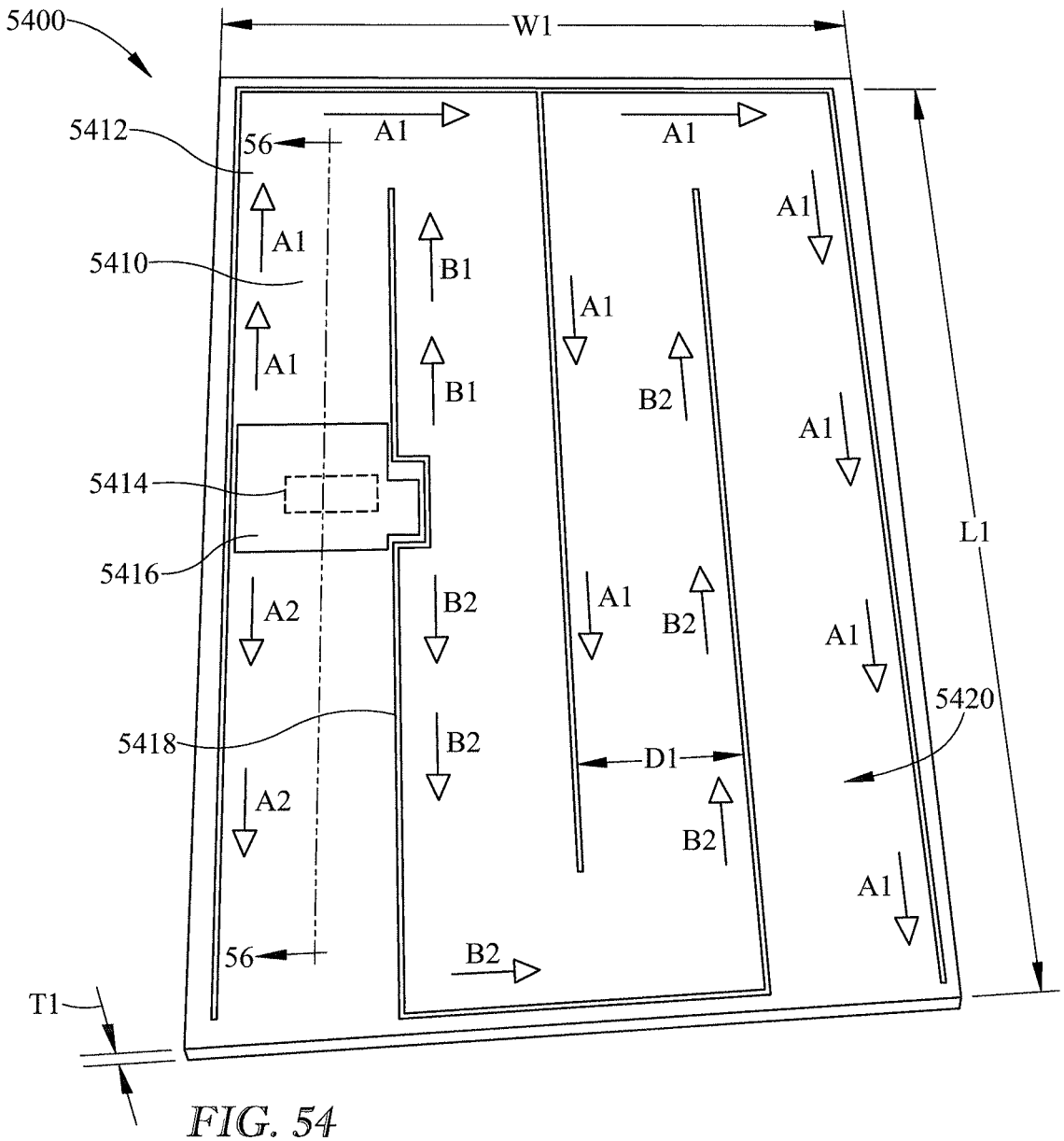
FIG. 54 is a simplified perspective view of at least one embodiment of a sensor sheet as disclosed herein.

Referring now to FIG. 54, a simplified perspective view of at least one embodiment of a moisture management apparatus 5400 is shown. The moisture management apparatus 5400 is configured to monitor an area for the occurrence of moisture events in the area. The area monitored by the moisture management apparatus 5400 for occurrences of moisture events is defined by length (L1) and width (W1) dimensions of a substrate 5410 of the moisture management apparatus 5400. The illustrative moisture management apparatus 5400 is embodied as a "sensor sheet" that may be appropriately sized and configured so as to be incorporated into or secured to another device, such as an incontinence pad, a textile, a bed sheet, a mattress, a garment, or a wearable device, such as a diaper, an undergarment, or an adhesive-backed pad. The moisture management apparatus 5400 may be supported by (e.g., placed on top of) a patient support surface, such as the patient support surface 4960, described above, or the patient support apparatus 5700 shown in FIG. 57, described below.

The substrate 5410 of the moisture management apparatus 5400 supports a sensor 5414 and a sensor circuit 5420. The substrate 5410 is designed to bear a portion of the weight of a patient's body (e.g., the sacral region) for a period of time.

For instance, some embodiments of the substrate 5410 are made of a manufacturable, non-rigid, flexible or pliable material, such as a plastic film. When combined with a more rigid support surface (such as a bed, mattress, or chair), the substrate 5410 bears a portion of the patient's weight. As an example, if the moisture management apparatus 5400 is embodied in a wearable device, such as an undergarment, the substrate 5410 bears a portion of the patient's weight when the patient sits or lays down on a bed or a chair. Similarly, if the moisture management apparatus 5400 is placed on or incorporated into a mattress, mattress pad, or bed sheet, the substrate 5410 bears a portion of the patient's weight when the patient uses the mattress, mattress pad, or bed equipped with the bed sheet. As such, the illustrative substrate 5410 is made of a support material that is configured to minimize the interface pressure experienced by the patient when the moisture management apparatus 5400 supports a portion of the patient's weight, e.g., so that the patient's peak interface sacral pressure is increased by an amount that is less than or equal to an amount that is in the range of about 8 millimeters of mercury (mm/Hg) to about 15 mm/Hg (where the "peak" interface sacral pressure may be determined for a representative sample population, such as median weight males or median weight females, and applied to the design of the substrate 5410 through laboratory testing). Accordingly, the substrate 5410 may be made of a synthetic resin or a thermoplastic polymer material, such as a polypropylene film or a polyethylene film. Alternatively, the substrate 5410 may be made of a nonwoven fabric or paper material, or other suitable material capable of performing the functions disclosed herein (such as any type of carrier substrate on which conductive ink can be printed). In any event, the substrate 5410 is a three-dimensional material having a thickness TI. In some embodiments, the substrate 5410 has a thickness in the range of about one millimeter.

The sensor 5414 is embodied as a wireless sensor, such as any of the types of sensors disclosed herein (e.g., sensor 104). The illustrative sensor 5414 is fixedly coupled to the substrate 5410, generally near or toward an edge of the substrate 5410. While a single sensor 5414 is shown in FIG. 54, it should be understood that other embodiments of the moisture management apparatus 5400 may include more than one sensor 5414; for example, two sensors may be located on opposite lateral sides, or opposite longitudinal sides, of the substrate 5410. In the embodiment of FIG. 54, the sensor 5414 supports (e.g., is covered by) a detuning material 5416, such as foam. The detuning material 5416 is configured to shield the sensor 5414 from interference from natural electrical conductivity provided by the human body of the patient using the moisture management apparatus 5400. As such, the detuning material 5416 is fixed to the sensor 5414 and/or the substrate 5410 so as to be interposed between the sensor 5414 and the patient's body. In other embodiments, detuning may be performed by electrical circuitry or by software built-in to the sensor 5414, rather than through the use of the detuning material 5416.

The sensor 5414 is configured to, in response to the presence of moisture in the monitored area, emit a wireless signal indicative of a moisture event. For example, the sensor 5414 may emit a signal at a frequency that deviates from an expected response frequency, as described above, and this deviation in the frequency may indicate that a moisture event has occurred. Also as discussed above, the sensor 5414 may emit signals in response to one or more triggering signals, which the sensor 5414 receives wirelessly from a wireless signal transmitter (e.g., the transceiver 112, described above). As such, the sensor 5414 may be embodied as a passive radio frequency identification (RFID) tag that is configured to emit sensor signals at a frequency that is configured for monitoring moisture events. A frequency that is "configured for monitoring moisture events" may be, for example, a frequency that is lower than a frequency commonly used to detect bed exit or other fall risk events. In this way, the sensor 5414 may be used in combination with other wireless devices that monitor for other patient conditions, such as sensors that monitor for fall risk events. Alternatively, the sensor 5414 may be configured to emit signals at different frequencies so that multiple different types of events can be monitored with the same sensing device. To do this, the sensor 5414 may be initially set at a predetermined frequency that is suitable for performing monitoring for a number of different types of monitored events (e.g., moisture, bed exit, and fall risk), and then shift to the appropriate frequency for monitoring a specific type of event when the sensor 5414 detects that an event of that type has occurred. The amount of frequency shift needed to monitor a specific event is, for example, a change in the frequency that is large enough (either an increase or decrease) to not interfere with the more "generalized" monitoring frequency or other monitoring frequencies. In other words, the monitoring frequencies used for different types of events are set so that the frequencies do not overlap, in some embodiments. Further, it should be noted that in some cases, detection of an event is triggered by an absence of a sensor signal rather than the presence of a sensor signal, or the combination of the presence of a signal and the absence of a different signal. For instance, if a monitoring system (e.g., the reader 5980, discussed below), identifies a patient who is present in a monitoring area (e.g., by a patient ID wristband or stocking) or detects that the patient is in bed (e.g., by a bed's monitoring system), or detects a moisture signal or fall risk signal from a sensor in the monitoring area, and then after a period of time fails to detect any of those signals, the monitoring system may conclude that the patient has left the monitoring area.

The sensor circuit 5420 is embodied as a pair of differently-charged electrically-conductive traces 5412, 5418. For example, the trace 5412 is positively charged while the trace 5418 is negatively charged, or vice versa. The sensor 5414 is configured to, in response to the presence of moisture between the traces 5412, 5418, emit a signal indicative of a moisture event as described above. For example, the moisture acts as a switch that closes the circuit formed by the otherwise spatially and electrically separated traces 5412, 5418. The electrically conductive trace 5412 is supported by the substrate 5410 and is connected to an input of the sensor 5414 as shown in greater detail in FIG. 55, described below. The electrically conductive trace 5412 includes a number of segments indicated by arrows A1, which are connected end-to-end in a continuous manner, and a plurality of segments indicated by arrows A2, which are connected end-to-end in a continuous manner and connected to the segments A1 by the sensor 5414, to form a first pattern across the monitoring area of the substrate 5410. The arrows A1 and A2 indicate respective directions of conductive flow. From the viewpoint of FIG. 54, the arrangement of segments of the conductive trace 5412 forms an "M"-like pattern.

The electrically conductive trace 5418 is supported by the substrate 5410 and is connected to an input of the sensor 5414 as shown in greater detail in FIG. 55, described below. The electrically conductive trace 5418 includes a number of segments indicated by arrows B1, which are connected end-to-end in a continuous manner, and a number of segments indicated by arrows B2, which are connected end-to-end in a continuous manner, to form a second pattern across the monitoring area of the substrate 5410. The segments B1 are connected to the segments B2 by the sensor 5414. The segments (e.g., B1, B2) of the second pattern are spaced apart from the segments (e.g., A1, A2) of the first pattern by a distance, D1. The distance D1 between the segments of the second pattern and the segments of the first pattern is defined by one or more moisture management criteria. The moisture management criterion can include a moisture-related property of the substrate 5410. For example, a moisture management criterion may be a moisture-related property of the moisture absorbent material of the incontinence pad (such as a wicking or absorption property). In an illustrative example, the distance D1 is in the range of about 4 inches, based on a desired moisture sensitivity in the range of about 50 milliliters (e.g., D1 is the distance that 50 ml of liquid travels in the specified type of material forming the substrate 5410 or a layer of an incontinence pad in which the substrate 5410 is integrated). Thus, a notification may be issued by a notification device as described elsewhere herein, when the sensor 5414 detects an amount of moisture in the range of about 50 milliliters.

As shown in FIG. 54, some of the segments of the second pattern are interposed between two segments of the first pattern, while still being spaced apart from the segments of the first pattern by the distance, D1. For example, the second pattern as illustrated has a "U" shaped configuration, where segments of the "U" shape of the second conductive trace 5418 are interposed between segments of the "M" shape of the first conductive trace 5412. Further, some of the segments of the first conductive trace 5412 and the second conductive trace 5418 are connected to form an angle that is less than 180 degrees. For instance, in some cases, the ends of two segments (e.g., A1, A1 or B1, B1) are connected to form substantially a right angle (e.g., about 90 degrees). It should be understood, however, that while the segments (e.g., A1, A2, B1, B2) are shown in FIG. 54 as linear segments, any suitable spatial arrangement of the traces 5412, 5418 that maintains the desired spacing D1 between the traces 5412, 5418 may be used (e.g., curved, elliptical, or circular segments).

Each of the illustrative first and second electrically conductive traces 5412, 5418 comprises an electrically conductive material, and the electrically conductive material is coupled to a top surface of the substrate 5410 (e.g., a surface that faces upwardly away from a pad or mattress. For example, the electrically conductive material may be embodied as an electrically conductive ink, such as a silver ink, a copper ink, a carbon-carbon nanotube ink, or other conductive material suitable for performing the functions described herein. In some embodiments, the electrically conductive ink may be printed or painted directly on the substrate 5410.

Figure 55:
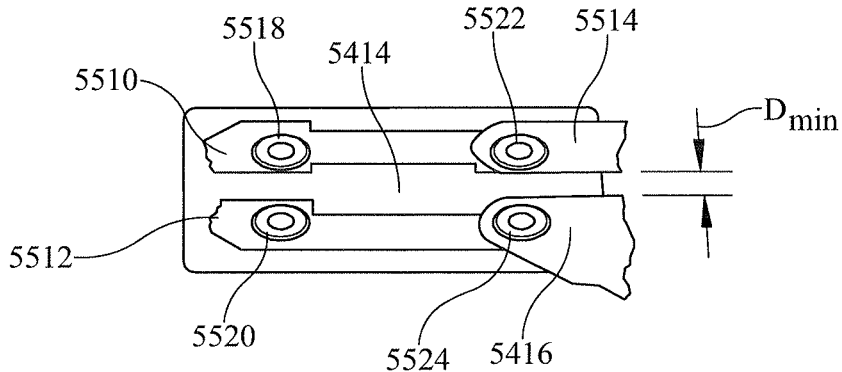
FIG. 55 is a simplified top plan view of a portion of the sensor sheet of FIG. 54, with a portion of a detuning material cut away to show connections of sensor traces to a sensor, as disclosed herein.

FIG. 55 is a simplified top plan view of a portion of the sensor sheet of FIG. 54, with a portion of the detuning material 5416 cut away to show connections of the sensor traces 5412, 5418 to the sensor 5414. In FIG. 55, trace ends 5510 and 5514 correspond to ends of segments B1 and B2 of the second trace 5418, and are connected to the sensor 5414 by connection points 5518, 5522, respectively. Similarly, trace ends 5512, 5516 correspond to ends of segments A1 and A2 of the first trace 5412, and are connected to the sensor 5414 by connection points 5520, 5524, respectively. The connection points 5514, 5516 connecting the trace ends 5514, 5516 to the sensor 5414 are separated by a gap having a size Dmin. Similarly, the connection points 5510, 5512 connecting the trace ends 5510, 5512 to the sensor 5414 are separated by a gap of the size Dmin. The gap size, Dmin, is defined to maintain at least a minimum distance between the first electrically conductive trace 5412 and the second electrically conductive trace 5418. The gap size, Dmin, is defined to prevent an electrical connection between the first electrically conductive trace 5412 and the second electrically conductive trace 5418 from occurring in the absence of a moisture event for which alerting is desired. In other words, the gap size Dmin, is defined to ensure that at least a minimum volume of moisture is present in the monitoring area before an alert is triggered.

Illustratively, the connection points 5518, 5520, 5522, 5524 connect the trace ends 5510, 5512, 5514, 5516 to the sensor 5414 by rivets. However, any suitable fastening mechanism capable of performing the functions described herein may be used alternatively or in addition to the rivets. For example, in some embodiments, the traces 5412, 5418 and the sensor 5414 may be connected in a continuous fashion (e.g., as a single, continuous printing on the substrate 5410).

Figure 56:
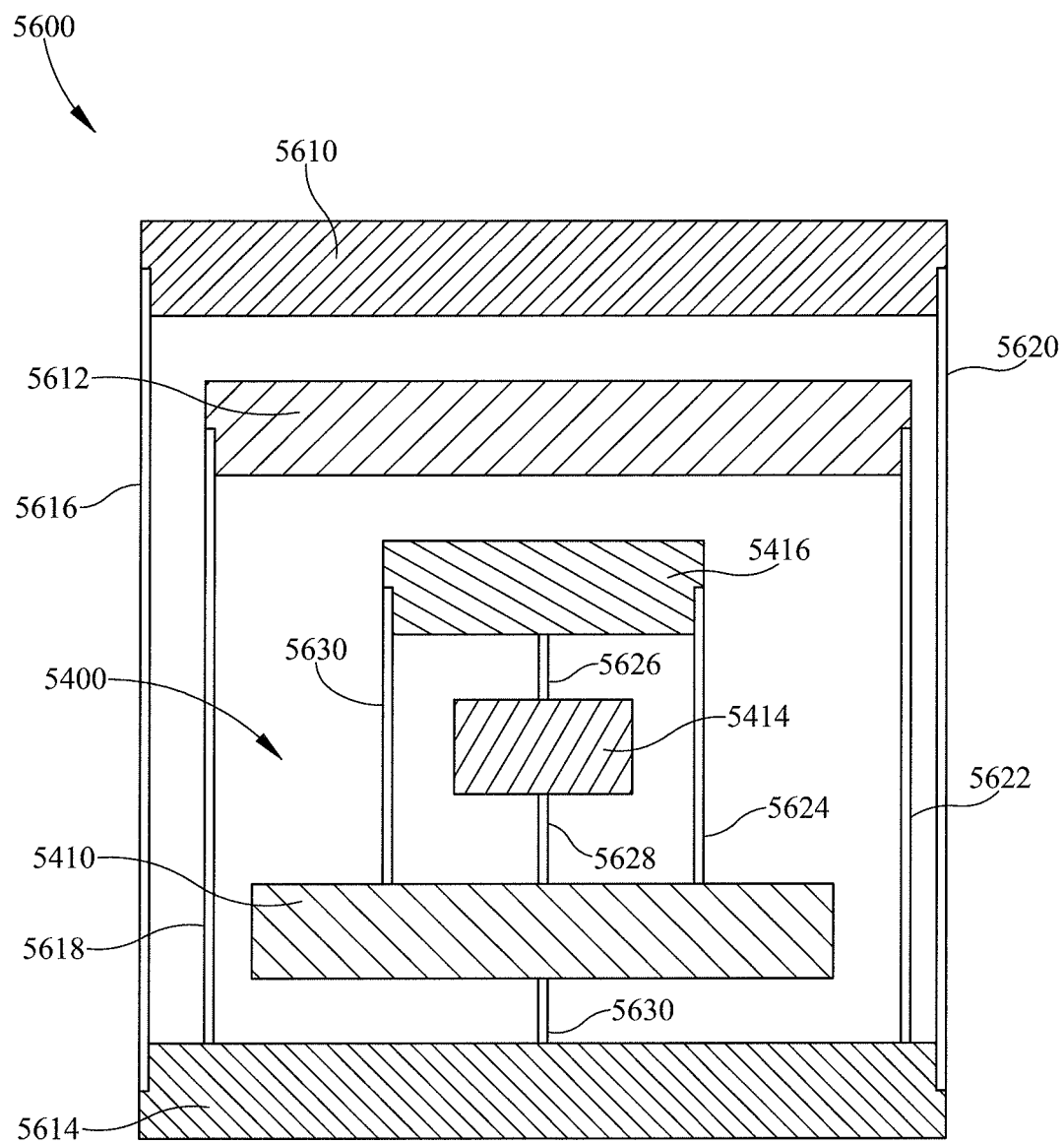
FIG. 56 is a simplified sectional view of the sensor sheet of FIG. 54, cut along the line 56-56, and also showing a similar view of at least one embodiment of a pad in which the sensor sheet may be incorporated.

FIG. 56 is a simplified sectional view of the sensor sheet of FIG. 54, cut along the line 56-56, and also showing a similar view of other components of at least one embodiment of an incontinence pad 5600 in which the sensor sheet may be incorporated. In the embodiment of FIG. 56, the pad 5600 includes a top layer 5610, a middle layer 5612, and a bottom layer 5614. The sensor sheet 5400 is disposed within the incontinence pad 5600, illustratively between the middle layer 5612 and the bottom layer 5614.

The illustrative top layer 5610 of the pad 5600 is made of a soft, water permeable nonwoven material. The middle layer 5612 is made of a moisture absorbent material. The materials used to construct the top layer 5610 and the middle layer 5612 are similar or identical to corresponding materials having the desired properties that are used in standard commercially available disposable incontinence pads. The layers of the pad 5600 are secured together by a number of fasteners 5616, 5618, 5620, 5622. Similarly, the components of the moisture management apparatus 5400 are secured to one another by a number of fasteners 5624, 5626, 5628, 5630. Additionally, the moisture management apparatus 5400 is secured to the bottom layer 5614 of the pad 5600 by a fastener 5632. The fasteners 5616, 5618, 5620, 5622, 5624, 5626, 5628, 5630, 5632 may be embodied as stitching, adhesive, and/or any other suitable fastening mechanism. While only one sensor sheet 5400 is shown in the pad 5600, it should be understood that the pad 5600 may include more than one sensor sheet 5400. For example, in some embodiments, two sensor sheets 5400 are layered above the bottom layer 5614 of the pad 5600 and arranged so that their corresponding sensors 5414 are located on opposite edges of the pad 5600 (e.g., away from the area of the pad 5600 that is most likely to be underneath the patient).

Figure 57:
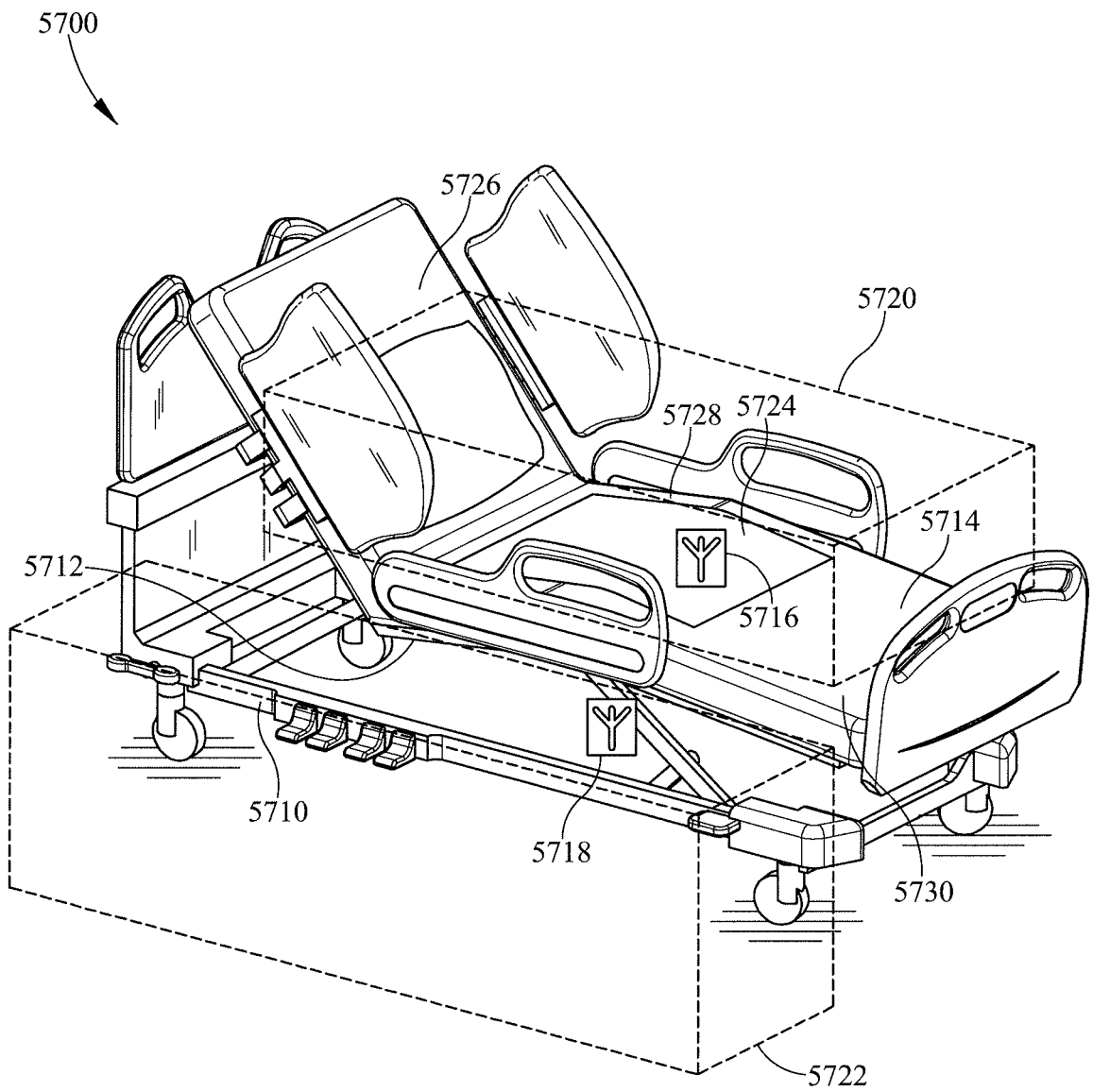
FIG. 57 is a simplified perspective view of at least one embodiment of a patient support apparatus, showing, schematically, sensor detection antennas and monitoring zones, as disclosed herein.

FIG. 57 is a simplified perspective view of at least one embodiment of a patient support apparatus 5700, showing, schematically, sensor detection antennas 5716, 5718, and sensor event monitoring zones 5720, 5722 adjacent the patient support apparatus 5700. The illustrative patient support apparatus 5700 includes a frame (e.g., 5710), a deck (e.g., 5712) supported by the frame 5710, and a patient support surface (e.g., a mattress) 5714 supported by the deck 5712. The patient support apparatus 5700 is capable of supporting a patient in at least a horizontal position. In some embodiments, the antenna 5716 is coupled to a top surface of the deck, underneath the mattress 5714. The antennas 5716, 5718 are configured to wirelessly receive sensor signals emitted by a sensor (e.g., the sensor 5414), and wirelessly transmit the sensor signals to a reader (e.g., reader 5980 shown in FIG. 59, described below). The illustrative sensor signals are emitted by the sensor (e.g., the sensor 5414) in response to a moisture event occurring in a moisture event monitoring area located adjacent the deck 5712, and as such the sensor signals include data indicative of the moisture event. However, as described further below, the antennas 5716, 5718 may be configured to wirelessly receive and wirelessly transmit other types of sensor signals, or sensor signals from other types of sensors (e.g., bed exit detection sensors, siderail down sensors, patient fall sensors, etc.), alternatively or in addition to the moisture event monitoring sensor signals.

In the illustrative patient support apparatus 5700, the deck 5712 includes a head section 5726, a foot section 5730, and a seat section 5728, where the seat section 5728 is located between the head section 5726 and the foot section 5730. In some embodiments, the antenna 5716 is mounted to a top surface of the seat section 5728 of the deck 5712, e.g., underneath the mattress 5714, or between the deck 5712 and the mattress 5714. An incontinence pad 5724 (e.g., the pad 5600) is positioned on the mattress 5714 above the seat section 5728 of the deck 5712. Thus, a sensor (e.g., the sensor 5414) for detecting moisture events is located in the seat section of the patient support apparatus 5700 when the incontinence pad 5724 is present.

The antenna 5718 is illustratively mounted to the frame 5712. The antenna 5718 is configured to wirelessly receive a sensor signal emitted by a sensor located in a different monitoring area than the area monitored by the antenna 5716. For example, the antenna 5718 has a monitoring zone 5722, while the antenna 5716 has a monitoring zone 5720. A reader (e.g., the reader 5980) can selectively vary an amount of power supplied to each of the antennas 5716, 5718 to adjust the size of the area in which sensor signals can be read by one or more of the antennas 5716, 5718 (e.g., a "read range"), in accordance with different patient monitoring needs. Illustratively, the zone 5720 of the antenna 5716 extends along the length of the mattress 5714 (e.g., outside the footprint of the antenna 5716) (e.g., longitudinally from the head to the foot of the bed; for example, within a range of about 18 inches of the head end edge to about 12 inches of the foot end edge), across the width of the mattress 5714 (e.g., ending at the lateral edge of the antenna 5716, or, horizontally from edge-to-edge of the surface), and up a distance in the range of about 18 inches away from the antenna 5716, which is mounted to the deck 5712 (e.g., by a distance sufficient to extend from the antenna 5716 to the top of any mattress of varying thickness, along with any cushions, pillows, wedges, or other items that might be on top of the mattress and on which the patient is being supported).

Illustratively the zone 5722 of the antenna 5718 extends along the length of the mattress 5714 (e.g., longitudinally from the head end to the foot end of the bed), down a vertical distance toward the floor (e.g. where the vertical distance is less than or equal to a height of the patient support apparatus 5700 above the floor, where the height may be measured from the bottom of the mattress 5714 to the floor), and extends in a horizontal direction away from the side of the patient support apparatus 5700 a distance in the range of about 36 inches from the edge of the bed. The illustrative antennas 5716, 5718 are embodied as passive radio frequency (RF) antennas configured to operate at a power level to receive sensor signals emitted by sensors within their respective zones 5720, 5722. Alternatively or in addition, the antennas 5716, 5718 are configured to read sensor signals at a specific frequency, such as a frequency configured for monitoring moisture events, fall events, and/or other types of sensed patient monitoring events.

Figure 58:
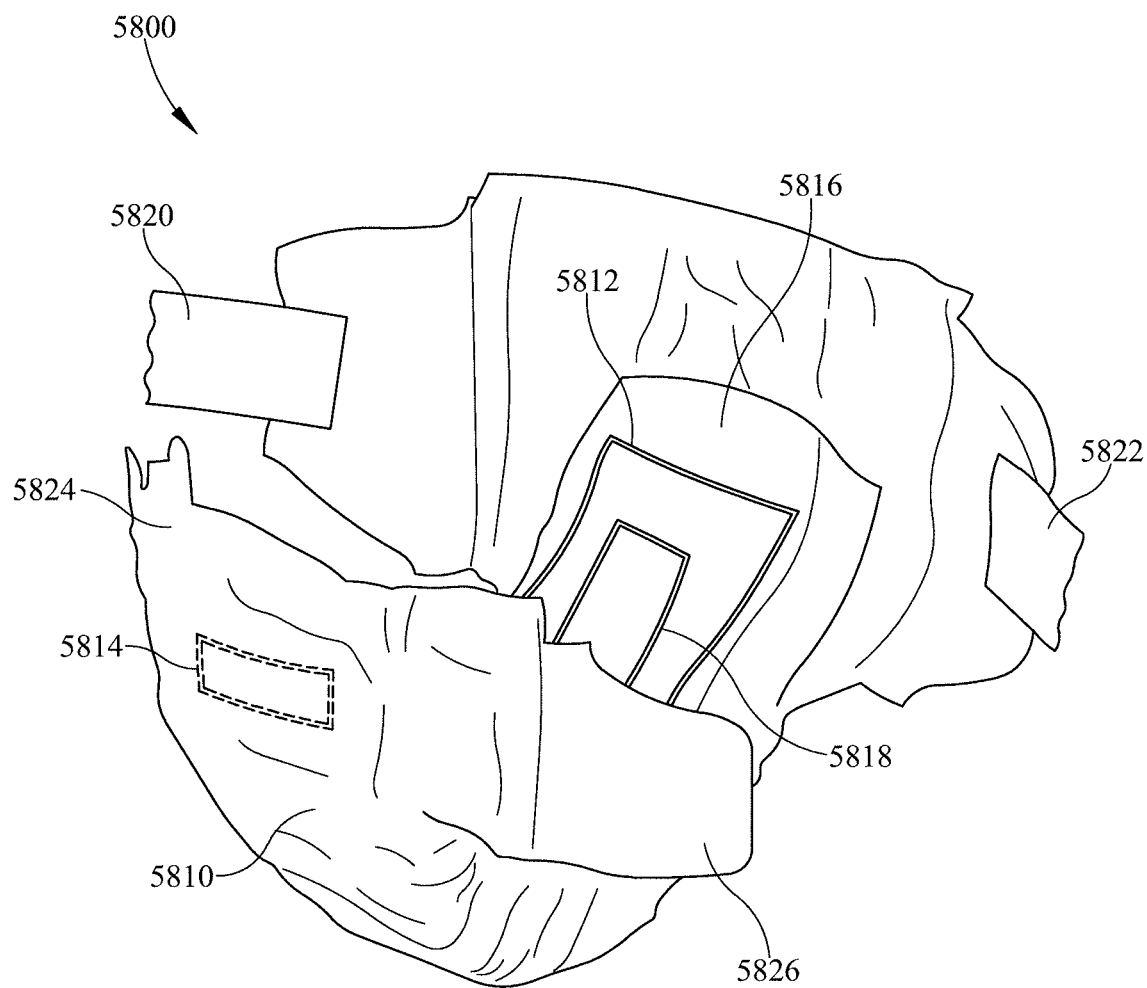
FIG. 58 is a simplified perspective view of at least one embodiment of a wearable pad including a sensor sheet, as disclosed herein.

FIG. 58 is a simplified perspective view of at least one embodiment of a wearable incontinence pad 5800 including an embodiment of the sensor sheet 5400, as disclosed herein. The pad 5800 is embodied as a diaper or disposable undergarment. The pad 5800 has a cross section similar to that shown in FIG. 56. The illustrative pad 5800 includes a bottom layer 5810, which is made of a water impermeable plastic film, and a top layer 5816, which is made of a water permeable nonwoven material. Differently-charged electrically conductive traces 5812, 5818 are printed with electrically conductive ink on the top layer 5816. The traces 5812, 5818 may be printed on another layer located between the top layer 5816 and the bottom layer 5810, in other embodiments. The traces 5812, 5818 are connected to a sensor 5814 in a manner similar to that described above with reference to FIG. 55. The sensor 5814 is embodied as, for example, the sensor 5414. The pad 5800 includes a number of fastening tabs 5820, 5822, 5824, 5826, which allow the top portion of the pad 5800 to be secured around a patient's waist or hips (e.g., in a belt-like fashion).

Figure 59:
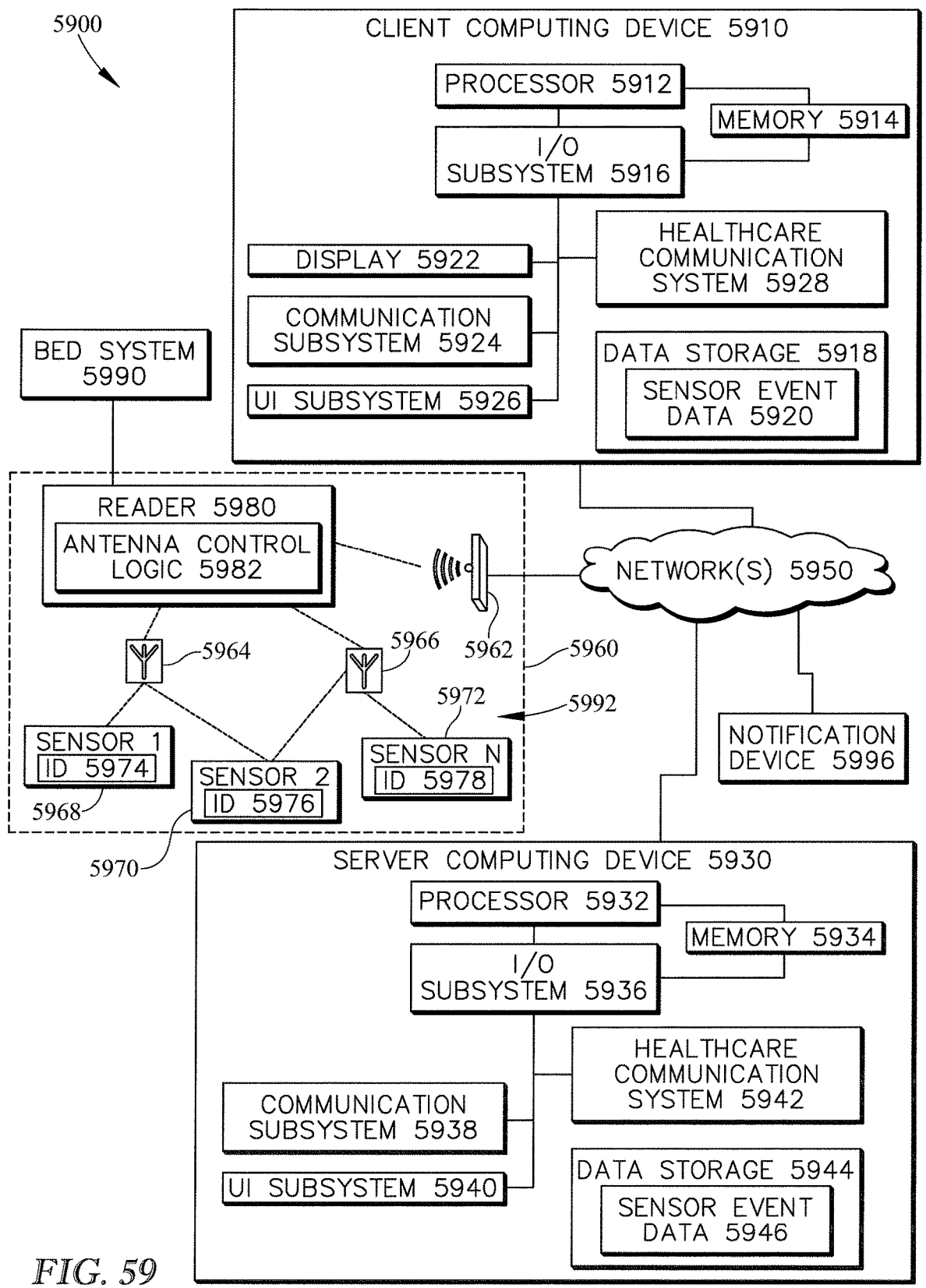
FIG. 59 is a simplified block diagram of at least one embodiment of a computing system including sensor event detection features as disclosed herein.

FIG. 59 is a simplified block diagram of at least one embodiment of a computing system 5900 including sensor event detection features. The computing system 5900 is similar to the computing system 4900 described above, except that the computing system 5900 can monitor for moisture events and other types of sensor events, such as bed exit events, patient fall events, siderail down events, and/or others. The computing system 5900 includes a client computing device 5910, one or more network(s) 5950, one or more notification devices 5996, a server computing device 59, and a sensor event communication system 5992. In general, components of the computing system 5900 having the same or similar name as components of the computing system 4900 may be embodied similarly. For example, the client computing device 5910 may be embodied in a similar manner as the client computing device 4910, and the same applies for other components such as the network(s) 5950, the server computing device 5930, the wireless access point 5962, and the bed system 5990. Accordingly, the description of those components is not repeated here.

A sensor event communication system 5992 facilitates the communication of wireless sensor signals from a number of different patient monitoring sensors 1 to N (where N is a positive integer) 5968, 5970, 5972 located in an area 5960, to another electronic device, such as the client computing device 5910, the server computing device 5930, or one or more notification devices 5996 (e.g., a dome light, a wall mounted display, a nurses station, a caregiver display or visual indicator located on a patient support apparatus, a mobile computing device (such as a tablet computer or smart phone), and/or others.

The reader 5980, mentioned above, may be embodied as, for example, a transceiver (e.g., transceiver 112), a multiplexer (e.g., multiplexer 130), a controller (e.g., circuitry or microprocessor 120), or a combination of these components and/or other components. The reader 5980 includes antenna control logic 5982. The antenna control logic 5982 is embodied as software, firmware, or hardware of the reader 5980, and controls power to a number of antennas (e.g., antennas 5964, 5966) to selectively establish or adjust the monitoring zones of each of the antennas 5964, 5966 (where each of the monitoring zones may include all or a portion of the area 5960). The reader 5980 also includes control logic to communicate with the sensors 5968, 5970, 5972 (using, e.g., an interrogation technique as described above), in order to verify or authenticate the sensors 5968, 5970, 5972 as being permitted to communicate sensor signals to other components of the computing system 5900, and/or to control or adjust the frequency at which each or any of the sensors 5968, 5970, 5972 issues sensor signals. The various control logic of the reader 5980 is embodied as software, firmware, or hardware (e.g., electrical circuitry). Each of the sensors 5968, 5970, 5972 includes an authentication mechanism 5974, 5976, 5978, such as a unique identifier or authentication code. The authentication mechanism 5974, 5976, 5978 is embodied as software, firmware, or hardware in the sensor 5968, 5970, 5972. For example, the authentication mechanism 5974, 5976, 5978 may be embodied as data or programming code stored in a non-transitory computer readable storage medium (e.g., computer memory or data storage) of the sensor 5968, 5970, 5972. The authentication mechanism 5974, 5976, 5978 is configured to wirelessly communicate sensor authentication information for receipt by another device (such as the reader 5980 or another component of the computing system 5900).

In some embodiments of the sensor event communication system 5992, the reader 5980 wirelessly receives sensor signals from the antennas 5964, 5966, and transmits the sensor signals received from the antenna to the notification device 5996. In some embodiments, the antennas 5964, 5966 are configured to wirelessly receive a sensor identifier signal emitted by the sensor and the reader is configured to verify the sensor identifier signal; and, in response to the verification of the sensor identifier signal, transmit the sensor signal received by the antenna to the notification device 5996. In some embodiments, the reader 5980 or more specifically the antenna control logic 5982 selectively controls the power to the antennas 5964, 5966 and selectively controls the frequencies at which the sensors 5968, 5970, 5972 emit sensor signals in accordance with antenna power requirements and sensor frequency requirements, which may be general requirements that apply to all wireless transmissions (e.g., SARS regulations) or more specific requirements for monitoring particular types of sensor events. For example, the reader 5980 may issue periodic "bursts" of higher power levels in order to expand an antenna's reading range to encompass a number of different sensors that may be located in the area 5960 (e.g., in order to determine how many different sensors there are and the types of sensors). As another example, the reader 5980 may read different frequencies for different types of monitoring events. In some embodiments, the reader 5980 determines and sets a frequency at which the reader 5980 communicates sensor signals emitted by a sensor 5968, 5970, 5972 to the notification device 5996 (or another component of the computing system 5900) based on a characteristic of a patient associated with the sensor 5968, 5970, 5972 or based on a characteristic of a caregiver associated with the patient that is associated with the sensor 5968, 5970, 5972, such that the reader 5980 transmits sensor signals from the sensor 5968, 5970, 5972 to the notification device 5996 more frequently for some patients than for other patients, or more frequently for some caregivers than for other caregivers.

Figure 60:
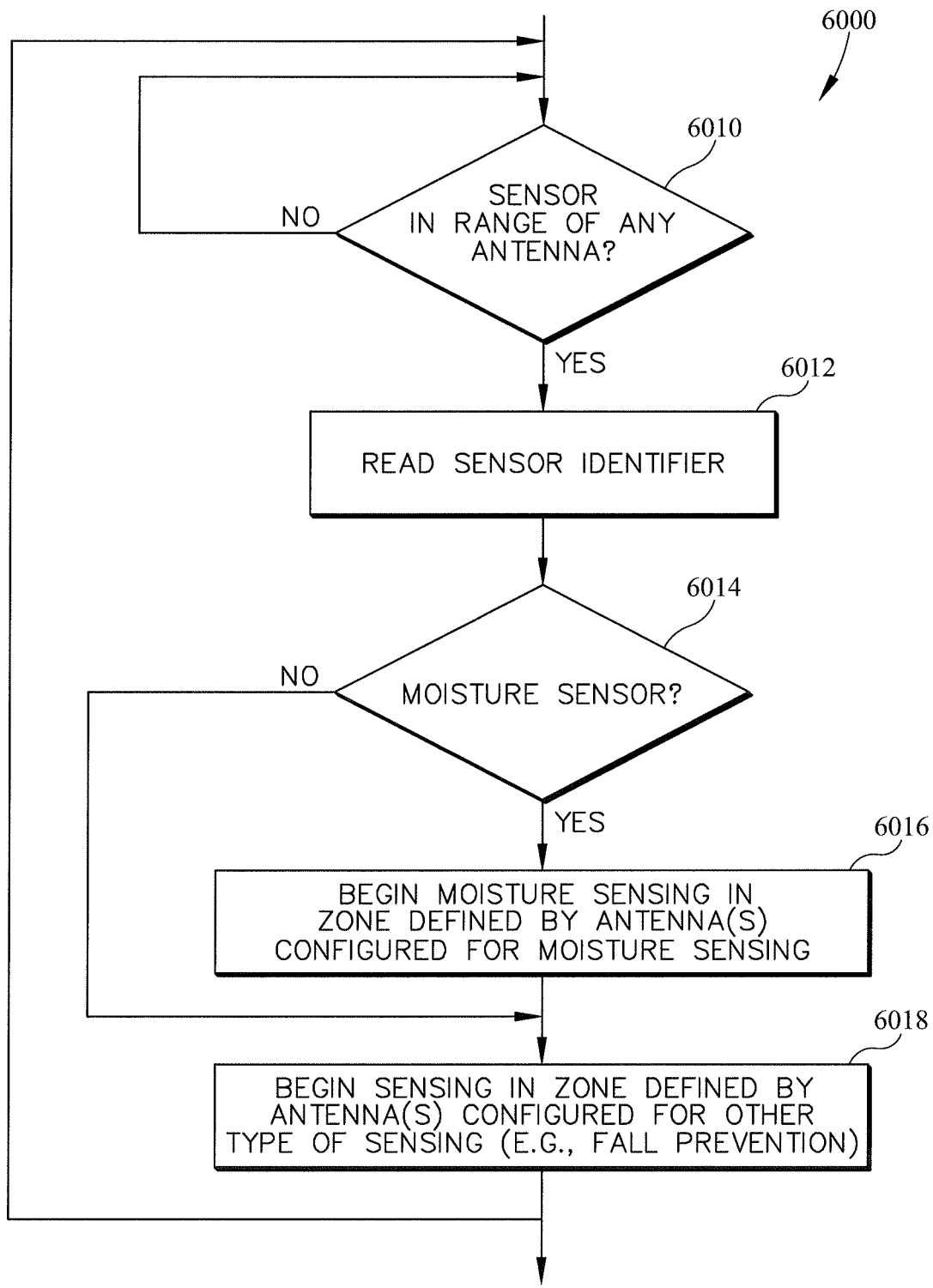
FIG. 60 is a simplified flow diagram of a sensor detection process that may be executed by a computing system, as disclosed herein.

FIG. 60 is a simplified flow diagram of a sensor detection process 6000 that may be executed by, for example, one or more components of the computing system 5900. Portions of the sensor detection process 6000 may be embodied in, for example, computer code and/or electrical circuitry. In block 6010, the computing system 5900 detects whether a sensor is in range of any of the antennas in the monitoring area (e.g., the antennas 5964, 5966). To do this, the computing system 5900 may increase the power to the antennas 5964, 5966 temporarily. If any of the antennas detect a sensor, the process 6000 proceeds to block 6012. If no sensors are detected by any of the antennas, the process returns to block 6010. In block 6012, the computing system 5900 (e.g., the reader 5980) reads a sensor identifier portion of the sensor signals received from the sensors detected within range of one or more of the antennas in block 6010. In block 6014, the computing system 5900 (e.g., the reader 5980) determines whether the sensor identifier read in block 6012 indicates that the sensor is a moisture sensor (e.g., configured to detect moisture events). To do this, the computing system 5900 may utilize a mapping table or database to match the sensor identifier with corresponding sensor type and/or antenna information stored in the mapping table or database. Alternatively, the sensor type information may be part of the sensor identifier, in which case the computing system 5900 may parse the sensor identifier to extract the sensor type information and match it with the appropriate antennas. If the computing system 5900 determines in block 6014 that the sensor is a moisture sensor, the process 6000 processes to block 6016. If the computing system 5900 determines that the sensor is not a moisture sensor, the process 6000 jumps to block 6018. In block 6016, the computing system 5900 determines the antennas for moisture sensing and begins executing the moisture sensing functions using the antenna(s) that are configured for moisture sensing. To do this, the computing system 5900 powers the antennas located in the moisture sensing zone at the power level specified for moisture sensing. For example, in the embodiment of FIG. 57, antenna 5716 may be activated to monitor wireless signals from a sensor in the pad 5724 to detect moisture events in the zone 5720. Following block 6014 or block 6016, as the case may be, in block 6018, the computing system 5900 determines the appropriate antennas and begins executing the sensing functions for another type of sensing based on the sensor type determined in block 6014 or a "default" sensor type. For example, in the embodiment of FIG. 57, antenna 5718 may be activated to monitor wireless signals from a body-worn sensor configured for fall prevention (such as fall prevention socks), to detect fall risk events in the zone 5722. Following block 6018, the computing system 5900 may return to block 6010 to re-initiate the process 6000. While not specifically shown in FIG. 60, it should be understood that the sensing operations initiated at block 6016 and block 6018 may be preceded by a sensor authentication process. For example, the computing system 5900 may verify the identification signal in block 6012, and if the identification signal is successfully verified, initiating the monitoring for sensor events based on the sensor type in block 6016 and/or block 6018.

Figure 61:
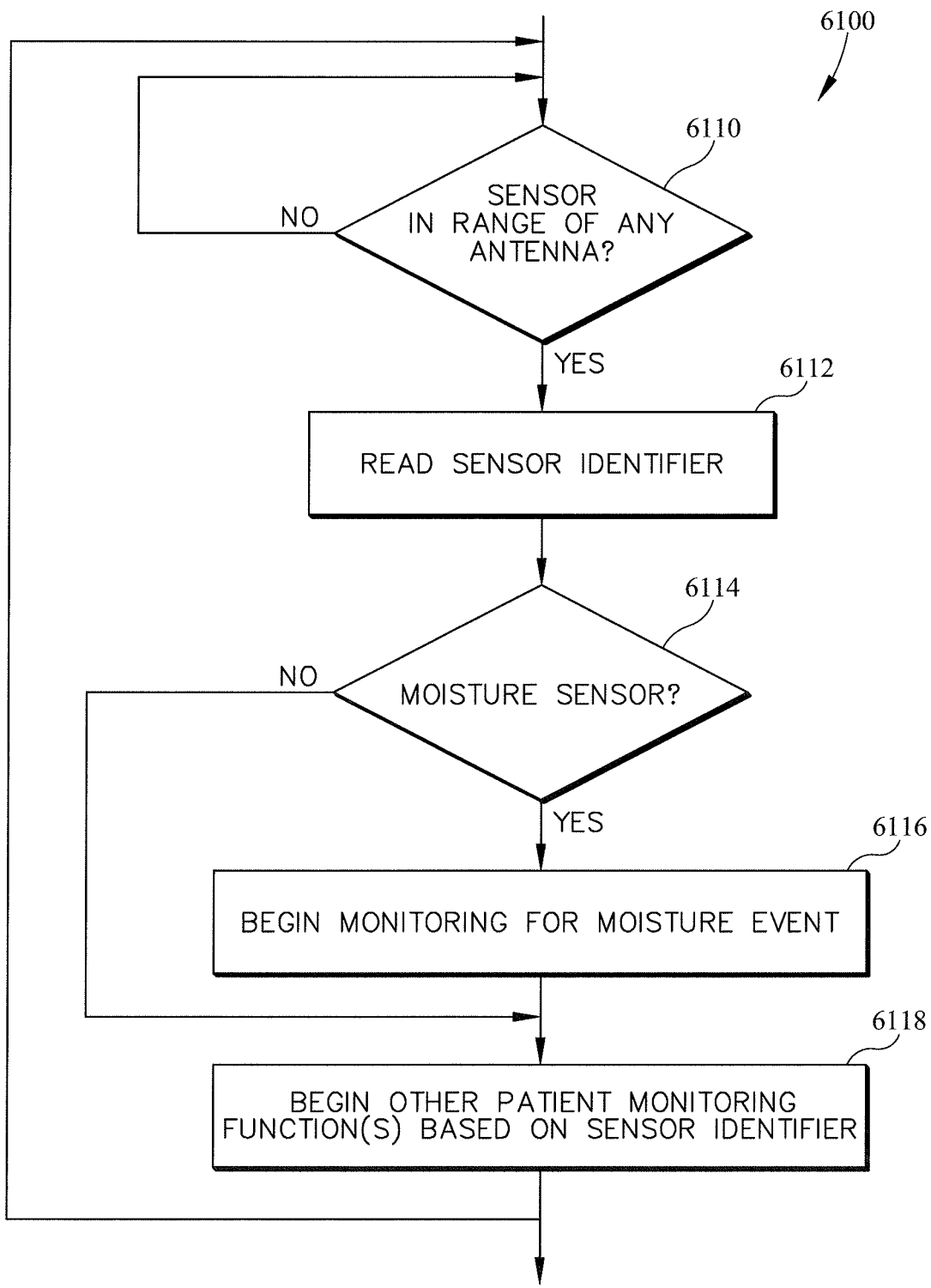
FIG. 61 is a simplified flow diagram of a sensor detection process that may be executed by electrical circuitry, as disclosed herein.

FIG. 61 is a simplified flow diagram of a sensor detection process 6100 that may be executed by, for example, one or more components of the computing system 5900. Portions of the sensor detection process 6100 may be embodied in, for example, computer code and/or electrical circuitry. The process 6000 described above involves multiple antennas and making determinations as to which antennas to use to monitor sensor signals. In the process 6100, and antenna detects a sensor within the antenna's read range, in block 6110. The process 6100 remains in block 6110 unless/until a sensor is detected. If a sensor is detected in the antenna's range, the process 6100 proceeds to block 6112. In block 6112, the computing system 5900 (e.g., the reader 5980) reads a sensor identifier portion of the sensor signal emitted by the sensor In block 6114, the computing system 5900 determines, based on the information read in block 6112, whether the sensor is a moisture sensor or some other type of sensor. If the sensor is a moisture sensor, the process 6100 proceeds to block 6116. If the sensor is not a moisture sensor, the process 6100 proceeds to block 6118. In block 6116, the computing system 5900 begins monitoring for moisture events using the antenna of block 6110. To do this, the computing system 5900 may: read the sensor signals periodically (e.g., every 30 seconds) and execute a moisture detection algorithm using the read sensor signal (which may be indicative of, for example, a change in RSSI) as an input to the moisture detection algorithm. Following block 6116 or block 6114, as the case may be, in block 6118, the computing system 5900 begins another type of patient monitoring, in accordance with the sensor identifier read in block 6112. As an example, the computing system 5900 may have identified the sensor as a patient ID wristband, in block 6112. Accordingly, in block 6118, the computing system 5900 may begin executing a patient tracking function. For example, the computing system 5900 may: read the sensor signal periodically (e.g., every 10 minutes), and/or read the sensor signal if the patient weight measured by a weigh scale (e.g., a weigh scale built in to the patient support apparatus 5700), and/or read the sensor signal if a bed exit is detected, and/or read patient identifying information (e.g., read the patient's name from sensor identifier or from a database (where the patient's name may be associated with the sensor identifier in the database), and then display the patient's name on a display device, such as a display device of the patient support apparatus 5700), and/or read fall risk data from the sensor and/or a database (where the fall risk data may be associated with the sensor identifier in the database) and initiate a fall prevention protocol if the fall risk data indicates that the patient is at risk of falling. The computing system 5900 may adjust the read range of the antenna as needed to perform the requisite data read functions. The process 6100 illustrates that the same antenna, or even the same sensor in some cases, can be used to perform multiple different types of patient monitoring.

Figure 62:
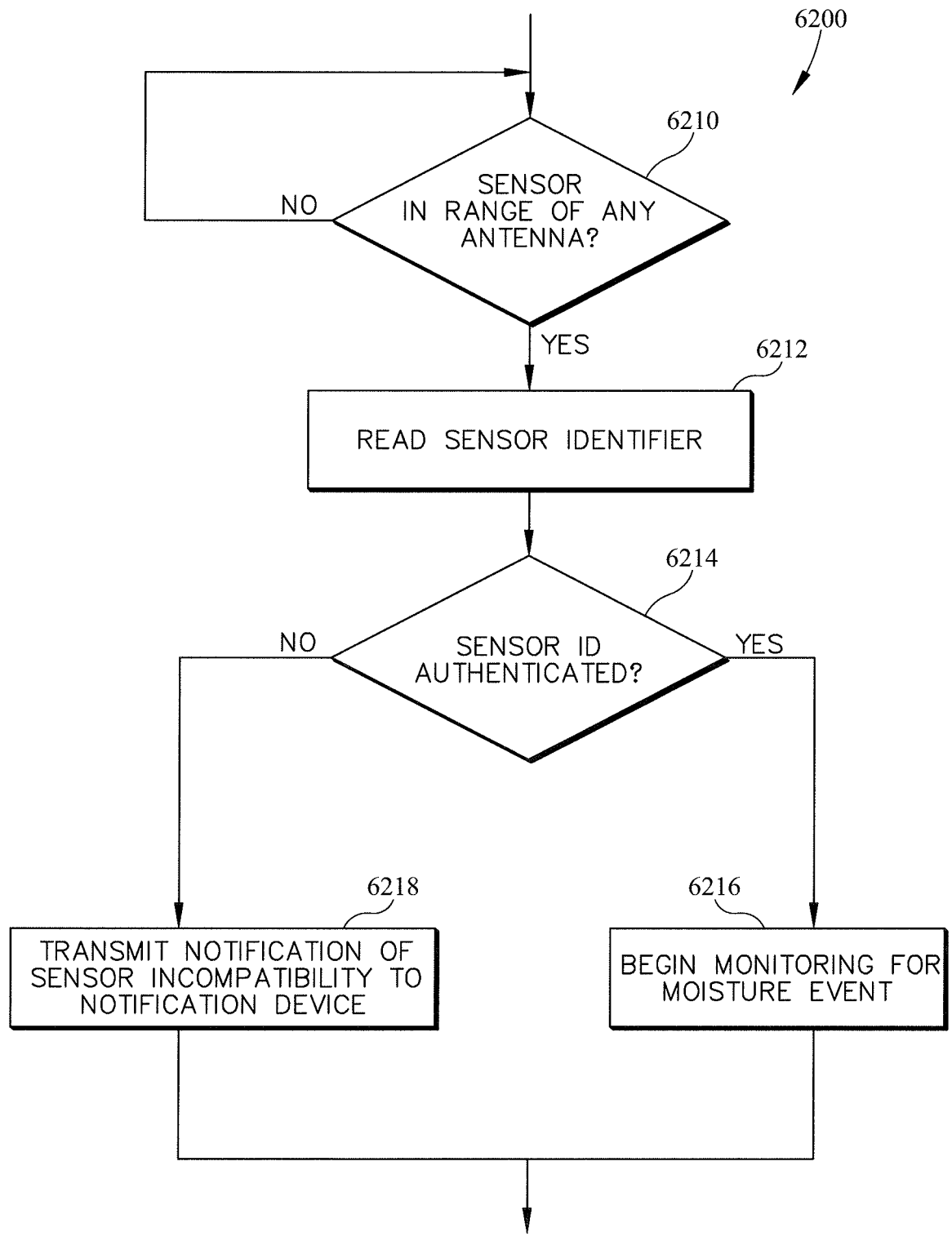
FIG. 62 is a simplified flow diagram of a sensor authentication process that may be executed by electrical circuitry, as disclosed herein.

FIG. 62 is a simplified flow diagram of a sensor authentication process 6200 that may that may be executed by, for example, one or more components of the computing system 5900. Portions of the sensor authentication process 6200 may be embodied in, for example, computer code and/or electrical circuitry. In block 6210, the computing system 5900 determines whether a sensor (e.g., any of the sensors disclosed herein) is within range of an antenna (e.g., any of the antennas disclosed herein). The process 6200 remains in block 6210 unless/until a sensor is detected within the antenna's read range. If a sensor is detected at block 6210, the process 6200 reads the sensor identifier in block 6212. In block 6214, the computing device 5900 determines if the sensor identifier read in block 6212 is valid. To do this, the computing device 5900 may, for example, access a database or lookup table of valid sensor identifiers and determine if the sensor identifier read in block 6212 is listed in the database or lookup table. If the computing device 5900 successfully verifies the sensor in block 6214, the computing system 5900 begins moisture event monitoring with the verified sensor in block 6216. If the sensor is not successfully verified, the computing device transmits a notification indicating the sensor incompatibility (or failure to validate) to a notification device (e.g., a notification device 5996, a client computing device 5910, etc.). Following block 6216 or block 6218, as the case may be, the computing system 5900 may return to block 6210 or the process 6200 may end.

Figure 63:
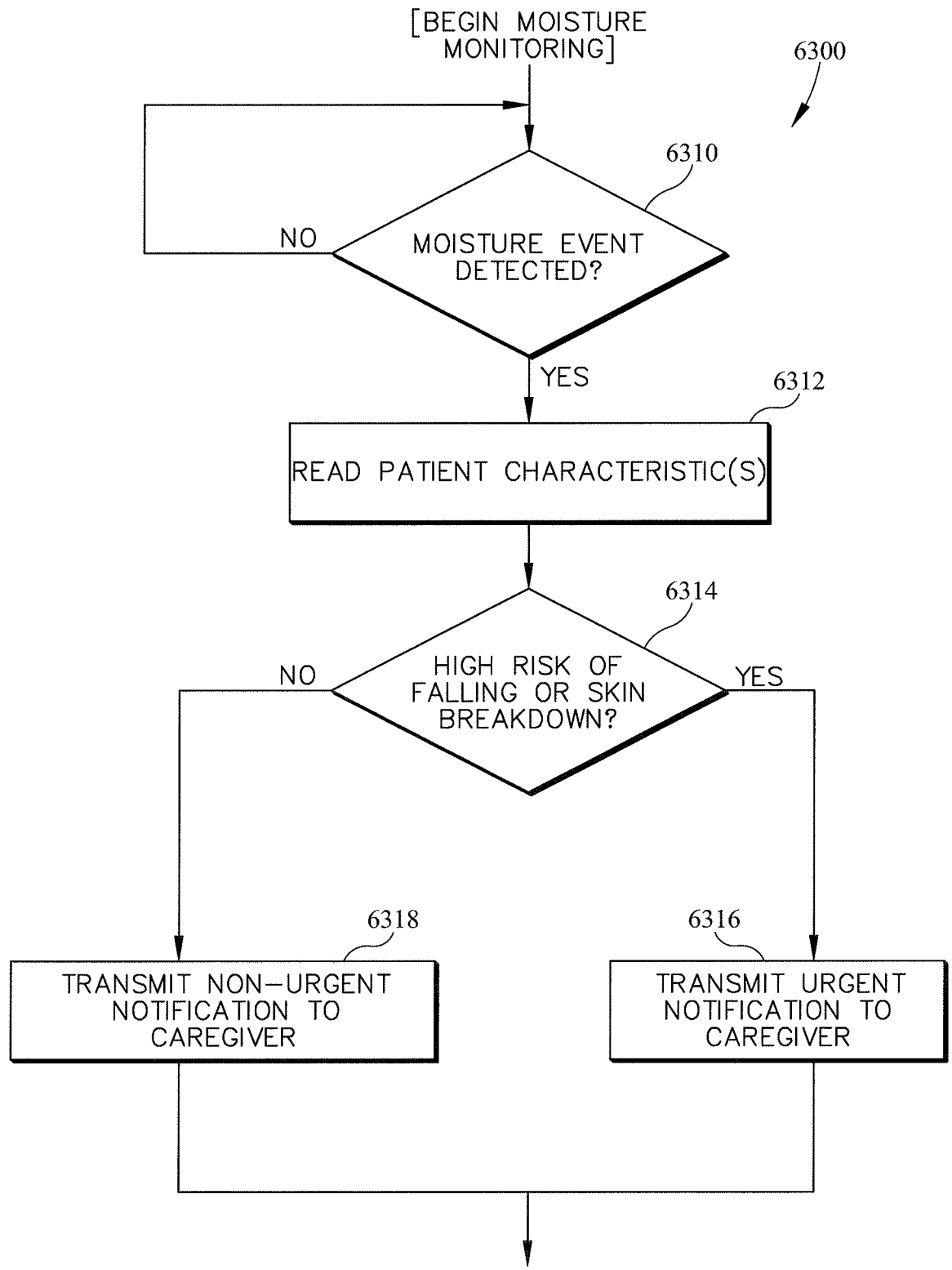
FIG. 63 is a simplified flow diagram of a sensor event notification process that may be executed by electrical circuitry, as disclosed herein.

FIG. 63 is a simplified flow diagram of a sensor event notification process 6300 that that may be executed by, for example, one or more components of the computing system 5900. Portions of the sensor event notification process 6300 may be embodied in, for example, computer code and/or electrical circuitry. The process 6300 occurs after the computing system 5900 has already begun moisture event monitoring. In block 6310, the computing device 5900 determines whether a moisture event is detected by a sensor (e.g., any of the moisture detection sensors described herein). To do this, the computing device 5900 may, for example, compare a characteristic of the sensor signal (e.g., RSSI) to a known value indicative of a moisture event. Of course, the computing device 5900 may execute any of the moisture detection algorithms disclosed herein. The process 6300 remains in block 6310 if no moisture event is detected. If a moisture event is detected, the computing system 5900 proceeds to block 6312 and reads on or more patient characteristics of a patient using the moisture monitoring sensor. To do this, the computing system 5900 may map a portion of the sensor signal (e.g., a sensor identifier) to a lookup table or query a database to obtain the patient characteristic information for the patient associated with the sensor. The patient characteristic may include, for example, indications of whether the patient is at risk of falling or whether the patient is at risk of having his or her skin break down (e.g., to form pressure sores). In block 6314, the computing system 5900 determines whether the patient whose characteristics are read in block 6312 has a risk of falling or skin breakdown. If the patient has neither a risk of falling nor a risk of skin breakdown, the computing system 5900 transmits a non-urgent notification to a caregiver, in block 6318. If the patient does have a risk of falling or a risk of skin breakdown (or both), the computing system 5900 transmits an urgent notification to the caregiver. Following block 6316 or block 6318, as the case may be, the computing system 5900 may return to block 6310 or end the process 6300.

Some of the above embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more processors, microprocessors or other control devices. Similarly, where the elements of the above embodiments are implemented using software programming or software elements the embodiments may be implemented with any programming or scripting language such as C, C++, Java, assembler, or the like, with the various algorithms being implemented with any combination of data structures, objects, processes, routines or other programming elements. Furthermore, the embodiments could employ any number of conventional techniques for electronics configuration, signal processing and/or control, data processing and the like. The word mechanism may be used broadly and is not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical." Numerous modifications and adaptations will be readily apparent to those skilled in this art without departing from the spirit and scope of the embodiments.

The order of execution or performance of the operations in embodiments illustrated and described herein is not essential, unless otherwise specified. That is, the operations may be performed in any order, unless otherwise specified, and embodiments as described may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and/or described herein. Other embodiments may include different computer-executable instructions or components having more or less functionality than illustrated and described herein.

Many other embodiments of the present disclosure are also envisioned. For example, a moisture management apparatus includes a plurality of layers of fabric material comprising a lower layer, a middle layer supported by the lower layer, and an upper layer supported by the middle layer, wherein the upper layer comprises an upper surface configured to interface with a body portion of a person, and the upper surface comprises a hydrophilic material; the upper layer comprises a lower surface opposite the upper surface, and the lower surface comprises a hydrophobic material; the middle layer comprises material that is configured to transfer moisture away from the upper surface and toward the lower layer; the lower layer comprises an upper surface, and the upper surface of the lower layer comprises a hydrophobic material; and a sensor positioned in the lower layer, wherein the sensor is configured to wirelessly indicate the presence of moisture in the moisture management apparatus to another device.

In the moisture management apparatus, the lower layer may include an absorbent material proximate the sensor. In the moisture management apparatus, at least the middle layer may include a moisture-wicking fabric. In the moisture management apparatus, at least the middle layer may include a plurality of three-dimensional fibers arranged to direct moisture toward the lower layer. In the moisture management apparatus, the sensor may include a radio frequency identification (RFID) sensor to receive a signal generated by a transceiver that is spaced from the moisture management apparatus and transmit a response to the reference signal to the transceiver. In the moisture management apparatus, the upper and lower layer may cooperate to define an enclosed interior region comprising the middle layer. In the moisture management apparatus, the sensor may wirelessly indicate the presence of moisture in the moisture management apparatus to another device that is spaced from the sensor.

In another example, a moisture management apparatus includes a plurality of layers of fabric material including an upper layer configured to interface with a body portion of a person, and a lower layer spaced from the upper layer by a middle layer, wherein the lower layer has a greater ability to absorb moisture than either the middle layer or the upper layer; and a sensor positioned in the lower layer; where the sensor is to wirelessly indicate the presence of moisture in the moisture management apparatus to another device.

The moisture management may include a disposable pad. The moisture management apparatus may include a reusable pad. In the moisture management apparatus, a different physico-chemical modification may be applied to each of the upper layer, the middle layer, and the lower layer to provide a moisture absorption gradient configured to direct moisture away from the upper surface of the upper layer and toward the lower layer. In the moisture management apparatus, each of the upper layer, the middle layer, and the lower layer has a different structural arrangement of fibers to provide a moisture absorption gradient configured to direct moisture away from the upper surface of the upper layer and toward the lower layer. In the moisture management apparatus, the lower layer may have a greater ability to absorb moisture than the middle layer, and the middle layer has a greater ability to absorb moisture than the upper layer.

In another example, a moisture management apparatus includes a layer of fabric material comprising an arrangement of fluid conducting pathways, each of the fluid conducting pathways to direct fluid to a fluid collecting region of the layer of material; and a sensor positioned in the fluid collecting region; where the sensor is configured to wirelessly indicate the presence of moisture in the moisture management apparatus. In the moisture management apparatus, the layer of fabric material may include a surface modified by a physio-chemical treatment to define the fluid conducting pathways. In the moisture management apparatus, the layer of fabric material may include a plurality of fibers arranged to define the fluid conducting pathways. In the moisture management apparatus, the layer of material may include a plurality of contiguous edges defining a perimeter of the moisture management apparatus, where the fluid collecting region is positioned adjacent one of the edges, and the fluid conducting pathways are configured to direct moisture toward the fluid collecting region. In the moisture management apparatus, the fluid conducting pathways are arranged as rays emanating from the fluid collecting region across the layer of fabric material. In the moisture management apparatus, the layer of material may include a plurality of contiguous edges defining a perimeter of the moisture management apparatus, where the fluid collecting region is spaced from the edges in a central region of the moisture management apparatus, and the fluid conducting pathways are configured to direct moisture toward the sensor. In the moisture management apparatus, the fluid conducting pathways are arranged as closed shapes emanating concentrically from the fluid collecting region toward the perimeter of the moisture management apparatus.

In another example, a moisture management apparatus includes a plurality of layers of fabric material, comprising an upper layer, a lower layer, and a middle layer separating the upper layer from the lower layer, wherein: the upper layer has an upper surface configured to interface with a body portion of a person; the upper layer comprises a moisture absorbent material; and the middle layer comprises a moisture impermeable material; a first sensor positioned in the upper layer, wherein the first sensor is configured to wirelessly indicate the presence of moisture in the upper layer to another device; and a second sensor positioned in the lower layer, wherein the second sensor is to wirelessly indicate the presence of the moisture management apparatus to the other device.

The moisture management apparatus may include a transceiver to transmit wireless signals for receipt by the first sensor and the second sensor, where the first sensor is positioned so that when a moisture event occurs, moisture in the upper layer prevents the wireless signals from being received by the first sensor. In the moisture management apparatus, the plurality of layers of fabric material may cooperate to define a pad, and the transceiver may be coupled to a support surface that supports the pad. In the moisture management apparatus, the support surface may include a deck section of a person support apparatus. In the moisture management apparatus, the first sensor and the second sensor may include radio frequency identification (RFID) sensors.

EXAMPLE CLAUSES

RSSI Based Method of Sensor Interrogation for Detecting Incontinence or Other Moisture Caused Abnormality Clause 1. A method of detecting the presence of moisture on an occupant support, the method including A) providing one or more moisture responsive sensors in a surveillance zone of the occupant support; B) exciting the one or more sensors with an electromagnetic signal; C) monitoring for a response from the one or more sensors; D) comparing the response to an expected response; and E) based on the comparing of the response to the expected response, issuing a first output.

Clause 1.1. A method of interrogating one or more sensors to detect the presence of moisture on an occupant support including: A) providing one or more moisture responsive sensors in a surveillance zone of the occupant support, the one or more sensors being tuned to a center frequency; B) exciting the one or more sensors with an electromagnetic signal having a frequency approximately equal to the center frequency; C) monitoring for a center frequency response from the one or more sensors; D) comparing the center frequency response to an expected center frequency response; and E) if the center frequency response compares favorably to an expected center frequency response, issuing a first output consistent with the favorable comparison.

Clause 2. The method of clause 1 or clause 1.1 including: F) if the center frequency response does not compare favorably with the expected center frequency response, exciting the sensor with one or more electromagnetic test signals having test frequencies different than the center frequency and monitoring for a test frequency response at each test frequency and, if the test frequency response from the sensor compares favorably to an expected test frequency response corresponding to the test frequency, issuing a second output consistent with the favorable comparison between the test frequency response and the expected test frequency response corresponding to the test frequency; and G) if the test frequency response from the sensor does not compare favorably to an expected test frequency response corresponding to the test frequency at any of the test frequencies, issuing a third output consistent with the unfavorable comparison between the test frequency response and the expected test frequency response corresponding to the test frequency.

Clause 3. The method of clause 2 wherein the output issued at step F is issued in response to the favorable comparison without first exciting the sensor at any other test frequencies.

Clause 4. The method of clause 2 wherein the output issued at step F in response to the favorable comparison is not issued until the sensor has been excited at at least one frequency other than the test frequency that yielded the favorable comparison.

Clause 5. The method of clause 1 or clause 1.1 wherein the electromagnetic signals are radio frequency signals.

Clause 6. The method of clause 1 or clause 1.1 wherein the one or more sensors is an RFID sensor.

Clause 7. The method of clause 1 or clause 1.1 wherein the first output is an indication that an incontinence pad is present and no incontinence is detected.

Clause 8. The method of clause 2 wherein the second output is an indication that an incontinence pad is present and incontinence is detected and wherein the third output is an indication that an incontinence pad is absent or a fault has occurred.

System for Detecting Incontinence or Other Moisture Caused Abnormality

Clause 101. A system for detecting the presence of moisture on an occupant support including: one or more moisture responsive sensors in a surveillance zone of the occupant support, the one or more sensors being tuned to a center frequency; a transceiver adapted to excite the one or more sensors with an electromagnetic signal having a frequency approximately equal to the center frequency and to monitor for a center frequency response from the one or more sensors; electrical circuitry adapted to compare the center frequency response to an expected center frequency response; and to issue a first output if the center frequency response compares favorably to an expected center frequency response.

Clause 102. The system of clause 101 wherein the electrical circuitry is adapted to respond as set forth below if the center frequency response does not compare favorably with the expected center frequency response: A) command the transceiver to excite the sensor with one or more electromagnetic test signals having test frequencies different than the center frequency; B) compare the test frequency response to an expected test frequency response corresponding to the test frequency; and C) if the test frequency response from the sensor compares favorably to an expected test frequency response corresponding to the test frequency, issuing a second output consistent with the favorable comparison between the test frequency response and the expected test frequency response corresponding to the test frequency; and D) if the test frequency response from the sensor does not compare favorably to an expected test frequency response corresponding to the test frequency at any of the test frequencies, issue a message consistent with the unfavorable comparison between the test frequency response and the expected test frequency response corresponding to the test frequency.

Clause 103. The system of clause 101 wherein the electromagnetic signals are radio frequency signals.

Clause 104. The system of clause 101 wherein the one or more sensors is an RFID sensor.

Clause 105. The system of clause 104 including an exposed sensor and a protected sensor.

Plus Multiple or Multiplexed Sensors

Clause 106. The system of clause 101 including two or more sensors at least some of which are individual sensors each coupled to an antenna.

Clause 107. The system of clause 106 wherein all of the sensors are individual sensors each coupled to an antenna.

Clause 108. The system of clause 101 including two or more sensors at least some of which are individual antenna components of a sensor assembly.

Clause 109. The system of clause 106 wherein all of the sensors are individual antenna components of a sensor assembly.

Rate of Change Based Method of Sensor Interrogation for Detecting Incontinence or Other Moisture Caused Abnormality.

Clause 201. A method of interrogating a sensor to detect the presence of moisture on an occupant support including: A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) calculating a rate of change based on the center frequency responses received at different times; E) comparing the rate of change to one or more thresholds; and F) issuing an output depending on the comparison.

Clause 202. The method of clause 201 wherein the calculated rate of change is a function of a change in RSSI over an interval of time.

Clause 203. The method of clause 202 wherein the calculated rate of change is a function of the difference between two excitation frequencies each of which produces a response having approximately equal RSSI values.

Clause 204. The method of clause 201 wherein the electromagnetic signals are radio frequency signals.

Clause 205. The method of clause 201 wherein the sensor is an RFID sensor.

Clause 206. The method of clause 201 wherein the thresholds are TMOIST and TMOVE and wherein the issued output is as set forth in the table below in which the rate of change is denoted as dR/dt:

| Condition | Issued Output |
| --- | --- |
| dR/dt < TMOIST | First |
| TMOIST ≤ dR/dt < TMOVE | Second |
| TMOVE ≤ dR/dt | Third |

Clause 207. The method of clause 206 wherein the first output is an indication that an incontinence pad is present and no incontinence is detected, the second output is an indication that an incontinence pad is present and incontinence is detected, and the third output is an indication that an incontinence pad is absent.

Method of Sensor Interrogation for Detecting Incontinence or Other Moisture Caused Abnormality Based on Protected and Exposed Sensors.

Clause 301. A method of interrogating a sensor suite to detect the presence of moisture on an occupant support including: A) providing first and second moisture responsive sensors in a surveillance zone of the occupant support, the sensors each being tuned to a center frequency, the first sensor being protected from coming into contact with moisture which may be present in the surveillance zone and the second sensor being exposed to coming into contact with moisture which may be present in the surveillance zone; B) exciting the sensors with an electromagnetic signal having a frequency approximately equal to its center frequency; C) monitoring for a center frequency response from the sensors; D) comparing the center frequency responses to an expected center frequency response for each sensor; and E) issuing an output depending on the comparison as set forth below:

| Result of comparison (response vs. expected response) for first sensor | Result of comparison (response vs. expected response) for second sensor | Output |
| --- | --- | --- |
| RSSI strong | RSSI strong | no moisture detected sensor detected |
| RSSI strong | RSSI weak or absent | moisture detected |
| RSSI weak or absent | RSSI strong | fault |
| RSSI weak or absent | RSSI weak or absent | sensor not present or sensor moved or fault |

Clause 302. The method of clause 301 wherein the electromagnetic signals are radio frequency signals.

Clause 303. The method of clause 301 wherein the sensors are RFID sensors.

System for Detecting Incontinence or Other Moisture Caused Abnormality Based on Protected and Exposed Sensors.

Clause 401. A system for detecting the presence of moisture on an occupant support including: first and second moisture responsive sensors in a surveillance zone of the occupant support, each sensor being tuned to a center frequency; a transceiver adapted to excite each sensor with an electromagnetic signal having a frequency approximately equal to its center frequency and to monitor for a center frequency response from each sensor; electrical circuitry adapted to compare the center frequency response of the first sensor to an expected center frequency response of the first sensor and to compare the center frequency response of the second sensor to an expected center frequency response of the second sensor; and to issue an output depending on the comparison as set forth below:

| Result of comparison (response vs. expected response) for first sensor | Result of comparison (response vs. expected response) for second sensor | Output |
| --- | --- | --- |
| RSSI strong | RSSI strong | no moisture detected sensor detected |
| RSSI strong | RSSI weak or absent | moisture detected |
| RSSI weak or absent | RSSI strong | fault |
| RSSI weak or absent | RSSI weak or absent | sensor not present or sensor moved or fault |

Clause 402. The method of clause 401 wherein the electromagnetic signals are radio frequency signals.

Clause 403. The method of clause 401 wherein the sensors are RFID sensors.

Clause 404. The method of clause 401 wherein each sensor is tuned to approximately the same center frequency.

Method of Fluid Analysis

Clause 501. A method of interrogating a sensor to detect the presence of moisture on an occupant support and to analyze moisture which may be present including: A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) comparing the center frequency response to an expected center frequency response; and E) if the center frequency response compares favorably to an expected center frequency response, issuing a first output consistent with the favorable comparison; and F) if the center frequency response does not compare favorably with the expected center frequency response, exciting the sensor with one or more electromagnetic test signals having test frequencies different than the center frequency and monitoring for a test frequency response at each test frequency and, G) if the test frequency response from the sensor compares favorably to an expected test frequency response corresponding to the test frequency, correlating the test frequency response with a relationship of entity, fluid properties or both and issuing a second output consistent with the favorable comparison between the test frequency response and the expected test frequency response corresponding to the test frequency.

Clause 502. The method of clause 501 wherein: H) if the test frequency response from the sensor does not compare favorably to an expected test frequency response corresponding to the test frequency at any of the test frequencies, issuing a third output consistent with the unfavorable comparison between the test frequency response and the expected test frequency response corresponding to the test frequency.

Clause 503. The method of clause 502 wherein the output issued at step G is issued in response to the favorable comparison without first exciting the sensor at any other test frequencies.

Clause 504. The method of clause 502 wherein the output issued at step G in response to the favorable comparison is not issued until the sensor has been excited at at least one frequency other than the test frequency that yielded the favorable comparison.

Clause 505. The method of clause 501 wherein the first output is an indication that a moisture sensing device is present and no moisture is detected.

Clause 506. The method of clause 501 wherein the second output is an indication that a moisture sensing device is present and moisture is detected and wherein the second output is also an indication of the identity of the fluid, the type of fluid or both as defined by the relationship between test frequency response and fluid identity, fluid properties or both.

Clause 507 The method of clause 502 wherein the third output is an indication that a moisture sensing device is absent or a fault has occurred.

Method for Detecting Incontinence or Other Moisture Caused Abnormality using Multiple RFID's or other sensors or Using Multiplexed RFID's or Other Sensors.

Clause 601. A method of detecting the presence of moisture on an occupant support, displacement of a moisture sensor or both including: A) providing two or more moisture responsive sensors in a surveillance zone of the occupant support, the sensors being tuned to a center frequency; B) exciting the sensors with an electromagnetic signal having a frequency approximately equal to the center frequency; C) monitoring for and receiving center frequency responses from the sensors and recording the individual center frequency responses at a time t=0; D) continuing to excite the sensors and to monitor for and receive responses at time t>t0. E) detecting differences in center frequency response for each sensor at one or more times t>0; and F) analyzing the differences in center frequency response to discern moisture presence, sensor displacement or both.

Clause 602. The method of clause 601 wherein the sensors are individual sensors each coupled to an antenna.

Clause 603. The method of clause 601 wherein the sensors are individual antenna components of a sensor assembly.

Clause 604. The method of clause 601 wherein moisture detection is declared as a result of: A) center frequency response from a first set of one or more sensors having become weaker at a time t>0 relative to the center frequency response of the one or more sensors at an earlier time, and B) the response of a second set of sensors which does not include members of the first set having substantially the same response strength at time t>0 than at the earlier time.

Clause 605. The method of clause 601 wherein sensor displacement is declared as a result of center frequency response from substantially all the sensors having become weaker at a time t>0 relative to the center frequency response of the sensors at an earlier time.

Method for Detecting Incontinence or Other Moisture Caused Abnormality Using Multiple RFID's or Other Sensors or Using Multiplexed RFID's or Other Sensors and Based on Highest Return Signal Strength.

Clause 701. A method of detecting the presence of moisture on an occupant support including: A) providing two or more moisture responsive sensors in a surveillance zone of the occupant support, the sensors being tuned to a center frequency; B) exciting the sensors with an electromagnetic signal having a frequency approximately equal to the center frequency; C) monitoring for and receiving center frequency responses from the sensors and identifying which sensor returns the strongest response; D) continuing to excite the sensors and to monitor for and receive center frequency responses; E) monitoring the sensors for changes in return signal strength in response to the continuing excitation relative to the excitation at step B; and F) analyzing the return signal strengths from the excitation at step B in comparison to those from the excitations at step D and: G) if the analysis of step E demonstrates that the return signal strength of the identified sensor has diminished over time, further analyzing the differences in center frequency response of one or more sensors other than the identified sensor to detect moisture presence or sensor displacement or both.

System for Detecting Incontinence or Other Moisture Caused Abnormality Using Multiple RFID's or Other Sensors or Using Multiplexed RFID's or Other Sensors.

Clause 801. A system for detecting the presence of moisture on an occupant support or displacement of a sensor or both including: multiple moisture responsive sensors spatially distributed in a surveillance zone of the occupant support, each sensor being tuned to a center frequency and having at least one antenna; a transceiver adapted to excite the sensors with an electromagnetic signal having a frequency approximately equal to the center frequency and to monitor for a center frequency response from the sensor; a multiplexer in communication with each antenna and with the transceiver; electrical circuitry adapted to command the transceiver to excite the sensors and to compare the center frequency response of each sensor to an expected center frequency response to detect the presence of moisture on the occupant support or displacement of a sensor or both.

Clause 802. The system of clause 801 wherein at least some of the sensors are individual sensors each coupled to an antenna and the electrical circuitry is adapted to command the multiplexer to acquire response signals from each antenna.

Clause 803. The system of clause 802 wherein all of the sensors are individual sensors each coupled to an antenna and the electrical circuitry is adapted to command the multiplexer to acquire response signals from each antenna.

Clause 804. The system of clause 801 wherein at least some of the two or more sensors are individual antenna components of a sensor assembly and the electrical circuitry is adapted to command the multiplexer to acquire response signals from each antenna component.

Clause 805. The system of clause 804 wherein all of the two or more sensors are individual antenna components of a sensor assembly and the electrical circuitry is adapted to command the multiplexer to acquire response signals from each antenna component.

Hybrid Incontinence Detection System

Clause 901. A system for detecting the presence of moisture on an occupant support including: a moisture responsive sensor in a surveillance zone of the occupant support, the sensor being adapted to issue a return signal in response to an electromagnetic excitation signal; a transceiver adapted to excite the sensor with an electromagnetic signal, the transceiver being integrated into the occupant support.

Clause 902. The system of clause 901 including an electrical circuitry adapted to receive the return signal and to issue an output based on a relationship between the return signal and the excitation signal Clause 903. The system of clause 901 wherein the electrical circuitry is a component of the transceiver.

Clause 904. The system of clause 901 wherein the integrated transceiver is integrated into a bed frame.

Clause 905. The system of clause 901 wherein the integrated transceiver is integrated into a mattress portion of the bed.

Clause 906. The system of clause 901 wherein the sensor is an RFID tag.

Clause 907. The system of clause 901 wherein the sensor is in the form of a sticker.

Clause 908. The system of clause 901 wherein the sensor is installed on a pad.

Clause 909. The system of clause 901 wherein the transceiver is adapted for communication with a facility information network 138.

Clause 910. The system of clause 901 wherein the transceiver includes an antenna which loops around the sensor.

Clause 911. The system of clause 910 wherein the antenna is selected from the group consisting of metal thread and conductive ink.

Fluid Reservoir (Absorbent or Dissolving)

Clause 1001. A moisture detection apparatus including: a deposition layer having an exposed side susceptible to moisture contamination and a nonexposed side; a moisture sensor having a moisture responsive element separated from the deposition layer by a reservoir material.

Clause 1002. The apparatus of clause 1001 wherein the reservoir material is adjacent the nonexposed side of the deposition layer.

Clause 1003. The apparatus of clause 1001 including a base layer, at least a portion of which is spaced from the deposition layer such that the reservoir material is between the base layer and the deposition layer.

Clause 1004. The apparatus of clause 1001 wherein the reservoir material is a reservoir layer and the sensor resides within the reservoir layer.

Clause 1005. The apparatus of clause 1004 including a base layer and wherein the reservoir layer is between the base layer and the deposition layer and the moisture responsive element faces toward the deposition layer.

Clause 1006. The apparatus of clause 1004 including a base layer and wherein the reservoir layer is between the base layer and the deposition layer and the moisture responsive element faces toward the base layer.

Clause 1007. The apparatus of clause 1001 wherein the reservoir material is localized and the sensor is encapsulated in the reservoir material.

Clause 1008. The apparatus of clause 1007 wherein the reservoir material forms a pocket to encapsulate the sensor.

Clause 1009. The apparatus of clause 1007 wherein the reservoir material is a coating which encapsulates the sensor.

Clause 1010. The apparatus of clause 1001 wherein the reservoir material is a coating over at least the moisture responsive element of the sensor.

Clause 1011. The apparatus of clause 1001 wherein the reservoir material is a lining.

Clause 1012. The apparatus of clause 1001 wherein the reservoir material is an absorbent material which retards migration of fluid from a fluid deposition site to the sensor element.

Clause 1013. The apparatus of clause 1001 or 1011 wherein the reservoir material is a woven textile.

Clause 1014. The apparatus of clause 1011 wherein the woven textile is selected from the group consisting of polyester, cotton and polyamide.

Clause 1015. The apparatus of clause 1001 wherein the reservoir material is a material which dissolves when exposed to moisture thereby retarding migration of the moisture from a fluid deposition site to the sensor element until dissolution of the material is complete enough to expose the sensor element to the fluid.

Clause 1016. The apparatus of clause 1001 or 1015 wherein the reservoir material is a polymer with the chemical formula: $-(CH_2-CHOR)_n-$ where R is $-H$ or $-COCH_3$.

Clause 1017. The apparatus of clause 1001 or 1015 wherein the reservoir material has the chemical formula: $-(CH_2-CHOR)_n-$ where R is $-H$ or $-COCH_3$.

Directional Architecture—Capillary.

Clause 1101. A moisture handling apparatus including a sheet of material having a capillary property for encouraging moisture migration from a source to a destination.

Clause 1102. The apparatus of clause 1101 including capillary tubes which impart the capillary property.

Clause 1103. The apparatus of clause 1101 including capillary fibers which impart the capillary property.

Clause 1104. The apparatus of clause 1101 wherein the capillary property is spatially arranged so as to encourage moisture migration from a source zone to a destination zone.

Clause 1105. The apparatus of clause 1104 wherein the apparatus extends laterally and longitudinally and the capillary property is arranged to define one or more capillary pathways extending substantially exclusively laterally from the source zone to the destination zone.

Clause 1106. The apparatus of clause 1104 wherein the apparatus extends laterally and longitudinally and the capillary property is arranged to define one or more capillary pathways extending both laterally and longitudinally from the source zone to the destination zone.

Clause 1107. The apparatus of clause 1104 wherein the capillary property is arranged to define one or more capillary pathways extending radially from the source zone to the destination zone.

Clause 1108. The apparatus of clause 1104 wherein the source zone is an inboard zone and the destination zone is an outboard zone.

Clause 1109. The apparatus of clause 1104 wherein the source zone is an outboard zone and the destination zone is an inboard zone.

Clause 1110. The apparatus of clause 1101 wherein the destination zone includes a sensor responsive to the moisture.

Clause 1111. The apparatus of clause 1110 wherein the sensor is an RFID technology sensor.

Clause 1112. The apparatus of clause 1101 wherein the destination zone includes an indicator responsive to the moisture.

Clause 1113. The apparatus of clause 1101 wherein the destination zone includes a collector for collecting the migrated moisture.

Clause 1114. The apparatus of clause 1101 wherein the destination zone is a collector for collecting the migrated moisture.

Clause 1115. The apparatus of clause 1101 wherein the sheet of material is a microfiber.

Clause 1116. The apparatus of clause 1115 wherein the microfiber sheet includes microfibers having a lineic mass of less than about 1 g/10 km.

Clause 1117. The apparatus of clause 1115 wherein the microfiber sheet includes microfibers which have a diameter of less than about 9 micrometers.

Clause 1118. The apparatus of clause 1115 wherein the microfiber sheet includes microfibers having a lineic mass of less than about 1 g/10 km and a diameter of less than about 9 micrometers.

Clause 1119. A system including the apparatus of clause 1101 and also including a sensor at the destination and electrical circuitry for processing information from the sensor.

Directional Architecture—Hydroaffinity.

Clause 1201. A moisture handling apparatus including a sheet of material having a hydroaffinity property for encouraging moisture migration from a source to a destination.

Clause 1202. The apparatus of clause 1201 wherein the hydroaffinity property is spatially arranged so as to encourage moisture migration from a source zone to a destination zone.

Clause 1203. The apparatus of clause 1202 wherein the apparatus extends laterally and longitudinally and the hydroaffinity property is arranged to define one or more fluid migration pathways extending substantially exclusively laterally from the source zone to the destination zone.

Clause 1204. The apparatus of clause 1202 wherein the apparatus extends laterally and longitudinally and the hydroaffinity property is arranged to define one or more fluid migration pathways extending both laterally and longitudinally from the source zone to the destination zone.

Clause 1205. The apparatus of clause 1202 wherein the hydroaffinity property is arranged to define one or more fluid migration pathways extending radially from the source zone to the destination zone.

Clause 1206. The apparatus of clause 1202 wherein the source zone is an inboard zone and the destination zone is an outboard zone.

Clause 1207. The apparatus of clause 1202 wherein the source zone is an outboard zone and the destination zone is an inboard zone.

Clause 1208. The apparatus of clause 1202 wherein the hydroaffinity property is arranged to be more hydrophobic at the source zone and more hydrophilic at the destination zone.

Clause 1209. The apparatus of clause 1201 wherein the destination zone includes a sensor responsive to the moisture.

Clause 1210. The apparatus of clause 1209 wherein the sensor is an RFID technology sensor.

Clause 1211. The apparatus of clause 1201 wherein the destination zone includes an indicator responsive to the moisture.

Clause 1212. The apparatus of clause 1201 wherein the destination zone includes a collector for collecting the migrated moisture.

Clause 1213. The apparatus of clause 1201 wherein the destination zone is a collector for collecting the migrated moisture.

Clause 1214. A system including the apparatus of clause 1201 and also including a sensor at the destination and electrical circuitry for processing information from the sensor.

Visual Indicators—Color Changing.

Clause 1301. A moisture detecting system including a sheet of material adapted to change color in response to the presence of moisture; a camera for observing the color change or lack thereof and a controller for issuing a response to the color change.

Clause 1302. The system of clause 1301 wherein an indicator portion of the sheet of material is adapted to change color in response to the presence of moisture and a transport portion is adapted to transport moisture from a site of deposition thereof to the indicator portion.

Clause 1303. The system of clause 1302 wherein the indicator portion is a perimetral portion.

Clause 1304. The system of clause 1302 wherein the indicator portion is an edge portion along a lateral side of the sheet.

Visual Indicators—UV from any Source, Plus Camera.

Clause 1401 A moisture detecting system including: a sheet of material which receives the moisture; a source of ultraviolet radiation adapted to expose at least a target portion of the sheet of material to the ultraviolet radiation; and a camera for observing emission of radiation or lack thereof in response to the presence of moisture within the target region and excitation of the moisture by the ultraviolet radiation; and a controller for responding to the observation.

Clause 1402. The system of clause 1401 wherein the source of ultraviolet radiation includes a light tube that extends through the sheet.

Clause 1403. The system of clause 1401 wherein the controller periodically activates and deactivates the source of ultraviolet radiation.

Clause 1404. The system of clause 1401 wherein the sheet of material is chemically treated to intensify the radiated emission.

Visual Indicators—UV from Light Tube.

Clause 1501 A moisture detecting system including: a sheet of material which receives the moisture; a source of ultraviolet radiation adapted to expose at least a target portion of the sheet of material to the ultraviolet radiation, the source including an ultraviolet radiation generator and a light tube that extends through the sheet for distributing the ultraviolet radiation to the target region.

Clause 1502. The system of clause 1501 including a camera for observing emission of radiation or lack thereof in response to the presence of moisture within the target region and excitation of the moisture by the ultraviolet radiation; and a controller for responding to the observation.

Clause 1503. The system of clause 1501 including a controller which periodically activates and deactivates the source of ultraviolet radiation.

Clause 1504. The system of clause 1501 wherein the sheet of material is chemically treated to intensify the radiation emitted in response to the presence of moisture within the target region and excitation of the moisture by the ultraviolet radiation.

Multifunctional Sensor Pad

Clause 1601. A sensor pad including: at least one RFID tag, the tag including electrical circuitry adapted to process inputs obtained from multiple sensors having disparate sensing capabilities.

Clause 1602. The pad of clause 1601 wherein at least one of the sensors is a moisture sensor.

Clause 1603. The pad of clause 1601 wherein the RFID tag or tags has a mode of operation indicative of moisture and wherein at least one of the sensors senses a parameter other than moisture.

Clause 1604. The pad of clause 1601 wherein the multiple sensors have sensing capabilities selected from the group consisting of moisture, odor, chemical identity identification, chemical property identification, interface pressure, vital signs of a patient associated with the pad, and sound.

Clause 1605. The pad of clause 1601 wherein the multiple sensors are selected from the group consisting of an accelerometer, a piezoelectric device, a piezoresistive device, a vibration sensor, a capacitive sensor, an inductive sensor and a resistive sensor.

Sensor/Switch Closed by Dissolution of Insulator.

Clause 1701. A sensor including a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse.

Clause 1702. The sensor of clause 1701 wherein the fuse includes an insulator for impeding the establishment of the electrical connection, the insulator being dissolvable in response to the presence of urine thereon.

Clause 1703. The sensor of clause 1701 wherein the stimulus is the presence of urine on the fuse.

Sensor Mat with Sensor/Switch Closed by Dissolution of Insulator.

Clause 1801. A sensor mat including: a sensor including a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse; a battery; and a load; the switch being connected to the load and to the battery, the battery also being connected to the load.

Clause 1802. A sensor mat including: a sensor including a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse; and a battery; the switch being connected to the battery, the switch being connectable to a load; and the battery also being connectable to the load.

Clause 1803. A sensor mat including: a sensor including a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse, the switch being connectable to a battery and to a load.

Clause 1804. The sensor of clauses 1801, 1802 or 1803 wherein the load is an alarm.

RFID with Antenna Segments United by Dissolution of Insulator.

Clause 1901. A sensor including an RFID tag, the tag including at least two antenna segments, a bridge adapted to unite the segments, and a separator which is transitionable between a first state in which the separator impedes unification of the segments and a second state in which the separator does not impede unification of the segments, transition from the first state to the second state being in response to an agent acting on the separator.

Clause 1902. The sensor of clause 1901 wherein the agent is the presence of urine in contact with the separator.

Clause 1903. The sensor of clause 1901 wherein the agent is urine in contact with the separator and the separator is adapted to dissolve in response to urine being in contact with the separator.

Clause 1904. The sensor of clause 1901 including electrical circuitry.

Clause 1905. The sensor of clause 1901 including an adjunct sensor in communication with the electrical circuitry.

Clause 2000. A moisture management apparatus including: a plurality of layers of fabric material including a lower layer, a middle layer supported by the lower layer, and an upper layer supported by the middle layer, wherein: the upper layer includes an upper surface configured to interface with a body portion of a person, and the upper surface includes a hydrophilic material; the upper layer includes a lower surface opposite the upper surface, and the lower surface includes a hydrophobic material; the middle layer includes material that is configured to transfer moisture away from the upper surface and toward the lower layer; the lower layer includes an upper surface, and the upper surface of the lower layer includes a hydrophobic material; and a sensor positioned in the lower layer, wherein the sensor is to wirelessly indicate the presence of moisture in the moisture management apparatus to another device.

Clause 2001. The moisture management apparatus of clause 2000, wherein the lower layer includes an absorbent material proximate the sensor.

Clause 2002. The moisture management apparatus of clause 2000, wherein at least the middle layer includes a moisture-wicking fabric.

Clause 2003. The moisture management apparatus of clause 2000, wherein at least the middle layer includes a plurality of three-dimensional fibers arranged to direct moisture toward the lower layer.

Clause 2004. The moisture management apparatus of clause 2000, wherein the sensor includes a radio frequency identification (RFID) sensor to receive a signal generated by a transceiver that is spaced from the moisture management apparatus and transmit a response to the reference signal to the transceiver.

Clause 2005. The moisture management apparatus of clause 2000, wherein the upper and lower layer cooperate to define an enclosed interior region including the middle layer.

Clause 2006. The moisture management apparatus of clause 2000, wherein the sensor wirelessly indicates the presence of moisture in the moisture management apparatus to another device that is spaced from the sensor.

Clause 2007. A moisture management apparatus including: a plurality of layers of fabric material including an upper layer to interface with a body portion of a person, and a lower layer spaced from the upper layer by a middle layer, wherein the lower layer has a greater ability to absorb moisture than either the middle layer or the upper layer; and a sensor positioned in the lower layer; wherein the sensor is to wirelessly indicate the presence of moisture in the moisture management apparatus to another device.

Clause 2008. The moisture management apparatus of clause 2007, wherein the moisture management apparatus includes a disposable pad.

Clause 2009. The moisture management apparatus of clause 2007, wherein the moisture management apparatus includes a reusable pad.

Clause 2010. The moisture management apparatus of clause 2007, wherein a different physico-chemical modification is applied to each of the upper layer, the middle layer, and the lower layer to provide a moisture absorption gradient to direct moisture away from the upper surface of the upper layer and toward the lower layer.

Clause 2011. The moisture management apparatus of clause 2007, wherein each of the upper layer, the middle layer, and the lower layer has a different structural arrangement of fibers to provide a moisture absorption gradient configured to direct moisture away from the upper surface of the upper layer and toward the lower layer.

Clause 2012. The moisture management apparatus of clause 2007, wherein the lower layer has a greater ability to absorb moisture than the middle layer, and the middle layer has a greater ability to absorb moisture than the upper layer.

Clause 2013. A moisture management apparatus including: a layer of fabric material including an arrangement of fluid conducting pathways, each of the fluid conducting pathways to direct fluid to a fluid collecting region of the layer of material; and a sensor positioned in the fluid collecting region; wherein the sensor is to wirelessly indicate the presence of moisture in the moisture management apparatus.

Clause 2014. The moisture management apparatus of clause 2013, wherein the layer of fabric material includes a surface modified by a physio-chemical treatment to define the fluid conducting pathways.

Clause 2015. The moisture management apparatus of clause 2013, wherein the layer of fabric material includes a plurality of fibers arranged to define the fluid conducting pathways.

Clause 2016. The moisture management apparatus of clause 2013, wherein the layer of material includes a plurality of contiguous edges defining a perimeter of the moisture management apparatus, the fluid collecting region is positioned adjacent one of the edges, and the fluid conducting pathways are configured to direct moisture toward the fluid collecting region.

Clause 2017. The moisture management apparatus of clause 2016, wherein the fluid conducting pathways are arranged as rays emanating from the fluid collecting region across the layer of fabric material.

Clause 2018. The moisture management apparatus of clause 2013, wherein the layer of material includes a plurality of contiguous edges defining a perimeter of the moisture management apparatus, the fluid collecting region is spaced from the edges in a central region of the moisture management apparatus, and the fluid conducting pathways are configured to direct moisture toward the sensor.

Clause 2019. The moisture management apparatus of clause 2018, wherein the fluid conducting pathways are arranged as closed shapes emanating concentrically from the fluid collecting region toward the perimeter of the moisture management apparatus.

Clause 2020. A moisture management apparatus including: a plurality of layers of fabric material, including an upper layer, a lower layer, and a middle layer separating the upper layer from the lower layer, wherein: the upper layer has an upper surface configured to interface with a body portion of a person; the upper layer includes a moisture absorbent material; and the middle layer includes a moisture impermeable material; a first sensor positioned in the upper layer, wherein the first sensor is to wirelessly indicate the presence of moisture in the upper layer to another device; and a second sensor positioned in the lower layer, wherein the second sensor is to wirelessly indicate the presence of the moisture management apparatus to the other device.

Clause 2021. The moisture management apparatus of clause 2020, including a transceiver to transmit wireless signals for receipt by the first sensor and the second sensor, wherein the first sensor is positioned so that when a moisture event occurs, moisture in the upper layer prevents the wireless signals from being received by the first sensor.

Clause 2022. The moisture management apparatus of clause 2020, wherein the plurality of layers of fabric material cooperate to define a pad, and the transceiver is coupled to a support surface that supports the pad.

Clause 2023. The moisture management apparatus of clause 2020, wherein the support surface includes a deck section of a person support apparatus.

Clause 2024. The moisture management apparatus of clause 2020, wherein the first sensor and the second sensor include radio frequency identification (RFID) sensors.

Clause 3165. A patient support apparatus including a frame; a deck supported by the frame, the deck to support a patient in at least a horizontal position; and a moisture management apparatus supported by the frame or the deck, the moisture management apparatus including: a moisture-responsive sensor to detect the presence of patient-produced moisture in an area supported by the frame or the deck; and electrical circuitry to communicate a moisture detection indication to a user interface device in response to a detecting by the sensor of patient-produced moisture in the area supported by the frame or the deck.

Clause 3166. The patient support apparatus of clause 3165, wherein the moisture-responsive sensor is to receive a first electromagnetic signal transmitted by the electrical circuitry, the moisture-responsive sensor is to transmit a second electromagnetic signal in response to the first electromagnetic signal, and the electrical circuitry is to generate the moisture detection indication based on the first and second electromagnetic signals.

Clause 3167. The patient support apparatus of clause 3165 or 3166, including a patient support surface supported by the deck, wherein the patient support surface includes the moisture-responsive sensor.

Clause 3168. The patient support apparatus of clause 3167, including an antenna to receive the second electromagnetic signal.

Clause 3169. The patient support apparatus of clause 3168, wherein the moisture-responsive sensor is located in the patient support surface and the antenna is supported by the frame or the deck of the patient support apparatus.

Clause 3170. The patient support apparatus of clause 3165 or clause 3166, wherein the deck includes a head section, a seat section, and a foot section, and the antenna is supported by the seat section of the deck.

Clause 3171. The patient support apparatus of clause 3166, wherein the patient support surface includes a moisture absorbent pad having a border defined by a plurality of spaced-apart edges, and the moisture-responsive sensor is located adjacent the border of the pad.

Clause 3172. The patient support apparatus of clause 3171, wherein the moisture absorbent pad includes a moisture-directing circuit coupled to the moisture-responsive sensor, and wherein the moisture-directing circuit is arranged in a serpentine pattern across a substantially planar surface of the moisture absorbent pad.

Clause 3173. The patient support apparatus of clause 3171, wherein the moisture absorbent pad includes spaced-apart substantially planar top and bottom surfaces defining an interior region, and wherein the moisture-responsive sensor is spaced-apart from both the top and bottom surfaces and the moisture-responsive sensor is positioned in the interior region.

Clause 3174. The patient support apparatus of clause 3165 or clause 3166, wherein the electrical circuitry is to communicate the moisture detection indication to a network for use by a healthcare communication system.

Clause 3175. The patient support apparatus of clause 3165, or clause 3166, wherein the electrical circuitry is to wirelessly communicate the moisture detection indication to a mobile computing device including the user interface device.

Clause 3176. The patient support apparatus of clause 3165 or clause 3166, wherein the user interface device is coupled to the frame of the patient support apparatus.

Clause 3177. The patient support apparatus of clause 3165, 3175, or clause 3176, wherein the user interface device includes an input mechanism to select one of a plurality of moisture levels for monitoring by the moisture management apparatus.

Clause 3178. The patient support apparatus of clause 3177, wherein the electrical circuitry is to communicate the moisture detection indication only when the moisture-responsive sensor detects an amount of moisture that meets or exceeds the selected moisture level.

Clause 3179. The patient support apparatus of clause 3165 or clause 3166, wherein the electrical circuitry is to detect the presence or absence of the moisture-responsive sensor on the patient support apparatus.

Clause 3180. The patient support apparatus of clause 3179, wherein the electrical circuitry is to communicate a sensor present indication to the user interface device in response to detecting the presence of the moisture-responsive sensor on the patient support apparatus, and the user interface device is to visually present the sensor present indication on the user interface device.

Clause 3181. A user interface device for a patient support apparatus, the user interface device including: a housing defining an interior region; electrical circuitry in the interior region, the electrical circuitry to receive a signal from a moisture management apparatus, the moisture management apparatus to monitor an amount of patient-generated moisture in an area supported by the patient support apparatus, the signal indicating data relating to the operation of a moisture-responsive sensor of the moisture management apparatus; and a visual indicator supported by the housing, the visual indicator to activate in response to a receiving of the signal by the electrical circuitry.

Clause 3182. The user interface device of clause 3181, including a plurality of input mechanisms supported by the housing, wherein each of the user interface mechanisms is to select a different amount of moisture to be monitored by the moisture management apparatus.

Clause 3183. The user interface device of clause 3181 or clause 3182, wherein the electrical circuitry is to receive a sensor present signal from the moisture management apparatus, the sensor present signal indicating that the moisture-responsive sensor is positioned on the patient support apparatus, and wherein the visual indicator includes a light to illuminate in response to the sensor present signal.

Clause 3184. The user interface device of clause 3181 or clause 3182, including a graphical user interface to graphically display data indicating one or more areas of moisture detected by the moisture management apparatus in the area supported by the patient support apparatus.

Clause 3185. The user interface device of clause 3181 or clause 3182, wherein the user interface device is embodied in a mobile computing device.

Clause 4101. A moisture management apparatus for monitoring an area for the occurrence of moisture events in the area, the moisture management apparatus including: a substrate having a length and a width, the length and the width defining a monitoring area; a wireless sensor coupled to the substrate; a first electrically conductive trace supported by the substrate and connected to an first input of the wireless sensor, the first electrically conductive trace comprising a plurality of segments connected end-to-end in a continuous manner to form a first pattern across the monitoring area; and a second electrically conductive trace supported by the substrate and connected to a second input of the wireless sensor, the second electrically conductive trace comprising a plurality of segments connected end-to-end in a continuous manner to form a second pattern across the monitoring area, wherein: a segment of the second pattern is spaced apart from a segment of the first pattern by a distance; the distance between the segment of the second pattern and the segment of the first pattern is defined by a moisture management criterion; and the wireless sensor is configured to, in response to the presence of moisture between the segment of the second pattern and the segment of the first pattern, emit a signal indicative of a moisture event.

Clause 4102. The moisture management apparatus of clause 4101, wherein the wireless sensor is configured to emit the signal indicative of a moisture event in response to a triggering signal received wirelessly by the sensor from a wireless signal transmitter.

Clause 4103. The moisture management apparatus of clause 4101 or clause 4102, wherein a segment of the second pattern is interposed between two segments of the first pattern, and the interposed segment of the second pattern is spaced apart from each of the two segments of the first pattern by the distance.

Clause 4104. The moisture management apparatus of any of clauses 4101-4103, wherein a segment of the first pattern is connected to another segment of the first pattern to form an angle that is less than 180 degrees.

Clause 4105. The moisture management apparatus of any of clauses 4101-4104, wherein each of the first and second electrically conductive traces comprises an electrically conductive material coupled to a top surface of the substrate.

Clause 4106. The moisture management apparatus of clause 4105, wherein the electrically conductive material comprises an electrically conductive ink, and the electrically conductive ink is printed on the substrate.

Clause 4107. The moisture management apparatus of any of clauses 4101-4106, wherein the substrate comprises a support material configured to, when the moisture management apparatus supports a portion of a patient's weight, increase the patient's peak interface sacral pressure by an amount that is less than or equal to about 15 millimeters of mercury (mm/Hg).

Clause 4108. The moisture management apparatus of any of clauses 4101-4107, wherein the substrate comprises a synthetic resin or a thermoplastic polymer material.

Clause 4109. The moisture management apparatus of any of clauses 4101-4108, wherein the substrate comprises a film material having a thickness in the range of about one millimeter.

Clause 4110. The moisture management apparatus of any of clauses 4101-4109, comprising a detuning apparatus coupled to the sensor.

Clause 4111. The moisture management apparatus of any of clauses 4101-4110, wherein the sensor comprises a first connection point to which an end of the first electrically conductive trace is connected and a second connection point to which an end of the second electrically conductive trace is connected, the first and second connection points are separated by a gap, and the gap is sized to maintain a distance between the first electrically conductive trace and the second electrically conductive trace.

Clause 4112. The moisture management apparatus of clause 4111, wherein the gap is sized to prevent an electrical connection between the first electrically conductive trace and the second electrically conductive trace from occurring in the absence of a moisture event.

Clause 4113. The moisture management apparatus of any of clauses 4101-4112, wherein the sensor comprises an authentication mechanism configured to wirelessly communicate sensor authentication information for receipt by another device.

Clause 4114. The moisture management apparatus of any of clauses 4101-4113, wherein the moisture management criterion comprises a moisture-related property of the substrate.

Clause 4115. An incontinence pad comprising the moisture management apparatus of any of clauses 4101-4114, a layer of moisture absorbent material supported by the moisture management apparatus of any of clauses 4101-4114, and a layer of a moisture impermeable material supporting the moisture management apparatus of any of clauses 4101-4114 and the layer of moisture absorbent material.

Clause 4116. The moisture management apparatus of clause 4115, wherein the moisture management criterion comprises a moisture-related property of the moisture absorbent material of the incontinence pad.

Clause 4117. The moisture management apparatus of any of clauses 4101-4116, wherein the sensor comprises a passive radio frequency identification (RFID) sensor to emit the sensor signal at a frequency configured for monitoring moisture events.

Clause 4118. The moisture management apparatus of any of clauses 4101-4117, wherein the first electrically conductive trace and a second electrically conductive trace are differently electrically charged.

Clause 4119. A moisture event communication system, the moisture event communication system including: an antenna configured to wirelessly receive a sensor signal emitted by a sensor located in an area monitored by the antenna, the sensor signal emitted by the sensor in response to a moisture event occurring in the monitored area, the sensor signal indicative of the moisture event; and a reader configured to: wirelessly receive the sensor signal from the antenna; selectively control power to the antenna to cause the antenna to receive signals from the sensor; and transmit the sensor signal received by the antenna to a notification device.

Clause 4120. The moisture event communication system of clause 4119, wherein the antenna is configured to wirelessly receive a sensor identifier signal emitted by the sensor and the reader is configured to: verify the sensor identifier signal; and in response to the verification of the sensor identifier signal, transmit the sensor signal received by the antenna to the notification device.

Clause 4121. The moisture event communication system of clause 4119 or clause 4120, comprising a plurality of antennas, wherein the reader is configured to selectively control power to each of the antennas to define a plurality of different moisture event monitoring zones.

Clause 4122. The moisture event communication system of any of clauses 4119-4121, comprising a plurality of antennas, wherein the reader is configured to selectively control power to each of the antennas to define a plurality of different monitoring zones, wherein at least two of the monitoring zones monitor different types of sensor events.

Clause 4123. The moisture event communication system of any of clauses 4119-4122, comprising a patient support surface, wherein the antenna is positioned adjacent to the patient support surface, and the reader is configured to control power to the antenna to define a moisture event monitoring zone above the patient support surface.

Clause 4124. The moisture event communication system of any of clauses 4119-4123, comprising a patient support apparatus, a first antenna, and a second antenna, wherein the patient support apparatus comprises a frame and a deck supported by a frame, a first antenna is mounted to the deck, a second antenna is mounted to the frame, and the reader is configured to control power to the first and second antennas to define a plurality of different monitoring zones adjacent the patient support apparatus.

Clause 4125. The moisture event communication system of clause 4124, wherein the reader is configured to control power to the first and second antennas to define a first monitoring zone located above the deck and a second monitoring zone extending in a horizontal direction from a side of the patient support apparatus a distance away from the patient support apparatus.

Clause 4126. The moisture event communication system of clause 4125, wherein the second monitoring zone further extends in a vertical direction from a top surface of the patient support apparatus downwardly toward a floor supporting the patient support apparatus.

Clause 4127. The moisture event communication system of any of clauses 4119-4126, wherein the sensor comprises a passive radio frequency identification (RFID) sensor to emit the sensor signal at a frequency configured for monitoring moisture events, and the antenna comprises a passive radio frequency (RF) antenna configured to operate at a power level to receive the sensor signal emitted by the sensor at the frequency configured for monitoring moisture events.

Clause 4128. The moisture event communication system of any of clauses 4119-4127, wherein the reader is to selectively control the power to the antenna and control the frequency at which the sensor emits sensor signals in accordance with antenna power and sensor frequency requirements for monitoring a particular type of sensor event.

Clause 4129. The moisture event communication system of any of clauses 4119-4128, wherein the reader is to determine how frequently to communicate sensor signals emitted by the sensor to the notification device based on one or more of: a characteristic of a patient associated with the sensor and a characteristic of a caregiver associated with the patient, and the reader is to transmit the sensor signals to the notification device according to the determined communication frequency.

Clause 4130. A patient support apparatus including: a frame; a deck supported by the frame, the deck to support a patient in at least a horizontal position; and an antenna coupled to a top surface of the deck, the antenna configured to wirelessly receive a sensor signal emitted by a sensor and wirelessly transmit the sensor signal to a reader, the sensor signal emitted by the sensor in response to a moisture event occurring in a moisture event monitoring area located adjacent the deck, the sensor signal indicative of the moisture event.

Clause 4131. The patient support apparatus of clause 4130, wherein the deck includes a head section, a foot section, and a seat section located between the head section and the foot section, and wherein the antenna is mounted to a top surface of the seat section of the deck.

Clause 4132. The patient support apparatus of clause 4130 or clause 4131, including a patient support surface supported by the deck, wherein the antenna is located between the deck and the patient support surface.

Clause 4133. The patient support apparatus of any of clauses 4130-4132, including a second antenna mounted to the frame, wherein the second antenna is to wirelessly receive a sensor signal emitted by a sensor located in a different monitoring area than the moisture event monitoring area.

Clause 4134. The patient support apparatus of clause 4133, including the reader, wherein the reader is to selectively vary an amount of power supplied to the antenna and the second antenna.

Clause 4135. The patient support apparatus of any of clauses 4130-4133, including the reader, wherein the reader is to selectively vary an amount of power supplied to the antenna.

Clause 4136. The patient support apparatus of any of clauses 4130-4135, including a visual indicator mounted to the frame, wherein the visual indicator is configured to visually indicate an occurrence of the moisture event.

Clause 4137. A method for monitoring a plurality of different types of sensor events with a patient support apparatus, the patient support apparatus configured to support patients in at least a horizontal position, the method including: with an antenna coupled to the patient support apparatus, wirelessly receiving a signal from a sensor located adjacent the patient support apparatus, the signal indicative of a sensor type; with a reader coupled to the patient support apparatus: wirelessly receiving the sensor signal from the antenna; if the sensor type indicates that the sensor is to monitor patient moisture events, power the antenna to monitor for moisture events; and if the sensor type indicates that the sensor is to monitor patient fall events, power the antenna to monitor for patient fall events.

Clause 4138. The method of clause 4137, comprising, with the antenna, wirelessly receiving an identification signal identifying the sensor, verifying the identification signal, and if the identification signal is successfully verified, initiating the monitoring for sensor events based on the sensor type.

Clause 4139. The method of clause 4137 or clause 4138, comprising, with the antenna and the reader, detecting a patient moisture event, reading a characteristic of the patient producing the patient moisture event, and if the characteristic indicates that the patient has a fall risk, sending an urgent notification to a caregiver.

Clause 4140. The method of clause 4137 or clause 4138, comprising, with the antenna and the reader, detecting a patient moisture event, reading a characteristic of the patient producing the patient moisture event wherein if the characteristic indicates that the patient has a risk of skin breakdown, sending an urgent notification to a caregiver.

Clause 4141. The method of clause 4137 or clause 4138, wherein if the characteristic does not indicate that the patient has a risk of skin breakdown and the characteristic does not indicate that the patient has a fall risk, sending a non-urgent notification to a caregiver.

While certain features have been described in the context of certain illustrative embodiments, it should be understood that such features may be adopted or applied to any of the disclosed embodiments or to other embodiments.

What is claimed is:

1. A moisture event communication system comprising:
an antenna configured to wirelessly receive a sensor signal emitted by a sensor located in an area monitored by the antenna, the sensor signal emitted by the sensor in response to a moisture event occurring in the monitored area, the sensor signal indicative of the moisture event;
a reader configured to:
wirelessly receive the sensor signal from the antenna;
selectively vary an amount of power supplied to the antenna to adjust a size of an area in which the antenna is able to read the sensor signal emitted from the sensor;
transmit the sensor signal received by the antenna to a notification device; and
a patient support apparatus to which the reader is coupled, wherein the antenna comprises a first antenna, wherein the patient support apparatus comprises a frame and a deck supported by the frame, wherein the deck includes a movable deck section that is movably coupled to the frame, the first antenna is mounted to the movable deck section to move therewith relative to the frame, the second antenna is coupled to the frame, and the reader is configured to control power to the first and second antennas to define a plurality of different monitoring zones adjacent the patient support apparatus.

2. The moisture event communication system of claim 1, wherein the antenna is configured to wirelessly receive a sensor identifier signal emitted by the sensor and the reader is configured to:
verify the sensor identifier signal; and
in response to the verification of the sensor identifier signal, transmit the sensor signal received by the antenna to the notification device.

3. The moisture event communication system of claim 1, wherein the antenna is included as one of a plurality of antennas, and wherein the reader is configured to selectively control power to each of the antennas to define a plurality of different moisture event monitoring zones.

4. The moisture event communication system of claim 1, wherein the antenna is included as one of a plurality of antennas, wherein the reader is configured to selectively control power to each of the antennas to define a plurality of different monitoring zones, and wherein at least two of the monitoring zones monitor different types of sensor events.

5. The moisture event communication system of claim 1, further comprising a patient support surface, wherein the antenna is positioned adjacent to the patient support surface, and wherein the reader is configured to control power to the antenna to define a moisture event monitoring zone above the patient support surface.

6. The moisture event communication system of claim 1, wherein the reader is configured to control power to the first and second antennas to define a first monitoring zone located above the deck and a second monitoring zone extending in a horizontal direction from a side of the patient support apparatus a distance away from the patient support apparatus.

7. The moisture event communication system of claim 6, wherein the second monitoring zone further extends in a vertical direction from a top surface of the patient support apparatus downwardly toward a floor supporting the patient support apparatus.

8. The moisture event communication system of claim 1, wherein the sensor comprises a passive radio frequency identification (RFID) sensor to emit the sensor signal at a frequency configured for monitoring moisture events, and the antenna comprises a passive radio frequency (RF) antenna configured to operate at a power level to receive the sensor signal emitted by the sensor at the frequency configured for monitoring moisture events.

9. The moisture event communication system of claim 1, wherein the reader is configured to selectively control the power to the antenna and control the frequency at which the sensor emits sensor signals in accordance with antenna power and sensor frequency requirements for monitoring a particular type of sensor event.

10. The moisture event communication system of claim 1, wherein the reader is configured to determine how frequently to communicate sensor signals emitted by the sensor to the notification device based on one or more of: a characteristic of a patient associated with the sensor and a characteristic of a caregiver associated with the patient, and the reader is configured to transmit the sensor signals to the notification device according to the determined communication frequency.

11. The moisture event communication system of claim 1, wherein the sensor is included in an incontinence detection pad.

12. The moisture event communication system of claim 11, wherein the incontinence detection pad further includes a second sensor to sense odor.

13. The moisture event communication system of claim 11, wherein the incontinence detection pad further includes a second sensor to sense a chemical identity or a chemical property.

14. The moisture event communication system of claim 11, wherein the incontinence detection pad further includes a second sensor to sense interface pressure between the incontinence detection pad and a person situated atop the incontinence detection pad.

15. The moisture event communication system of claim 11, wherein the incontinence detection pad further includes a second sensor to detect sound.

16. The moisture event communication system of claim 11, wherein the incontinence detection pad further includes a second sensor to sense at least one vital sign of a person situated atop the incontinence detection pad.

17. The moisture event communication system of claim 16, wherein the vital sign sensed by the second sensor comprises one or more of the following: blood pressure, heart rate, respiration rate, skin temperature, or internal temperature.

18. The moisture event communication system of claim 11, wherein the incontinence detection pad further includes an accelerometer or a vibration sensor.

19. The moisture event communication system of claim 11, wherein the incontinence detection pad further includes a second sensor that operates based on piezoelectric, piezoresistive, capacitive, inductive, or resistive principles.

20. The moisture event communication system of claim 11, wherein the incontinence detection pad includes fluid migration pathways to direct moisture toward the sensor.

* * * * *